(12) United States Patent
Sommerlade et al.

(10) Patent No.: US 7,462,650 B2
(45) Date of Patent: Dec. 9, 2008

(54) TRIFUNCTIONAL PHOTOINITIATORS

(75) Inventors: Reinhard H. Sommerlade, Neuenburg am Rhein (DE); Rinaldo Hüsler, Basel (CH); Stephan Ilg, Giebenach (CH); André Fuchs, Schliengen-Obereggenen (DE); Souâd Boulmaâz, Birsfelden (CH); Jean-Luc Birbaum, Binningen (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 457 days.

(21) Appl. No.: 10/552,952

(22) PCT Filed: May 4, 2004

(86) PCT No.: PCT/EP2004/050689

§ 371 (c)(1),
(2), (4) Date: Oct. 13, 2005

(87) PCT Pub. No.: WO2004/099262

PCT Pub. Date: Nov. 18, 2004

(65) Prior Publication Data

US 2006/0270748 A1    Nov. 30, 2006

(30) Foreign Application Priority Data

May 6, 2003    (EP) .................................. 03405318

(51) Int. Cl.
C08F 2/46    (2006.01)
C07C 49/00    (2006.01)

(52) U.S. Cl. .......................... 522/36; 568/319; 568/323; 568/325; 568/336

(58) Field of Classification Search ................... 522/36, 522/60; 568/397, 410, 336, 319, 323, 325
See application file for complete search history.

(56) References Cited

U.S. PATENT DOCUMENTS

| | | | | |
|---|---|---|---|---|
| 4,097,538 A | * | 6/1978 | Factor et al. ................. | 568/726 |
| 4,308,400 A | | 12/1981 | Felder et al. ................. | 568/336 |
| 4,315,807 A | | 2/1982 | Felder et al. ................. | 522/33 |
| 4,318,791 A | | 3/1982 | Felder et al. ................. | 522/33 |
| 4,321,118 A | | 3/1982 | Felder et al. ................. | 522/36 |
| 4,374,984 A | | 2/1983 | Eichler et al. ................. | 544/80 |
| 4,496,447 A | | 1/1985 | Eichler et al. ................. | 522/34 |
| 4,992,547 A | | 2/1991 | Berner et al. ................. | 544/162 |

(Continued)

FOREIGN PATENT DOCUMENTS

| | | |
|---|---|---|
| DE | 3008411 | 9/1981 |
| DE | 197000641 | 7/1997 |
| EP | 0003002 | 7/1979 |
| EP | 0138754 | 4/1985 |
| JP | 55009028 | * 1/1980 |
| JP | 04011610 | 1/1992 |
| WO | 95/10552 | 4/1995 |
| WO | 02/48202 | 6/2002 |
| WO | WO 03/040076 | * 5/2003 |
| WO | WO 2004/009651 | * 1/2004 |

OTHER PUBLICATIONS

Derwent Abstract 1997-117236 for DE 19700064 (Jul. 1997).
Derwent Abstract 92-068346/09 for JP 04011610 (Jan. 1992).

*Primary Examiner*—Mark Eashoo
*Assistant Examiner*—Jessica Treidl
(74) *Attorney, Agent, or Firm*—Shiela A. Loggins

(57) ABSTRACT

The Invention relates to novel ketones of formulae (I) and (II) wherein $R_1$, $R_2$, $R_3$ and $R_4$ are, for example, $C_1$-$C_8$alkyl, $R_5$ is, for example, hydrogen, A is Cl, Br, -O-$R_7$, —$NR_8R_9$ or —S—$R_{16}$, A' is —O—, —NH— or —$NR_8$—, X and Y are each independently of the other —O—$R_{10}$ or —N($R_{11}$)($R_{12}$), n is an integer from 1 to 10, $R_6$ is, for example, an n-valent radical of linear or branched $C_2$-$C_{20}$alkyl the carbon chain of which may be interrupted by cyclohexanediyl, phenylene, —CH(OH)—, —C($C_2H_5$)($CH_2$—$CH_2$—OH)—, —C($CH_3$)($CH_2$—$CH_2$—OH)—, —C($CH_2$—$CH_2$—OH)$_2$—, —N($CH_3$)—, —N($C_2H_5$)—, —N($CH_2$—$CH_2$—OH)—, —CO—O—, —O—CO—, —P($CH_2$—$CH_2$—OH)—, —P(O)($CH_2$—$CH_2$—OH)—, -0-P(O—$CH_2$—$CH_2$—OH)—O—, -0-P(O)(0-$CH_2$—$CH_2$—OH)—O—, —O-cyclohexanediyl-C($CH_3$)$_2$-Cyclohexanediyl-O—, —O-phenylene-C($CH_3$)$_2$-phenylene-O—, —O-phenylene-$CH_2$-phenylene-O—, —Si($CH_3$)$_2$—, -0-Si($CH_3$)$_2$—O—, —O—Si($CH_3$)(0-$CH_3$)—O—, —Si($CH_3$)($R_{17}$)—O—Si($CH_3$)($R_{18}$)—, 5-(2-hydroxyethyl)-[1,3,5]triazinane-2,4,6-trione-1,3-diyl and/or by from one to nine oxygen atoms.

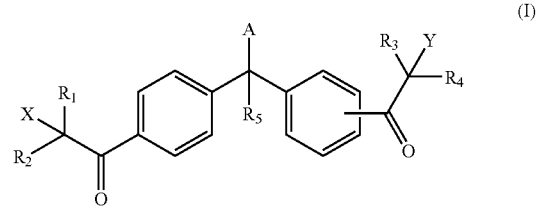

(I)

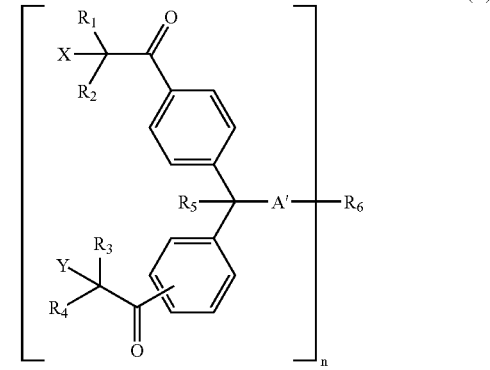

(II)

15 Claims, No Drawings

U.S. PATENT DOCUMENTS

| | | | |
|---|---|---|---|
| 5,145,885 A | 9/1992 | Berner et al. | 522/39 |
| 5,506,279 A | 4/1996 | Babu et al. | 522/34 |
| 6,296,986 B1 | 10/2001 | Illsley et al. | 430/281.1 |
| 6,441,244 B1 * | 8/2002 | Avar et al. | 568/327 |
| 2004/0034115 A1 | 2/2004 | Baudin et al. | 522/33 |
| 2005/0004249 A1 | 1/2005 | Fuchs et al. | 522/36 |

* cited by examiner

TRIFUNCTIONAL PHOTOINITIATORS

The invention relates to novel photoinitiators and to mixtures thereof for radiation-curable compositions, especially using ultraviolet and visible radiation, to intermediates for their preparation and to a process for the preparation of the initiators from the intermediates.

Radiation-curable systems can be used in a large number of applications, for example in overprint coatings, printing inks, in the manufacture of electronic printed circuit boards and printing plates, and in the coating of various substrates, such as wood, plastics, paper, glass or metal. For efficient polymerisation of such systems, it is necessary to use a photoinitiator, from which, as a result of interaction with electromagnetic radiation, reactive particles such as free radicals or cations (protons) are generated. A disadvantage of most of the initiators frequently used in practice is the undesirable odour that is produced when they are used. There is therefore a demand in the art for low-odour, low-volatility photoinitiators. In addition, it is desirable for the photoinitiator to contribute towards an improved crosslinking density and to produce fewer photolysis products that are capable of migration. Moreover, the photo-initiator should be available in an easy-to-handle form, should cause minimal yellowing of the cured film, and should be readily soluble in radiation-curable systems.

A further important criterion for the use of photoinitiators is the effectiveness with which the reactive constituents of the formulation are polymerised. This has a direct effect on the curing speed which can be achieved during use, and on the degree of crosslinking of the resulting polymer.

European Patent Application EP-A 003 002 describes the use of specific ketones as photo-initiators. The ketones have a tertiary alpha carbon atom, which is substituted by a hydroxyl group or an amino group or an etherification or silylation product thereof. The compound 4,4'-bis(α-hydroxy-isobutyryl)-diphenylmethane is listed by way of example, but its preparation is not described and characteristic properties of the compound are not mentioned.

European Patent EP-B-216884 describes Photoinitiators such as 2-hydroxy-1-[4-(2-hydroxy-ethoxy)-phenyl]-2-methyl-propan-1-one (Irgacure 2959®). This photoinitiator can be further reacted at the primary hydroxyl group.

The most frequently used α-hydroxy ketone is Darocur 1173® (2-hydroxy-2-methyl-1-phenyl-propan-1-one), a liquid photoinitiator, which is available commercially (from Ciba Specialty Chemicals).

It has now been found that α-hydroxy ketones, α-alkoxy ketones and α-amino ketones of the following formulae possess the required properties as photoinitiators and possess a lower volatility than Irgacure 2959® and a good reactivity at the benzhydryl position.

The invention accordingly relates to novel ketones of formulae I and II

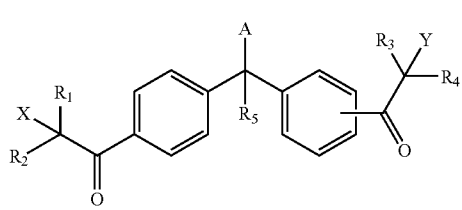

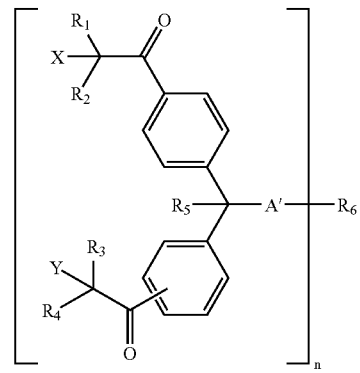

wherein $R_1$, $R_2$, $R_3$ and $R_4$ are each independently of the others $C_1$-$C_8$alkyl; $C_1$-$C_4$alkyl substituted by OH, $C_1$-$C_4$alkoxy, —CN, —COO($C_1$-$C_8$alkyl), ($C_1$-$C_4$alkyl)-COO—, benzyl, phenyl or by —N($R_{13}$)($R_{14}$); $C_3$-$C_6$alkenyl, benzyl, —$CH_2$—$C_6H_4$—($C_1$-$C_4$alkyl) or phenyl; or $R_1$ and $R_2$ together and/or $R_3$ and $R_4$ together are unbranched or branched $C_2$-$C_9$alkylene or $C_3$-$C_6$-oxa- or -aza-alkylene;

$R_5$ is hydrogen, $C_1$-$C_8$alkyl, $C_3$-$C_6$alkenyl, benzyl, —$CH_2$—$C_6H_4$—($C_1$-$C_4$alkyl) or phenyl;

A is Cl, Br, —O—$R_7$, —$NR_8R_9$ or —S—$R_{16}$;

A' is —O—, —NH— or —$NR_8$—;

X and Y are each independently of the other —O—$R_{10}$ or —N($R_{11}$)($R_{12}$);

n is an integer from 1 to 10, preferably an integer from 1 to 4, especially 1, 2 or 3;

$R_6$ is an n-valent radical of linear or branched $C_2$-$C_{20}$alkyl the carbon chain of which may be interrupted by cyclohexanediyl, phenylene, —CH(OH)—, —C($C_2H_5$)($CH_2$—$CH_2$—OH)—, —C($CH_3$)($CH_2$—$CH_2$—OH)—, —C($CH_2$—$CH_2$—OH)$_2$—, —N($CH_3$)—, —N($C_2H_5$)—, —N($CH_2$—$CH_2$—OH)—, —CO—O—, —O—CO—, —O—CO—NH, NH—CO—O—, —P($CH_2$—$CH_2$—OH)—, —P(O)($CH_2$—$CH_2$—OH)—, —O—P(O—$CH_2$—$CH_2$—OH)—O—, —O—P(O)(O—$CH_2$—$CH_2$—OH)—O—, —O-cyclohexanediyl-C($CH_3$)$_2$-cyclohexanediyl-O—, —O-phenylene-C($CH_3$)$_2$-phenylene-O—, —O-phenylene-$CH_2$-phenylene-O—, —Si($CH_3$)$_2$—, —O—Si($CH_3$)$_2$—O—, —O—Si($CH_3$)(O—$CH_3$)—O—, —Si($CH_3$)($R_{17}$)—O—Si($CH_3$)($R_{18}$)—, 5-(2-hydroxy-ethyl)-[1,3,5]triazinane-2,4,6-trione-1,3-diyl and/or by from one to nine oxygen atoms, or $R_6$ is an n-valent radical of linear or branched —CO—NH—($C_2$-$C_9$alkylene)-(NH—CO)$_{n-1}$— or linear or branched —CO—NH—($C_0$-$C_{16}$alkylene)-(NH—CO)$_{n-1}$— which may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl, 3-(6-isocyanatohexyl)-biuret-1,5-diyl or 5-(6-isocyanatohexyl)-[1,3,5]triazinane-2,4,6-trione-1,3-diyl radical(s), or $R_6$ is an n-valent radical of linear or branched —CO—($C_0$-$C_{12}$alkylene)-(CO)$_{n-1}$— and the alkylene may be interrupted by oxygen, phenylene, cyclohexanediyl or by norbornane-diyl, or $R_6$ is an n-valent radical of linear or branched —$C_2$-$C_{50}$alkylene the carbon chain of which is interrupted by one to 15 oxygen, and may be subsituted by OH or $NH_2$;

$R_7$ is hydrogen, —Si($C_1$-$C_6$alkyl)$_3$, $C_1$-$C_{12}$alkyl, $R_{21}$, $C_2$-$C_{18}$acyl, —CO—NH—$C_1$-$C_{12}$alkyl, $C_2$-$C_{20}$hydroxyalkyl, $C_2$-$C_{20}$methoxyalkyl, 3-($C_1$-$C_{18}$alkoxy)-2-hydroxy-propyl, 3-[1,3,3,3-tetramethyl-1-[(trimethylsilyl)oxy]disiloxanyl]-propyl, 2,3-dihydroxy-propyl or linear or branched $C_2$-$C_{21}$hydroxyalkyl or ($C_1$-$C_4$alkoxy)-$C_2$-$C_{21}$alkyl the carbon chain of which is interrupted by from one to nine oxygen atoms;

$R_8$ and $R_9$ are each independently of the other hydrogen, $C_1$-$C_{12}$alkyl; $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl, or when $R_9$=H or methyl, $R_8$ is also $C_2$—$C_{50}$alkyl substituted by one or more of the groups methyl, ethyl, OH, $NH_2$, and is interrupted by one or more oxygen, —NH—, cyclohexanediyl, norbornanediyl or phenylene, or $R_8$ and $R_9$ together are unbranched or branched $C_3$-$C_9$alkylene which may be interrupted by —O— or by —N($R_{15}$)—;

$R_{10}$ is hydrogen, —Si($C_1$-$C_6$alkyl)$_3$, $C_1$-$C_8$alkyl, $C_3$-$C_6$alkenyl or benzyl, $R_{11}$ and $R_{12}$ are each independently of the other $C_1$-$C_{12}$alkyl; $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl, or $R_{11}$ and $R_{12}$ together are unbranched or branched $C_3$-$C_9$alkylene which may be interrupted by —O— or by —N($R_{15}$)—;

$R_{13}$ and $R_{14}$ are each independently of the other hydrogen, $C_1$-$C_{12}$alkyl; $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl, or $R_{13}$ and $R_{14}$ together are unbranched or branched $C_3$-$C_9$alkylene which may be interrupted by —O— or by —N($R_{15}$)—;

$R_{15}$ is hydrogen, $C_1$-$C_4$alkyl, allyl, benzyl, $C_1$-$C_4$hydroxyalkyl, —$CH_2CH_2$—COO($C_1$-$C_4$alkyl) or —$CH_2CH_2CN$;

$R_{16}$ is $C_1$-$C_4$alkyl, hydroxyethyl, 2,3-dihydroxypropyl, cyclohexyl, benzyl, phenyl, $C_1$-$C_{12}$alkylphenyl, —$CH_2$—COO($C_1$-$C_{18}$alkyl), —$CH_2CH_2$—COO($C_1$-$C_{18}$alkyl) or —CH($CH_3$)—COO($C_1$-$C_{18}$alkyl);

$R_{17}$ and $R_{18}$ are each independently of the other a monovalent radical methyl, —O—Si($CH_3$)$_3$, —O—Si($CH_3$)$_2$—O—Si($CH_3$)$_3$, O—Si($CH_3$)[—($CH_2$)$_p$—OH]—O—Si($CH_3$) or a bivalent radical —O—Si($CH_3$)$_2$—, —O—Si($CH_3$)[—($CH_2$)$_p$—OH]—, —O—Si($CH_3$)($R_{19}$)—, —O—Si($CH_3$)($R_{20}$)— and form chains;

$R_{19}$ and $R_{20}$ are each independently of the other a monovalent radical methyl, —O—Si($CH_3$)$_3$, —O—Si($CH_3$)$_2$—O—Si($CH_3$)$_3$, —O—Si($CH_3$)[—($CH_2$)$_p$—OH]—O—Si($CH_3$) or a bivalent radical —O—Si($CH_3$)$_2$—, —O—Si($CH_3$)[—($CH_2$)$_p$—OH]—, —O—Si($CH_3$)($R_{19}$)—, —O—Si($CH_3$)($R_{20}$)— and extend chains and, when $R_{19}$ and $R_{20}$ are linked into a ring, —($R_{19}$)—($R_{20}$)— is the bridge —O—;

$R_{21}$ is, independently of formula I, a radical

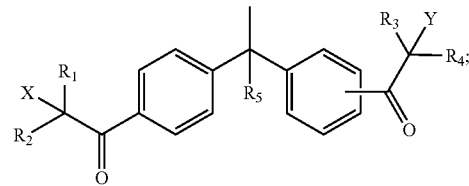

p is an integer from 2 to 12, preferably 3, 5 or 6, it being possible for the carbon chain of the alkylene to be interrupted by from one to three oxygen atoms.

Alkyl may be unbranched or branched alkyl.

$C_3$-$C_6$Alkenyl is, for example, allyl, methallyl or 2-butenyl.

When $R_1$ and $R_2$ together and/or $R_3$ and $R_4$ together are $C_3$-$C_6$-oxa- or -aza-alkylene, there is formed, for example, an aziridine, azetidine, pyrrolidine, imidazolidine, piperidine, piperazine or morpholine ring.

$C_2$-$C_{18}$Acyl is, for example, acetyl, propanoyl, butanoyl, 2-methylpropanoyl, butanoyl to octadecanoyl.

Hydroxyalkyl is alkyl substituted by hydroxy.

Hydroxyalkyl interrupted by from one to nine oxygen atoms is, for example, —($CH_2$)$_a$—O—($CH_2$)$_b$—OH.

Preferred compounds:

Novel Photoinitiators of Formula III or IV

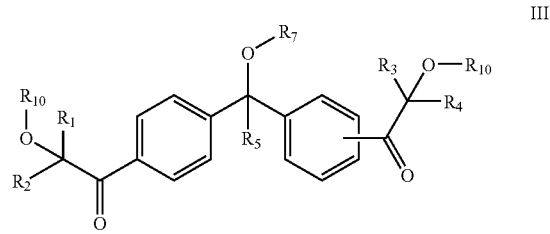

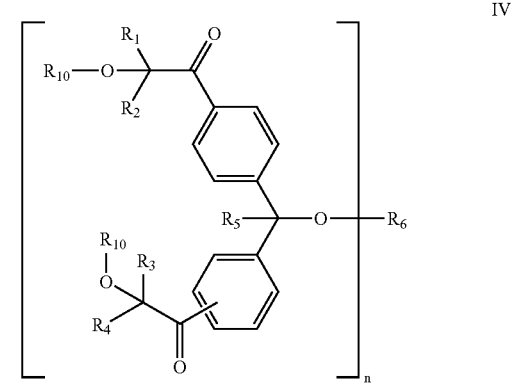

wherein $R_1$, $R_2$, $R_3$ and $R_4$ are each independently of the others $C_1$-$C_8$alkyl, $C_3$-$C_6$alkenyl, benzyl, —$CH_2$—$C_6H_4$—($C_1$-$C_4$alkyl) or phenyl, or $R_1$ and $R_2$ together and/or $R_3$ and $R_4$ together are unbranched or branched $C_2$-$C_9$alkylene;

$R_5$ is hydrogen, $C_1$-$C_8$alkyl, $C_3$-$C_6$alkenyl, benzyl, —$CH_2$—$C_6H_4$—($C_1$-$C_4$alkyl) or phenyl;

n is an integer from 1 to 10, preferably an integer from 1 to 4, especially 1, 2 or 3; and R₆ is an n-valent radical of linear or branched C₂-C₂₀alkyl the carbon chain of which may be interrupted by cyclohexanediyl, phenylene, —CH(OH)—, —C(C₂H₅)(CH₂—CH₂—OH)—, —C(CH₃)(CH₂—CH₂—OH)—, —C(CH₂—CH₂—OH)₂—, —N(CH₃)—, —N(C₂H₅)—, —N(CH₂—CH₂—OH)—, —CO—O—, —O—CO—, —P(CH₂—CH₂—OH)—, —P(O)(CH₂—CH₂—OH), —O—P(O—CH₂—CH₂—OH)—O—, —O—P(O)(O—CH₂—CH₂—OH)—O—, —O-cyclohexanediyl-C(CH₃)₂-cyclohexanediyl-O—, —O-phenylene-C(CH₃)₂-phenylene-O—, —O-phenylene-CH₂-phenylene-O—, —Si(CH₃)₂—, —O—Si(CH₃)₂—O—, —O—Si(CH₃)(O—CH₃)—O—, —Si(CH₃)(R₁₇)—O—Si(CH₃)(R₁₈), 5-(2-hydroxy-ethyl)-[1,3,5]triazinane-2,4,6-trione-1,3-diyl and/or by from one to nine oxygen atoms, or R₆ is an n-valent radical of linear or branched —CO—NH—(C₂-C₉alkylene)-(NH—CO)_{n-1}— or linear or branched —CO—NH—(C₀-C₉alkylene)-(NH—CO)_{n-1}— which may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl, 5-(6-isocyanatohexyl)-[1,3,5]triazinane-2,4,6-trione-1,3-diyl or 3-(6-isocyanatohexyl)-biuret-1,5-diyl radical(s), or R₆ is an n-valent radical of linear or branched —CO—(C₀-C₁₂alkylene)-(CO)_{n-1}— and the alkylene may be interrupted by oxygen, phenylene, cyclohexanediyl or by norbornane-diyl;

R₇ is hydrogen, —Si(C₁-C₆alkyl)₃, C₁-C₁₂alkyl, R₂₁, C₂-C₁₈acyl, —CO—NH—C₁-C₁₂alkyl, C₂-C₂₀hydroxyalkyl, C₂-C₂₀methoxyalkyl, 3-(C₁-C₁₈alkoxy)-2-hydroxy-propyl, 3-[1,3,3,3-tetramethyl-1-[(trimethylsilyl)oxy]disiloxanyl]-propyl, 2,3-dihydroxypropyl or linear or branched C₂-C₂₁hydroxyalkyl or (C₁-C₄alkoxy)-C₂-C₂₁alkyl the carbon chain of which is interrupted by from one to nine oxygen atoms;

R₁₀ is hydrogen, —Si(C₁-C₆alkyl)(CH₃)₂, C₁-C₈alkyl, C₃-C₆alkenyl or benzyl;

R₁₇ and R₁₈ are each independently of the other a monovalent radical methyl, —O—Si(CH₃)₃, —O—Si(CH₃)₂—O—Si(CH₃)₃, —O—Si(CH₃)[—(CH₂)_p—OH]—O—Si(CH₃) or a bivalent radical —O—Si(CH₃)₂—, —O—Si(CH₃)[—(CH₂)_p—OH]—, —O—Si(CH₃)(R₁₉)—, —O—Si(CH₃)(R₂₀)— and form chains;

R₁₉ and R₂₀ are each independently of the other a monovalent radical methyl, —O—Si(CH₃)₃, —O—Si(CH₃)₂—O—Si(CH₃)₃, —O—Si(CH₃)[—(CH₂)_p—OH]—O—Si(CH₃) or a bivalent radical —O—Si(CH₃)₂—, —O—Si(CH₃)[—(CH₂)_p—OH]—, —O—Si(CH₃)(R₁₉)—, —O—Si(CH₃)(R₂₀)— and extend chains and, when R₁₉ and R₂₀ are linked into a ring, —(R₁₉)—(R₂₀)— is the bridge —O—;

R₂₁ is, independently of formula III, a radical

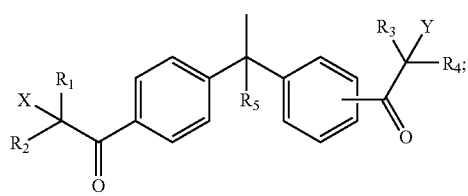

p is an integer from 2 to 12, preferably 3, 5 or 6, it being possible for the carbon chain of the alkylene to be interrupted by from one to three oxygen atoms.

Novel photoinitiators of formula V

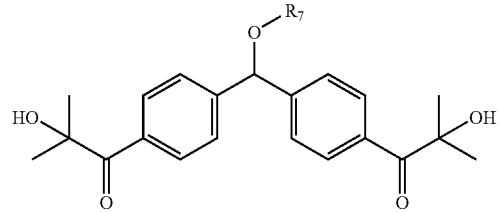

wherein

R₇ is hydrogen, —Si(CH₃)₃, C₁-C₈alkyl, bis[4-(2-hydroxy-2-methyl-propionyl)-phenyl]-methyl, C₂-C₁₈acyl, —CO—NH—C₁-C₈alkyl, C₂-C₂₀hydroxyalkyl, C₂-C₂₀methoxyalkyl or C₂-C₂₀hydroxyalkyl the carbon chain of which is interrupted by from one to nine oxygen atoms.

Novel Photoinitiators of Formulae VI, VII and VIII

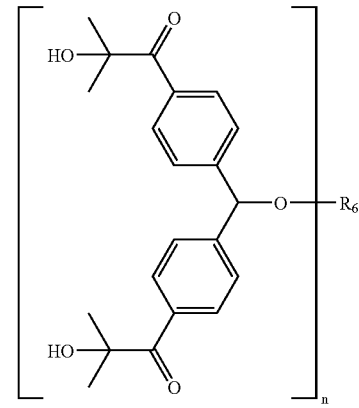

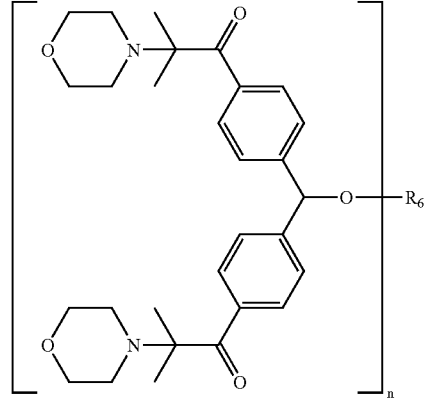

-continued

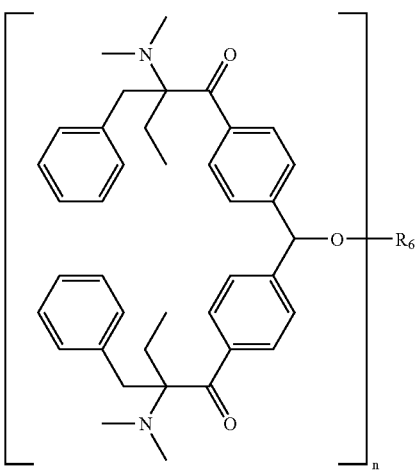

VIII wherein n is an integer from 1 to 4, preferably an integer from 1 to 3, especially 2, and $R_6$ is an n-valent radical of linear or branched $C_2$-$C_{16}$alkyl the carbon chain of which may be interrupted by cyclohexanediyl, phenylene, —CH(OH)—, —C(CH$_2$—CH$_2$—OH)$_2$—, —C(CH$_3$)(CH$_2$—CH$_2$—OH)—, —C(C$_2$H$_5$)(CH$_2$—CH$_2$—OH)—, —N(CH$_3$)—, —N(CH$_2$—CH$_2$—OH)—, —CO—O—, —O—CO—, —Si(CH$_3$)$_2$—, —Si(CH$_3$)(R$_{17}$)—O—Si(CH$_3$)(R$_{18}$)—, —O—Si(CH$_3$)$_2$—O—, —O—Si(CH$_3$)(O—CH$_3$)—O—, 5-(2-hydroxyethyl)-[1,3,5]triazinane-2,4,6-trione-1,3-diyl and/or by from one to six oxygen atoms, or $R_6$ is an n-valent radical of linear or branched —CO—NH—(C$_2$-C$_9$alkylene)-(NH—CO)$_{n-1}$— or linear or branched —CO—NH—(C$_0$-C$_9$alkylene)-(NH—CO)$_{n-1}$— which may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl, 5-(6-isocyanatohexyl)-[1,3,5]triazinane-2,4,6-trione-1,3-diyl or 3-(6-isocyanatohexyl)-biuret-1,5-diyl radical(s), $R_{17}$ and $R_{18}$ are each independently of the other a monovalent radical methyl, —O—Si(CH$_3$)$_3$, —O—Si(CH$_3$)$_2$—O—Si(CH$_3$)$_3$, —O—Si(CH$_3$)[—(CH$_2$)$_p$—OH]—O—Si(CH$_3$) or a bivalent radical —O—Si(CH$_3$)$_2$—, —O—Si(CH$_3$)[—(CH$_2$)$_p$—OH]—, —O—Si(CH$_3$)(R$_{19}$)—, —O—Si(CH$_3$)(R$_{20}$)— and form chains, $R_{19}$ and $R_{20}$ are each independently of the other a monovalent radical methyl, —O—Si(CH$_3$)$_3$, —O—Si(CH$_3$)$_2$—O—Si(CH$_3$)$_3$, —O—Si(CH$_3$)[—(CH$_2$)$_p$—OH]—O—Si(CH$_3$) or a bivalent radical —O—Si(CH$_3$)$_2$—, —O—Si(CH$_3$)[—(CH$_2$)$_p$—OH]—, —O—Si(CH$_3$)(R$_{19}$)—, —O—Si(CH$_3$)(R$_{20}$)— and extend chains and, when $R_{19}$ and $R_{20}$ are linked into a ring, —(R$_{19}$)—(R$_{20}$)— is the bridge —O—, p is an integer from 2 to 12, preferably 3, 5 or 6, it being possible for the carbon chain of the alkylene to be interrupted by from one to three oxygen atoms.

Novel Photoinitiators of Formula IX

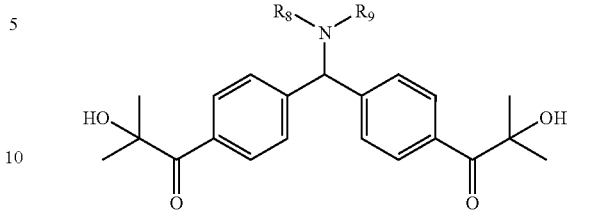

IX wherein $R_8$ and $R_9$ are each independently of the other hydrogen, $C_1$-$C_{12}$alkyl; $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl, or when $R_9$=H or methyl, $R_8$ is also $C_2$-$C_{50}$alkyl substituted by one or more of the groups methyl, ethyl, OH, NH$_2$, and is interrupted by one or more oxygen, —NH—, cyclohexanediyl, norbornanediyl or phenylene, or $R_8$ and $R_9$ together are unbranched or branched $C_3$-$C_9$alkylene which may be interrupted by —O— or by —N(R$_{15}$)—;

Novel Photoinitiators of Formula X

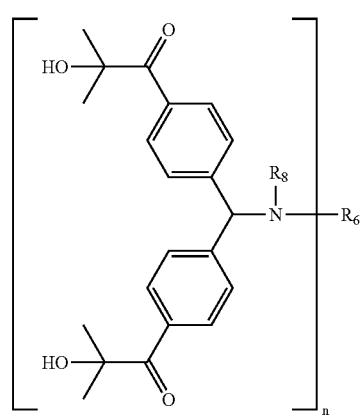

X wherein n is an integer from 1 to 4, preferably an integer from 1 to 3, especially 2, and $R_6$ is an n-valent radical of linear or branched $C_2$-$C_{16}$alkyl the carbon chain of which may be interrupted by cyclohexanediyl, phenylene, —CH(OH)—, —C(CH$_2$—CH$_2$—OH)$_2$—, —C(CH$_3$)(CH$_2$—CH$_2$—OH)—, —C(C$_2$H$_5$)(CH$_2$—CH$_2$—OH)—, —N(CH$_3$)—, —N(CH$_2$—CH$_2$—OH)—, —CO—O—, —O—CO—, —O—CO—NH, NH—CO—O—, —Si(CH$_3$)$_2$—, —Si(CH$_3$)(R$_{17}$)—O—Si(CH$_3$)(R$_{18}$)—, —O—Si(CH$_3$)$_2$—O—, —O—Si(CH$_3$)(O—CH$_3$)—O—, 5-(2-hydroxyethyl)-[1,3,5]triazinane-2,4,6-trione-1,3-diyl and/or by from one to six oxygen atoms, or $R_6$ is an n-valent radical of linear or branched —C$_2$-C$_{50}$alkylene the carbon chain of which is interrupted by one to 15 oxygen, and may be subsituted by OH or NH$_2$;

$R_8$ is hydrogen, $C_1$-$C_4$alkyl; $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl;

The radical $R_6$ is preferably prepared from alcohols from the following list:
Collection of Structures for Technical di- and oligo-alcohols
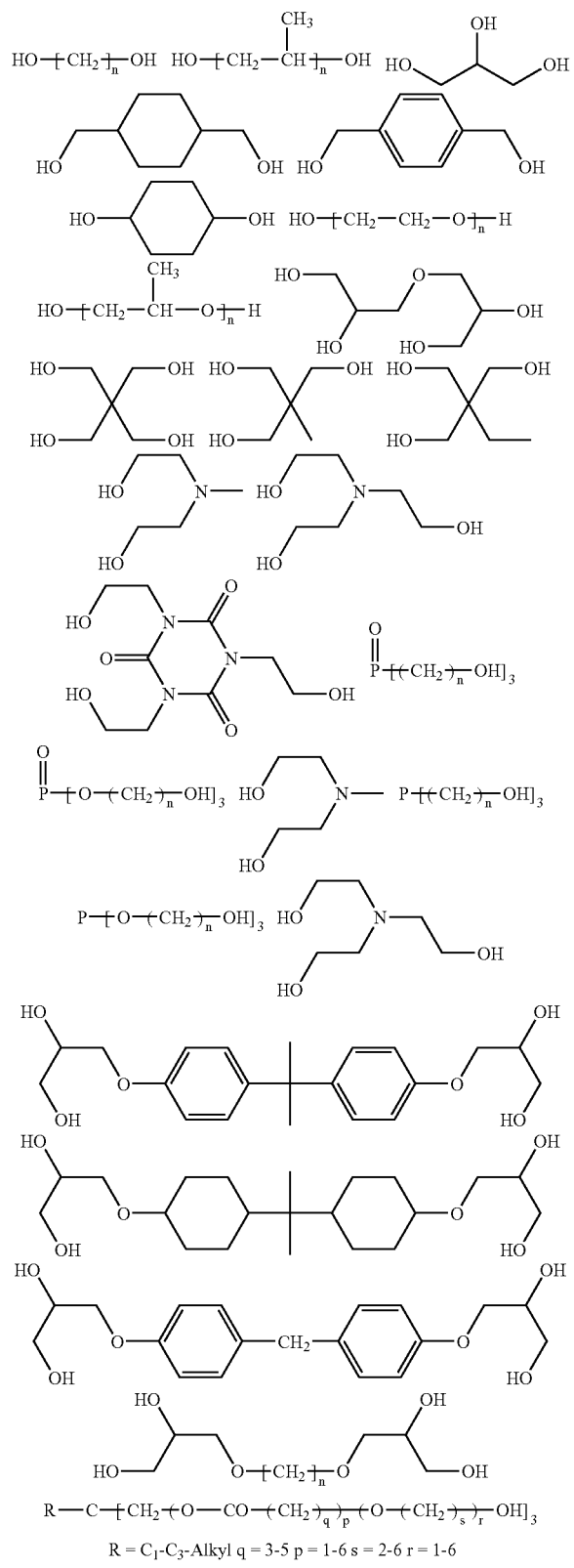
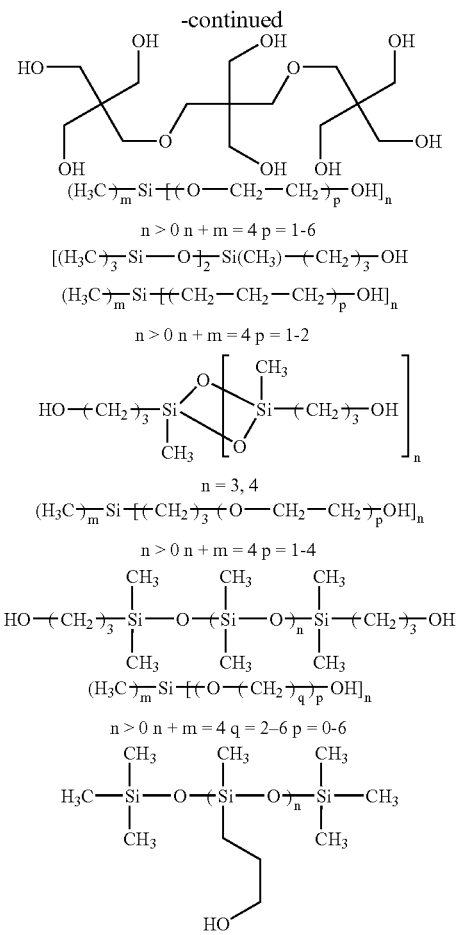
The radical $R_6$ is prepared from isocyanates from the following list:
Collection of Structures for Technical di- and oligo-isocyanates
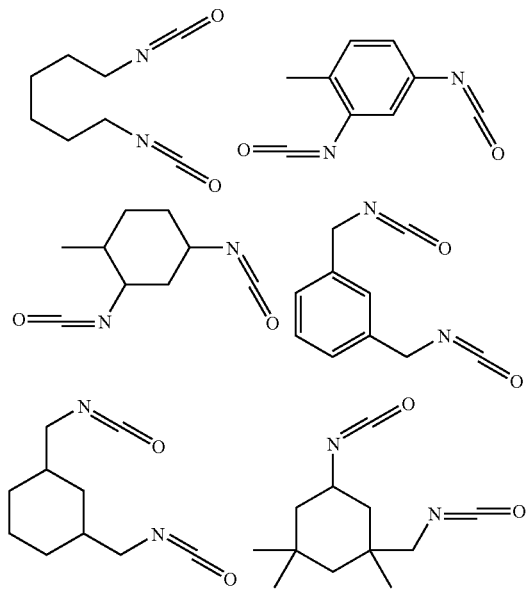

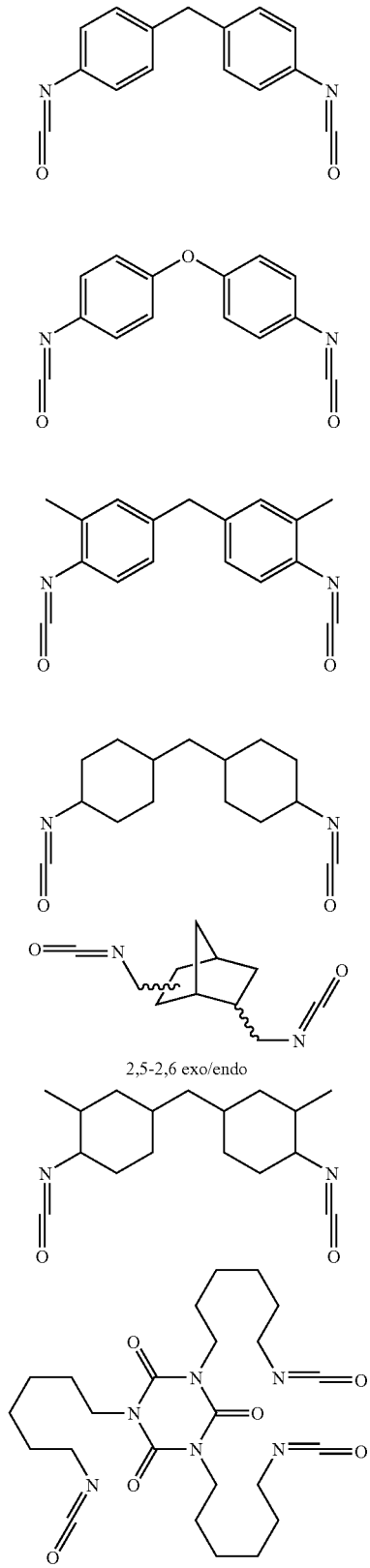

The radical $R_6$ is prepared from amines from the following list:
Collection of Structures for Technical di- and polyamines
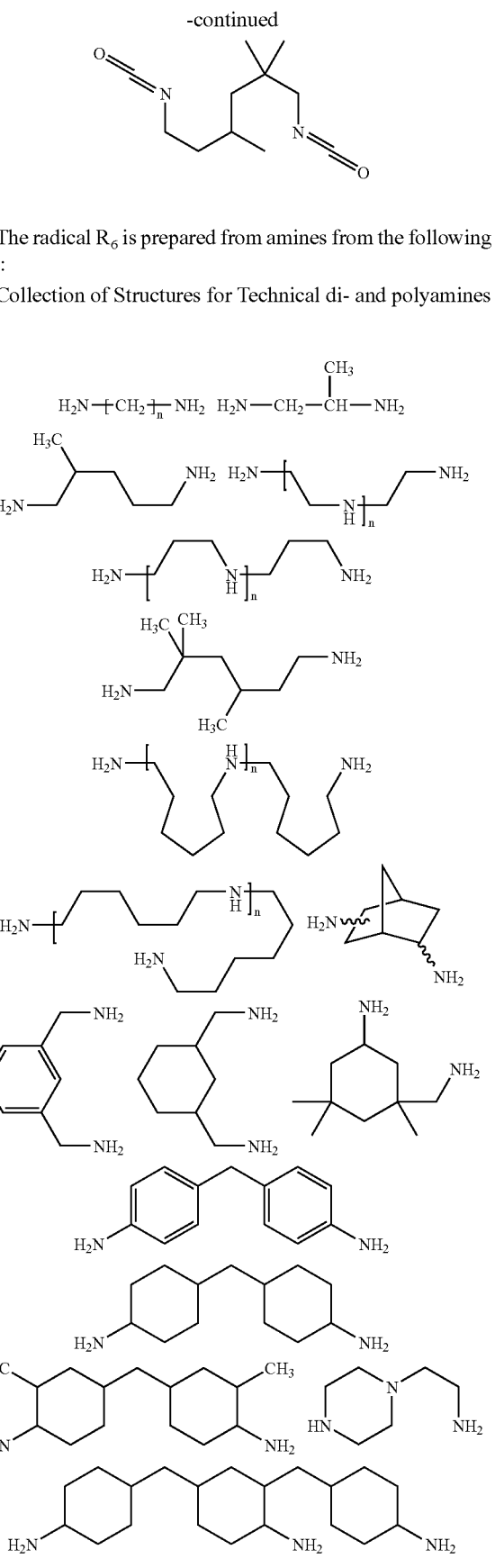
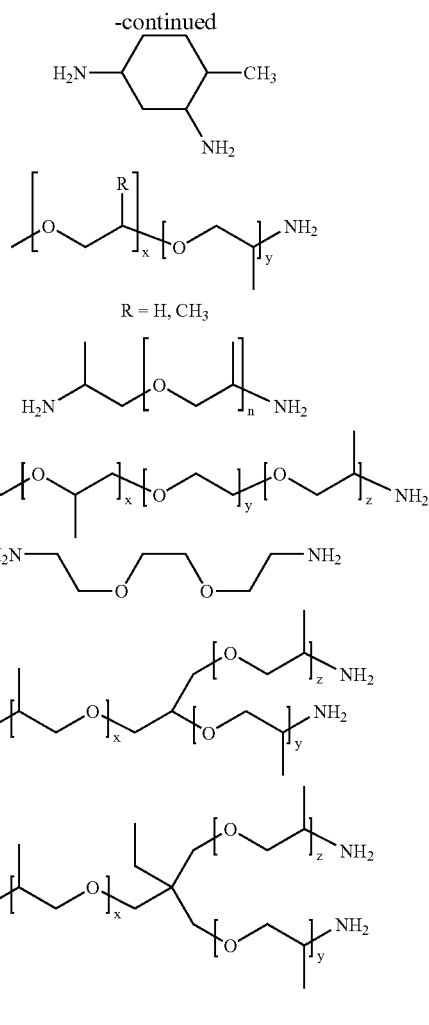
Individual Compounds:
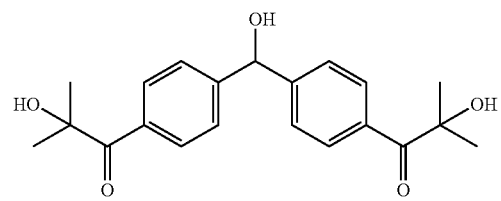
2-hydroxy-1-(4-{hydroxy-[4-(2-hydroxy-2-methyl-propionyl)-phenyl]-methyl}-phenyl)-2-methyl-propan-1-one
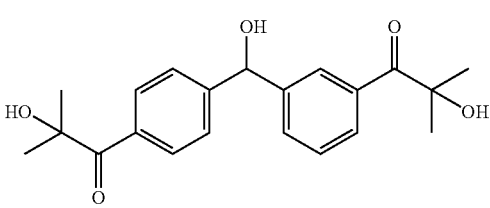
2-hydroxy-1-(3-{hydroxy-[4-(2-hydroxy-2-methyl-propionyl)-phenyl]-methyl}-phenyl)-2-methyl-propan-1-one

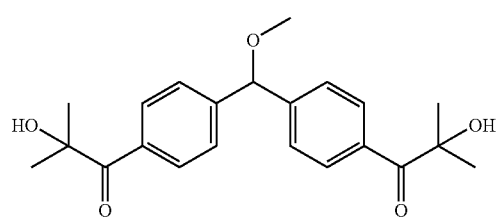

2-hydroxy-1-(4-{methoxy-[4-(2-hydroxy-2-methyl-propionyl)-phenyl]-methyl}-phenyl)-2-methyl-propan-1-one

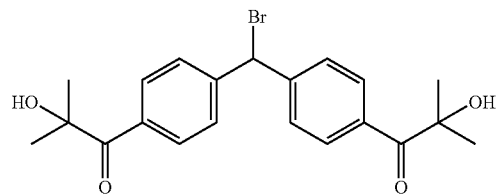

1-(4-{bromo-[4-(2-hydroxy-2-methyl-propionyl)-phenyl]-methyl}-phenyl)-2-hydroxy-2-methyl-propane-1-one

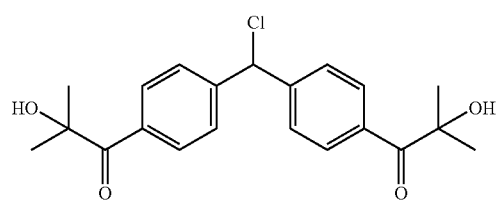

1-(4-{chloro-[4-(2-hydroxy-2-methyl-propionyl)-phenyl]-methyl}-phenyl)-2-hydroxy-2-methyl-propane-1-one

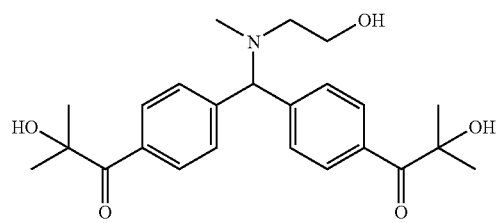

2-hydroxy-1-(4-{[(2-hydroxy-ethyl)-methyl-amino]-[4-(2-hydroxy-2-methyl-propionyl)-phenyl]-methyl}-phenyl)-2-methyl-propane-1-one

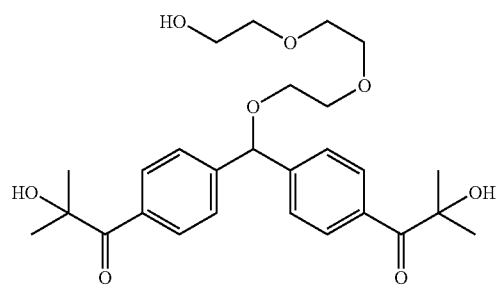

2-hydroxy-1-(4-{{2-[2-(2-hydroxy-ethoxy)-ethoxy]-ethoxy}-[4-(2-hydroxy-2-methyl-propionyl)-phenyl]-methyl}-phenyl)-2-methyl-propane-1-one.

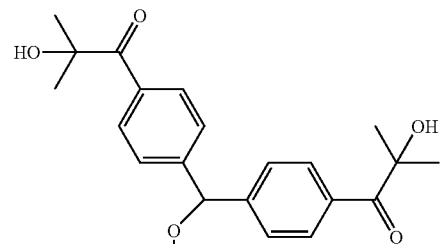

1-(4-{{bis[4-(2-hydroxy-2-methyl-propionyl)-phenyl]-methoxy}-[4-(2-hydroxy-2-methyl-propionyl)-phenyl]-methyl}-phenyl)-2-hydroxy-2-methyl-propan-1-one

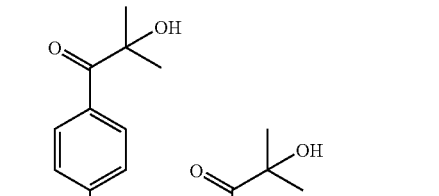

1-(4-{[2-(2{bis[4-(2-hydroxy-2-methyl-propionyl)-phenyl]-methoxy}-ethoxy)-ethoxy]-[4-(2-hydroxy-2-methyl-propionyl)-phenyl]-methyl}-phenyl)-2-hydroxy-2-methyl-propan-1-one

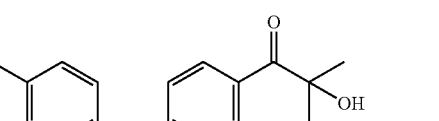

(6-{bis[4-(2-hydroxy-2-methyl-propionyl)-phenyl]-methoxycarbonylamino}-hexyl)-carbamic acid bis[4-(2-hydroxy-2-methyl-propionyl)-phenyl]-methyl ester

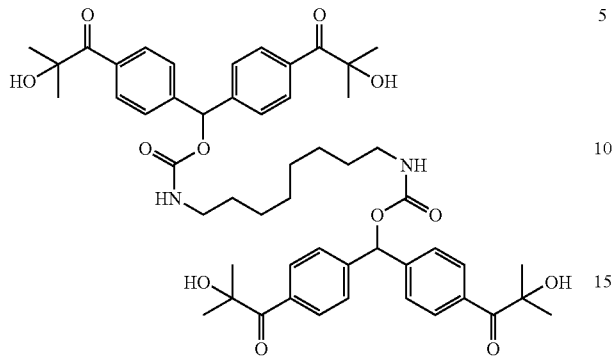

(8-{bis-[4-(2-hydroxy-2-methyl-propionyl)-phenyl]-methoxycarbonylamino}-octyl)-carbamine acid-bis-[4-(2-hydroxy-2-methyl-propionyl)-phenyl]-methylester

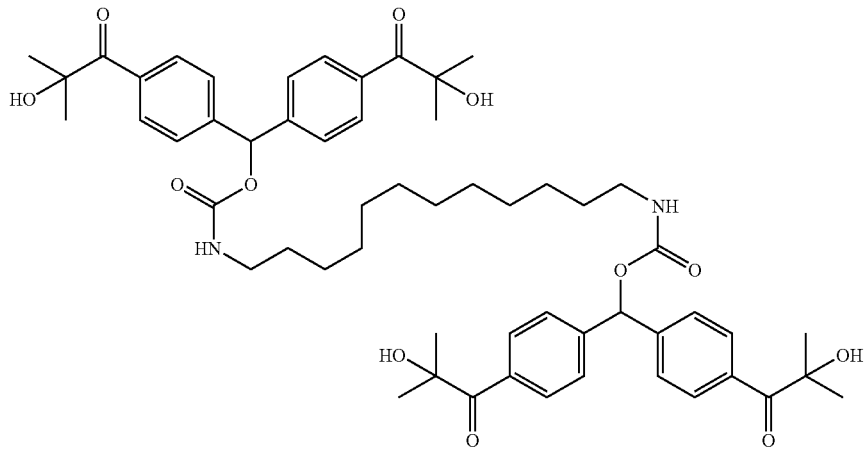

(12-{bis-[4-(2-hydroxy-2-methyl-propionyl)-phenyl]-methoxycarbonylamino}-dodecyl)-carbamine acid-bis-[4-(2-hydroxy-2-methyl-propionyl)-phenyl]-methylester

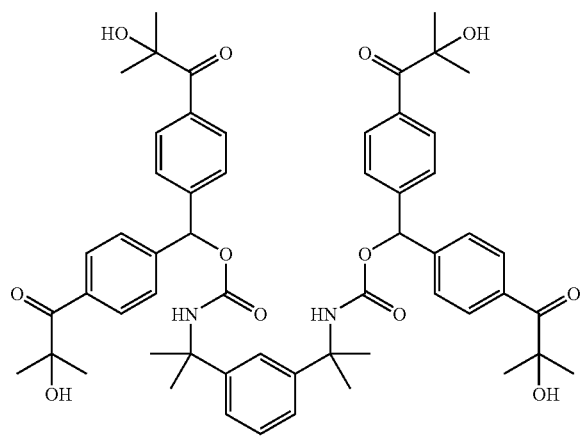

{1-[3-(1-{bis-[4-(2-hydroxy-2-methyl-propionyl)-phenyl]-methoxycarbonylamino}-1-methyl-ethyl)-phenyl]-1-methyl-ethyl}-carbamine acid-bis-[4-(2-hydroxy-2-methyl-propionyl)-phenyl]-methylester

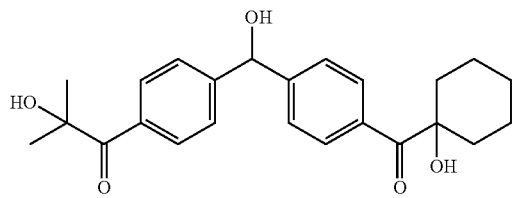

2-hydroxy-1-(4-{hydroxy-[4-(1-hydroxy-cyclohexanecarbonyl)-phenyl]-methyl}-phenyl)-2-methyl-propane-1-one.

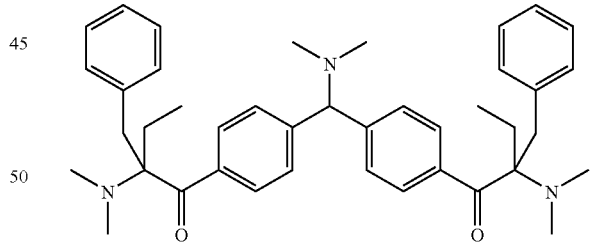

2-benzyl-1-(4-{[4-(2-benzyl-2-dimethylamino-butyryl)-phenyl]-dimethylamino-methyl}-phenyl)-2-dimethylamino-butane-1-one.

Examples of compounds of formula I are:

2-hydroxy-1-(4-hydroxy-[4-(2-hydroxy-2-methyl-propionyl)-phenyl]-methyl)-phenyl)-2-methyl-propan-1-one 2-hydroxy-1-(3-{hydroxy-[4-(2-hydroxy-2-methyl-propionyl)-phenyl]-methyl}-phenyl)-2-methyl-propan-1-one 2-hydroxy-1-(2-{hydroxy-[4-(2-hydroxy-2-methyl-propionyl)-phenyl]-methyl}-phenyl)-2-methyl-propan-1-one 2-hydroxy-1-(4-{methoxy-[4-(2-hydroxy-2-methyl-propionyl)-phenyl]-methyl}-phenyl)-2-methyl-propan-1-one 2-hydroxy-1-(3-{[4-(2-hydroxy-2-methyl-propionyl)-phenyl]-methoxy-methyl}-phenyl)-2-methyl-propan-1-one
1-(4-{ethoxy-[4-(2-hydroxy-2-methyl-propionyl)phenyl]-methyl}-phenyl)-2-hydroxy-2-methyl-propan-1-one
2-hydroxy-1-(4-{[4-(2-hydroxy-2-methyl-propionyl)-phenyl]-isopropoxy-methyl}-phenyl)-2-methyl-propan-1-one
1-(4-{dodecyloxy-[4-(2-hydroxy-2-methyl-propionyl)-phenyl]-methyl}-phenyl)-2-hydroxy-2-methyl-propan-1-one
1-(4-{allyloxy-[4-(2-hydroxy-2-methyl-propionyl)-phenyl]-methyl}-phenyl)-2-hydroxy-2-methyl-propan-1-one
1-(4-{benzyloxy-[4-(2-hydroxy-2-methyl-propionyl)-phenyl]-methyl}-phenyl)-2-hydroxy-2-methyl-propan-1-one
2-hydroxy-1-(4-{(2-hydroxy-ethoxy)-[4-(2-hydroxy-2-methyl-propionyl)-phenyl]-methyl}-phenyl)-2-methyl-propan-1-one
2-hydroxy-1-{4-[[4-(2-hydroxy-2-methyl-propionyl)-phenyl]-(2-methoxy-ethoxy)-methyl]-phenyl}-2-methyl-propan-1-one
1-(4-{2-butoxy-ethoxy)-[4-(2-hydroxy-2-methyl-propionyl)-phenyl]-methyl}-phenyl)-2-hydroxy-2-methyl-propan-1-one
2-hydroxy-1-(4-{[2-(2-hydroxy-ethoxy)-ethoxy]-[4-(2-hydroxy-2-methyl-propionyl)-phenyl]-methyl}-phenyl)-2-methyl-propan-1-one
2-hydroxy-1-(4-{{2-[2-(2-hydroxy-ethoxy)-ethoxy]-ethoxy}-[4-(2-hydroxy-2-methyl-propionyl)-phenyl]-methyl}-phenyl)-2-methyl-propan-1-one
2-hydroxy-1-(4-{(2-{2-[2-(2-hydroxy-ethoxy)-ethoxy]-ethoxy}-ethoxy)-[4-(2-hydroxy-2-methyl-propionyl)-phenyl]-methyl}-phenyl)-2-methyl-propan-1-one
2-hydroxy-1-(4-{[2-(2-{2-[2-(2-hydroxy-ethoxy)-ethoxy]-ethoxy}-ethoxy)-ethoxy]-[4-(2-hydroxy-2-methyl-propionyl)-phenyl]-methyl}-phenyl)-2-methyl-propan-1-one
2-hydroxy-1-{4-[[4-(2-hydroxy-2-methyl-propionyl)-phenyl]-(2-hydroxy-propoxy)-methyl]-phenyl}-2-methyl-propan-1-one
2-hydroxy-1-{4-[[4-(2-hydroxy-2-methyl-propionyl)-phenyl]-(5-hydroxy-pentyloxy)-methyl]-phenyl}-2-methyl-propan-1-one
2-hydroxy-1-(4-{(6-hydroxy-hexyloxy)-[4-(2-hydroxy-2-methyl-propionyl)-phenyl]-methyl}-phenyl)-2-methyl-propan-1-one
1-(4-{dodecyloxy-[4-(2-hydroxy-2-methyl-propionyl)-phenyl]-methyl}-phenyl)-2-hydroxy-2-methyl-propan-1-one
1-{(2,3-dihydroxy-propoxy)-[4-(2-hydroxy-2-methyl-propionyl)-phenyl]-methyl}-phenyl)-2-hydroxy-2-methyl-propan-1-one
1-(4-{(3-butoxy-2-hydroxy-propoxy)-[4-(2-hydroxy-2-methyl-propionyl)-phenyl]-methyl}-phenyl)-2-hydroxy-2-methyl-propan-1-one
2-hydroxy-1-{4-[[4-(2-hydroxy-2-methyl-propionyl)-phenyl]-(2-hydroxy-3-octadecyloxy-propoxy)-methyl]-phenyl}-2-methyl-propan-1-one
2-hydroxy-1-[4-([4-(2-hydroxy-2-methyl-propionyl)-phenyl]-{2-[2-(2-{2-[2-(2-hydroxy-propoxy)-propoxy]-propoxy}-propoxy)-propoxy]-propoxy}-methyl)-phenyl]-2-methyl-propan-1-one
1-(4-{{bis[4-(2-hydroxy-2-methyl-propionyl)-phenyl]-methoxy}-[4-(2-hydroxy-2-methyl-propionyl)-phenyl]-methyl}-phenyl)-2-hydroxy-2-methyl-propan-1-one
1-(3-{{bis[4-(2-hydroxy-2-methyl-propionyl)-phenyl]-methoxy}-[4-(2-hydroxy-2-methyl-propionyl)-phenyl]-methyl}-phenyl)-2-hydroxy-2-methyl-propan-1-one
2-hydroxy-1-[3-([4-(2-hydroxy-2-methyl-propionyl)-phenyl]-{[3-(2-hydroxy-2-methyl-propionyl)-phenyl]-[4-(2-hydroxy-2-methyl-propionyl)-phenyl]-methoxy}-methyl)-phenyl]-2-methyl-propan-1-one
2-hydroxy-1-[4-([4-(2-hydroxy-2-methyl-propionyl)-phenyl]-{[2-(2-hydroxy-2-methyl-propionyl)-phenyl]-[4-(2-hydroxy-2-methyl-propionyl)-phenyl]-methoxy}-methyl)-phenyl]-2-methyl-propan-1-one
2-hydroxy-1-(4-{[4-(2-hydroxy-2-methyl-propionyl)-phenyl]-trimethylsilanyloxy-methyl}-phenyl)-2-methyl-propan-1-one
2-hydroxy-1-(4-{[4-(2-hydroxy-2-methyl-propionyl)-phenyl]-triethylsilanyloxy-methyl}-phenyl)-2-methyl-propan-1-one
1-(4-{[dimethyl-(1,1,2-trimethyl-propyl)-silanyloxy]-[4-(2-hydroxy-2-methyl-propionyl)-phenyl]-methyl}-phenyl)-2-hydroxy-2-methyl-propan-1-one
2-hydroxy-1-{4-[[4-(2-hydroxy-2-methyl-propionyl)-phenyl]-(3-{1,3,3,3-tetramethyl-1-[(trimethylsilyl)oxy]disiloxanyl}-propoxy)-methyl]-phenyl}-2-methyl-propan-1-one
2-hydroxy-1-{4-[[4-(2-hydroxy-2-methyl-propionyl)-phenyl]-(2-{3-{1,3,3,3-tetramethyl-1-[(trimethylsilyl)oxy]disiloxanyl}-propoxy}-ethoxy)-methyl]-phenyl}-2-methyl-propan-1-one
acetic acid bis[4-(2-hydroxy-2-methyl-propionyl)-phenyl]-methyl ester
acetic acid [4-(2-acetoxy-2-methyl-propionyl)-phenyl]-[4-(2-hydroxy-2-methyl-propionyl)-phenyl]-methyl ester
isobutyric acid bis[4-(2-hydroxy-2-methyl-propionyl)-phenyl]-methyl ester
stearic acid bis[4-(2-hydroxy-2-methyl-propionyl)-phenyl]-methyl ester
lauric acid [4-(2-hydroxy-2-methyl-propionyl)-phenyl]-[3-(2-hydroxy-2-methyl-propionyl)-phenyl]-methyl ester
hexylcarbamic acid bis[4-(2-hydroxy-2-methyl-propionyl)-phenyl]-methyl ester
dodecylcarbamic acid bis[4-(2-hydroxy-2-methyl-propionyl)-phenyl]-methyl ester
toluene-4-sulfonic acid bis[4-(2-hydroxy-2-methyl-propionyl)-phenyl]-methyl ester
1-(4-{bromo-[4-(2-hydroxy-2-methyl-propionyl)-phenyl]-methyl}-phenyl)-2-hydroxy-2-methyl-propan-1-one
1-(4-{chloro-[4-(2-hydroxy-2-methyl-propionyl)-phenyl]-methyl}phenyl)-2-hydroxy-2-methyl-propan-1-one
2-hydroxy-1-(4-{hydroxy-[4-(1-hydroxy-cyclohexanecarbonyl)-phenyl]-methyl}-phenyl)-2-methyl-propan-1-one
(1-hydroxy-cyclohexyl)-(4-{hydroxy-[4-(1-hydroxy-cyclohexanecarbonyl)-phenyl]-methyl}-phenyl)-methanone
2-ethyl-1-(4-{[4-(2-ethyl-2-hydroxy-hexanoyl)-phenyl]-hydroxy-methyl}-phenyl)-2-hydroxy-hexan-1-one
1-(4-{hydroxy-[4-(2-hydroxy-2-methyl-propionyl)-phenyl]-methyl}-phenyl)-2-methyl-2-morpholin-4-yl-propan-1-one
1-(4-{hydroxy-[4-(2-methyl-2-morpholin-4-yl-propionyl)-phenyl]-methyl}-phenyl)-2-methyl-2-morpholin-4-yl-propan-1-one
2-hydroxy-1-(4-{methoxy-[4-(2-methyl-2-morpholin-4-yl-butyryl)-phenyl]-methyl}-phenyl)-2-methyl-butan-1-one
2-methyl-1-(4-{[4-(2-methyl-2-morpholin-4-yl-propionyl)-phenyl]-morpholin-4-yl-methyl}-phenyl)-2-morpholin-4-yl-propan-1-one
2-benzyl-1-(4-{[4-(2-benzyl-2-dimethylamino-butyryl)-phenyl]-hydroxy-methyl}-phenyl)-2-dimethylamino-butan-1-one
2-benzyl-1-(4-{[4-(2-benzyl-2-dimethylamino-butyryl)-phenyl]-dimethylamino-methyl}-phenyl)-2-dimethylamino-butan-1-one 2-dimethylamino-1-[4-({4-[2-dimethylamino-2-(4-methyl-benzyl)-butyryl]-phenyl}-hydroxy-methyl)-phenyl]-2-(4-methyl-benzyl)-butan-1-one 2-ethyl-1-(4-{[4-(2-ethyl-2-morpholin-4-yl-pent-4-enoyl)-phenyl]-hydroxy-methyl}-phenyl)-2-morpholin-4-yl-pent-4-en-1-one 2-dimethylamino-1-(4-{[4-(2-dimethylamino-2-ethyl-pent-4-enoyl)-phenyl]-hydroxy-methyl}-phenyl)-2-ethyl-pent-4-en-1-one 2-dimethylamino-1-(4-{[4-(2-dimethylamino-2-ethyl-pentanoyl)-phenyl]-hydroxy-methyl}-phenyl)-2-ethyl-pentan-1-one 2-dimethylamino-1-(4-{[4-(2-dimethylamino-2-methyl-propionyl)-phenyl]-hydroxy-methyl}-phenyl)-2-methyl-propan-1-one 2-dimethylamino-1-(4-{[4-(2-dimethylamino-2-methyl-propionyl)-phenyl]-methoxy-methyl}-phenyl)-2-methyl-propan-1-one 2-dimethylamino-1-(4-{dimethylamino-[4-(2-dimethylamino-2-methyl-propionyl)-phenyl]-methyl}-phenyl)-2-methyl-propan-1-one 2-[bis(2-methoxy-ethyl)-amino]-1-{4-[(4-{2-[bis-(2-methoxy-ethyl)-amino]-2-methyl-propionyl}-phenyl)-hydroxy-methyl]-phenyl}-2-methyl-propan-1-one 2-dibutylamino-1-(4-{[4-(2-dibutylamino-2-methyl-propionyl)-phenyl]-hydroxy-methyl}-phenyl)-2-methyl-propan-1-one 2-dibutylamino-1-(4-{[4-(2-dibutylamino-2-methyl-propionyl)-phenyl]-methoxy-methyl}-phenyl)-2-methyl-propan-1-one 2-[bis(2-methoxy-ethyl)-amino]-1-{4-[(4-{2-[bis(2-methoxy-ethyl)-amino]-2-methyl-propionyl}-phenyl)-methoxy-methyl]-phenyl}-2-methyl-propan-1-one 1-(4-{methoxy-[4-(2-methyl-2-piperidin-1-yl-propionyl)-phenyl]-methyl}-phenyl)-2-methyl-2-piperidin-1-yl-propan-1-one 1-[4-(hydroxy-{4-[2-methyl-2-(4-methyl-piperazin-1-yl)-propionyl]-phenyl}methyl)-phenyl]-2-methyl-2-(4-methyl-piperazin-1-yl)-propan-1-one 2-hydroxy-1-{3-[[4-(2-hydroxy-2-methyl-propionyl)-phenyl]-({[4-(2-hydroxy-2-methyl-propionyl)-phenyl]-[3-(2-hydroxy-2-methyl-propionyl)-phenyl]-methyl}-amino)-methyl]-phenyl}-2-methyl-propan-1-one 2-hydroxy-1-{3-[[4-(2-hydroxy-2-methyl-propionyl)-phenyl]-({[4-(2-hydroxy-2-methyl-propionyl)-phenyl]-[3-(2-hydroxy-2-methyl-propionyl)-phenyl]-methyl}-methyl-amino)-methyl]-phenyl}-2-methyl-propan-1-one 2-dimethylamino-1-(4-{({[4-(2-dimethylamino-2-methyl-propionyl)-phenyl]-[4-(2-hydroxy-2-methyl-propionyl)-phenyl]-methyl}-methyl-amino)-[3-(2-hydroxy-2-methyl-propionyl)-phenyl]-methyl}-phenyl)-2-methyl-propan-1-one 1-[3-({4-[2-(2,6-dimethyl-morpholin-4-yl)-2-methyl-propionyl]-phenyl}-{{4-[2-(2,6-dimethyl-morpholin-4-yl)-2-methyl-propionyl]-phenyl}-[3-(2-hydroxy-2-methyl-propionyl)-phenyl]-methoxy}-methyl)-phenyl]-2-hydroxy-2-methyl-propan-1-one 2-methoxy-1-(4-{methoxy-[4-(2-methoxy-2-methyl-propionyl)-phenyl]-methyl}-phenyl)-2-methyl-propan-1-one 2-methoxy-1-(4-{1-methoxy-1-[4-(2-methoxy-2-methyl-propionyl)-phenyl]-ethyl}-phenyl)-2-methyl-propan-1-one 2-allyloxy-1-(4-{allyoxy-[4-(2-allyloxy-2-methyl-propionyl)-phenyl]-methyl}-phenyl)-2-methyl-propan-1-one 2-allyloxy-1-(4-{1-allyloxy-1-[4-(2-allyloxy-2-methyl-propionyl)-phenyl]-but-3-enyl}-phenyl)-2-methyl-propan-1-one 2-methyl-1-(4-{1-[4-(2-methyl-2-propoxy-propionyl)-phenyl]-1-propoxy-butyl}-phenyl)-2-propoxy-propan-1-one 2-benzyloxy-1-(4-{benzyloxy-[4-(2-benzyloxy-2-methyl-propionyl)-phenyl]-methyl}-phenyl)-2-methyl-propan-1-one 2-benzyloxy-1-(4-{1-benzyloxy-1-[4-(2-benzyloxy-2-methyl-propionyl)-phenyl]-2-phenyl-ethyl}-phenyl)-2-methyl-propan-1-one 2-benzyl-1-(4-{[4-(2-benzyl-2-dimethylamino-butyryl)-phenyl]-benzyloxy-methyl}-phenyl)-2-dimethylamino-butan-1-one 2-dimethylamino-1-[4-(dimethylamino-{4-[2-dimethylamino-2-(4-methyl-benzyl)-butyryl]-phenyl}-methyl)-phenyl]-2-(4-methyl-benzyl)-butan-1-one 2-ethyl-1-(4-{1-[4-(2-ethyl-2-morpholin-4-yl-pent-4-enoyl)-phenyl]-1-hydroxy-but-3-enyl}-phenyl)-2-morpholin-4-yl-pent-4-en-1-one 1-(4-{1-hydroxy-1-[4-(2-methyl-2-morpholin-4-yl-propionyl)-phenyl]-ethyl}-phenyl)-2-methyl-2-morpholin-4-yl-propan-1-one 2-hydroxy-1-(4-{hydroxy-[4-(2-hydroxy-2-methyl-propionyl)-phenyl]-phenyl-methyl}-phenyl)-2-methyl-propan-1-one 2-hydroxy-1-(4-{[4-(2-hydroxy-2-methyl-propionyl)-phenyl]-octylsulfanyl-methyl}-phenyl)-2-methyl-propan-1-one 1-(4-{dodecylsulfanyl-[4-(2-hydroxy-2-methyl-propionyl)-phenyl]-methyl}-phenyl)-2-hydroxy-2-methyl-propan-1-one 2-hydroxy-1-(4-{[4-(2-hydroxy-2-methyl-propionyl)-phenyl]-octadecylsulfanyl-methyl}-phenyl)-2-methyl-propan-1-one 2-hydroxy-1-(4-{(2-hydroxy-ethylsulfanyl)-[4-(2-hydroxy-2-methyl-propionyl)-phenyl]-methyl}-phenyl)-2-methyl-propan-1-one 2-hydroxy-1-{4-[[4-(1-hydroxy-cyclohexanecarbonyl)-phenyl]-(2-hydroxy-ethylsulfanyl)-methyl]-phenyl}-2-methyl-propan-1-one 1-(4-{(2,3-dihydroxy-propylsulfanyl)-[4-(2-hydroxy-2-methyl-propionyl)-phenyl]-methyl}-phenyl)-2-hydroxy-2-methyl-propan-1-one 1-(4-{(3-dodecyloxy-2-hydroxy-propylsulfanyl)-[4-(2-hydroxy-2-methyl-proponyl)-phenyl]-methyl}-phenyl)-2-hydroxy-2-methyl-propan-1-one 1-(4-{benzylsulfanyl-[4-(2-methyl-2-morpholin-4-yl-propionyl)-phenyl]-methyl}-phenyl)-2-hydroxy-2-methyl-propan-1-one 2-hydroxy-1-(4-{[4-(2-hydroxy-2-methyl-butyryl)-phenyl]-4-tolylsulfanyl-methyl}-phenyl)-2-methyl-butan-1-one {bis[4-(2-hydroxy-2-methyl-propionyl)-phenyl]-methylsulfanyl}acetic acid octadecyl ester 3-{[3-(2-hydroxy-2-methyl-propionyl)-phenyl]-[4-(2-hydroxy-2-methyl-propionyl)-phenyl]-methylsulfanyl}-propionic acid dodecyl ester 2-{bis[4-(2-ethyl-2-hydroxy-hexanoyl)-phenyl]-methylsulfanyl}-propionic acid hexyl ester 1-(4-{amino-[4-(2-hydroxy-2-methyl-propionyl)-phenyl]-methyl}-phenyl)-2-hydroxy-2-methyl-propan-1-one 2-Hydroxy-1-(4-{[4-(2-hydroxy-2-methyl-propionyl)-phenyl]-methylamino-methyl}-phenyl)-2-methyl-propan-1-one 1-{Dimethylamino-[4-(2-hydroxy-2-methyl-propionyl)-phenyl]-methyl}-phenyl)-2-hydroxy-2-methyl-propan-1-one 1-(4-{Ethylamino-[4-(2-hydroxy-2-methyl-propionyl)-phenyl]-methyl}-phenyl)-2-hydroxy-2-methyl-propan-1-one 1-(4-{Diethylamino-[4-(2-hydroxy-2-methyl-propionyl)-phenyl]-methyl}-phenyl)-2-hydroxy-2-methyl-propan-1-one 1-(4-{Butylamino-[4-(2-hydroxy-2-methyl-propionyl)-phenyl]-methyl}-phenyl)-2-hydroxy-2-methyl-propan-1-one 1-(4-{Dibutylamino-[4-(2-hydroxy-2-methyl-propionyl)-phenyl]-methyl}-phenyl)-2-hydroxy-2-methyl-propan-1-one 1-(4-{Hexylamino-[4-(2-hydroxy-2-methyl-propionyl)-phenyl]-methyl}-phenyl)-2-hydroxy-2-methyl-propan-1-one 1-(4-{Allylamino-[4-(2-hydroxy-2-methyl-propionyl)-phenyl]-methyl}-phenyl)-2-hydroxy-2-methyl-propan-1-one 1-{Diallylamino-[4-(2-hydroxy-2-methyl-propionyl)-phenyl]-methyl}-phenyl)-2-hydroxy-2-methyl-propan-1-one 1-(4-{Benzylamino-[4-(2-hydroxy-2-methyl-propionyl)-phenyl]-methyl}-phenyl)-2-hydroxy-2-methyl-propan-1-one 2-Hydroxy-1-(4-{[4-(2-hydroxy-2-methyl-propionyl)-phenyl]-phenethylamino-methyl}-phenyl)-2-methyl-propan-1-one 1-(4-{Cyclohexylamino-[4-(2-hydroxy-2-methyl-propionyl)-phenyl]-methyl}-phenyl)-2-hydroxy-2-methyl-propan-1-one 3-({Bis-[4-(2-hydroxy-2-methyl-propionyl)-phenyl]-methyl}-amino)-propionitrile 3-[{Bis-[4-(2-hydroxy-2-methyl-propionyl)-phenyl]-methyl}-(2-cyano-ethyl)-amino]-propionitrile 3-({Bis-[4-(2-hydroxy-2-methyl-propionyl)-phenyl]-methyl}-amino)-propionic acid methyl ester 3-[{Bis-[4-(2-hydroxy-2-methyl-propionyl)-phenyl]-methyl}-(2-ethoxycarbonyl-ethyl)-amino]-propionic acid ethyl ester 2-Hydroxy-1-(4{(2-hydroxy-ethylamino)-[4-(2-hydroxy-2-methyl-propionyl)-phenyl]-methyl}-phenyl)-2-methyl-propan-1-one 2-Hydroxy-1-(4-{[(2-hydroxy-ethyl)-methyl-amino]-[4-(2-hydroxy-2-methyl-propionyl)-phenyl]-methyl}-phenyl)-2-methyl-propan-1-one 1-(4-{[Ethyl-(2-hydroxy-ethyl)-amino]-[4-(2-hydroxy-2-methyl-propionyl)-phenyl]-methyl}-phenyl)-2-hydroxy-2-methyl-propan-1-one 1-(4-{[Butyl-(2-hydroxy-ethyl)-amino]-[4-(2-hydroxy-2-methyl-propionyl)-phenyl]-methyl}-phenyl)-2-hydroxy-2-methyl-propan-1-one 1-(4-{[Bis-(2-hydroxy-ethyl)-amino]-[4-(2-hydroxy-2-methyl-propionyl)-phenyl]-methyl}-phenyl)-2-hydroxy-2-methyl-propan-1-one 1-(4-{[Bis-(2-methoxy-ethyl)-amino]-[4-(2-hydroxy-2-methyl-propionyl)-phenyl]-methyl}-phenyl)-2-hydroxy-2-methyl-propan-1-one 2-Hydroxy-1-{4-[[4-(2-hydroxy-2-methyl-propionyl)-phenyl]-(2-methoxy-ethylamino)-methyl]-phenyl}-2-methyl-propan-1-one 2-Hydroxy-1-{4-[[4-(2-hydroxy-2-methyl-propionyl)-phenyl]-(3-hydroxy-propylamino)-methyl]-phenyl}-2-methyl-propan-1-one 2-Hydroxy-1-{4-[[4-(2-hydroxy-2-methyl-propionyl)-phenyl]-(2-hydroxy-propylamino)-methyl]-phenyl}-2-methyl-propan-1-one 2-Hydroxy-1-(4-{[4-(2-hydroxy-2-methyl-propionyl)-phenyl]-[2-hydroxy-propyl)-methyl-amino]-methyl}-phenyl)-2-methyl-propan-1-one 1-(4-{[Ethyl-(2-hydroxy-propyl)-amino]-[4-(2-hydroxy-2-methyl-propionyl)-phenyl]-methyl}-phenyl)-2-hydroxy-2-methyl-propan-1-one 1-(4-{[Bis-(2-hydroxy-propyl)-amino]-[4-(2-hydroxy-2-methyl-propionyl)-phenyl]-methyl}-phenyl)-2-hydroxy-2-methyl-propan-1-one 2-Hydroxy-1-(4-{(2-hydroxy-1-methyl-ethylamino)-[4-(2-hydroxy-2-methyl-propionyl)-phenyl]-methyl}-phenyl)-2-methyl-propan-1-one 2-Hydroxy-1-(4-{[(2-hydroxy-1-methyl-ethyl)-methyl-amino]-[4-(2-hydroxy-2-methyl-propionyl)-phenyl]-methyl}-phenyl)-2-methyl-propan-1-one 2-Hydroxy-1-(4-{(4-hydroxy-butylamino)-[4-(2-hydroxy-2-methyl-propionyl)-phenyl]-methyl}-phenyl)-2-methyl-propan-1-one (6-Isocyanato-hexyl)-carbamic acid 2-({bis-[4-(2-hydroxy-2-methyl-propionyl)-phenyl]-methyl}-methyl-amino)-ethyl ester 2-Hydroxy-1-(4-{{[2-(2-hydroxy-ethoxy)-ethyl]-methyl-amino}-[4-(2-hydroxy-2-methyl-propionyl)-phenyl]-methyl}-phenyl)-2-methyl-propan-1-one 2-Hydroxy-1-(4-{{2-[2-(2-hydroxy-ethoxy)-ethoxy]-ethylamino}-[4-(2-hydroxy-2-methyl-propionyl)-phenyl]-methyl}-phenyl)-2-methyl-propan-1-one 2-Hydroxy-1-(4-{[(2-{2-[2-(2-hydroxy-ethoxy)-ethoxy]-ethoxy}-ethyl)-methyl-amino]-[4-(2-hydroxy-2-methyl-propionyl)-phenyl]-methyl}-phenyl)-2-methyl-propan-1-one 2-Hydroxy-1-(4-{{[2-(6-hydroxy-hexyloxy)-ethyl]-methyl-amino}-[4-(2-hydroxy-2-methyl-propionyl)-phenyl]-methyl}-phenyl)-2-methyl-propan-1-one 1-(4-{(2-Amino-ethylamino)-[4-(2-hydroxy-2-methyl-propionyl)-phenyl]-methyl}-phenyl)-2-hydroxy-2-methyl-propan-1-one 1-(4-{(3-Amino-propylamino)-[4-(2-hydroxy-2-methyl-propionyl)-phenyl]-methyl}-phenyl)-2-hydroxy-2-methyl-propan-1-one 1-(4-{(6-Amino-hexylamino)-[4-(2-hydroxy-2-methyl-propionyl)-phenyl]-methyl}-phenyl)-2-hydroxy-2-methyl-propan-1-one 2-Hydroxy-1-(4-{[4-(2-hydroxy-2-methyl-propionyl)-phenyl]-piperidin-1-yl-methyl}-phenyl)-2-methyl-propan-1-one 2-Hydroxy-1-(4-{[4-(2-hydroxy-2-methyl-propionyl)-phenyl]-morpholin-4-yl-methyl}-phenyl)-2-methyl-propan-1-one 1-(4-{(2,6-Dimethyl-morpholin-4-yl)-[4-(2-hydroxy-2-methyl-propionyl)-phenyl]-methyl}-phenyl)-2-hydroxy-2-methyl-propan-1-one 2-Hydroxy-1-(4-{[4-(2-hydroxy-2-methyl-propionyl)-phenyl]-piperazin-1-yl-methyl}-phenyl)-2-methyl-propan-1-one 2-Hydroxy-1-{4-[[4-(2-hydroxy-2-methyl-propionyl)-phenyl]-(4-methyl-piperazin-1-yl)-methyl]-phenyl}-2-methyl-propan-1-one 2-Hydroxy-1-(4-{[4-(2-hydroxy-ethyl)-piperazin-1-yl]-[4-(2-hydroxy-2-methyl-propionyl)-phenyl]-methyl}-phenyl)-2-methyl-propan-1-one 2-Hydroxy-1-(4-{[4-(2-hydroxy-2-methyl-propionyl)-phenyl]-[4-(2-hydroxy-propyl)-piperazin-1-yl]-methyl}-phenyl)-2-methyl-propan-1-one 2-Hydroxy-1-(4-{[4-(2-hydroxy-2-methyl-propionyl)-phenyl]-pyrrolidin-1-yl-methyl}-phenyl)-2-methyl-propan-1-one 1-(4-{{2-[2-(2-Amino-ethoxy)-ethoxy]-ethylamino}-[4-(2-hydroxy-2-methyl-propionyl)-phenyl]-methyl}-phenyl)-2-hydroxy-2-methyl-propan-1-one 2-Hydroxy-1-{4-[[4-(2-hydroxy-2-methyl-propionyl)-phenyl]-(2-{2-[2-(2-methoxy-1-methyl-ethoxy)-1-methylethoxy]-1-methyl-ethoxy}-1-methyl-ethylamino)-methyl]-phenyl}-2-methyl-propan-1-one 2-Hydroxy-1-[4-([4-(2-hydroxy-2-methyl-propionyl)-phenyl]-{2-[2-(2-{2-[2-(2-methoxy-1-methyl-ethoxy)-1-methyl-ethoxy]-1-methyl-ethoxy}-1-methyl-ethoxy)-1-methyl-ethoxy]-1-methyl-ethylamino}-methyl)-phenyl]-2-methyl-propan-1-one 2-Hydroxy-1-{4-[[4-(2-hydroxy-2-methyl-propionyl)-phenyl]-(2-{2-[2-(2-{2-[2-(2-methoxy-1-methyl-ethoxy)-1-methyl-ethoxy]-1-methyl-ethoxy}-1-methyl-ethoxy)-1-methyl-ethoxy]-1-methyl-ethoxy}-1-methyl-ethylamino)-methyl]-phenyl}-2-methyl-propan-1-one 2-Hydroxy-1-(4-{[4-(2-hydroxy-2-methyl-propionyl)-phenyl]-[2-(2-{2-[2-(2-{2-[2-(2-methoxy-ethoxy)-ethoxy]-ethoxy}-ethoxy)-1-methyl-ethoxy]-1-methyl-ethoxy}-1-methyl-ethoxy)-1-methyl-ethylamino]-methyl}-phenyl)-2-methyl-propan-1-one 2-Hydroxy-1-(4-{[4-(2-hydroxy-2-methyl-propionyl)-phenyl]-[2-(2-{2-[2-(2-{2-[2-(2-methoxy-ethoxy)-ethoxy]-ethoxy}-1-methyl-ethoxy)-1-methyl-ethoxy]-1-methyl-ethoxy}-1-methyl-ethoxy)-1-methyl-ethylamino]-methyl}-phenyl)-2-methyl-propan-1-one 2-Hydroxy-1-(4-{[4-(2-hydroxy-2-methyl-propionyl)-phenyl]-[2-(2-{2-[2-(2-{2-[2-(2-methoxy-ethoxy)-ethoxy]-1-methyl-ethoxy}-1-methyl-ethoxy)-1-methyl-ethoxy]-1-methyl-ethoxy}-1-methyl-ethoxy)-1-methyl-ethylamino]-methyl}-phenyl)-2-methyl-propan-1-one 2-Hydroxy-1-[4-([4-(2-hydroxy-2-methyl-propionyl)phenyl]-{2-[2-(2-{2-[2-(2-methoxy-ethoxy)-ethoxy]-1-methyl-ethoxy}-1-methyl-ethoxy)-1-methyl-ethoxy]-1-methyl-ethylamino}-methyl)-phenyl]-2-methyl-propan-1-one 1-(4-{[2-(2-{2-[2-(2-Amino-propoxy)-propoxy]-propoxy}-propoxy)-1-methyl-ethylamino]-[4-(2-hydroxy-2-methyl-propionyl)-phenyl]-methyl}-phenyl)-2-hydroxy-2-methyl-propan-1-one 1-(4-{(2-{2-[2-(2-{2-[2-(2-Amino-propoxy)-propoxy]-propoxy}-propoxy)-propoxy]-propoxy}-1-methyl-ethylamino)-[4-(2-hydroxy-2-methyl-propionyl)-phenyl]-methyl}-phenyl)-2-hydroxy-2-methyl-propan-1-one 1-(4-{[2-(2-{2-[2-(2-{2-[2-(2-Amino-propoxy)-propoxy]-propoxy}-propoxy)-propoxy]-propoxy}-propoxy)-1-methyl-ethylamino]-[4-(2-hydroxy-2-methyl-propionyl)-phenyl]-methyl}-phenyl)-2-hydroxy-2-methyl-propan-1-one 1-(4-{{2-[2-(2-{2-[2-(2-{2-[2-(2-Amino-propoxy)-propoxy]-propoxy}-propoxy)-propoxy]-propoxy}-propoxy)-propoxy]-1-methyl-ethylamino}-[4-(2-hydroxy-2-methyl-propionyl)-phenyl]-methyl}-phenyl)-2-hydroxy-2-methyl-propan-1-one 1-(4-{(2-{2-[2-(2-{2-[2-(2-{2-[2-(2-Amino-propoxy)-propoxy]-propoxy}-propoxy)-propoxy]-propoxy}-propoxy)-propoxy]-propoxy}-1-methyl-ethylamino)-[4-(2-hydroxy-2-methyl-propionyl)-phenyl]-methyl}-phenyl)-2-hydroxy-2-methyl-propan-1-one 1-(4-{(2-{2-[2-(2-{2-[2-(2-Amino-propoxy)-1-methyl-ethoxy]-1-methyl-ethoxy}-1-methyl-ethoxy)-1-methyl-ethoxy]-1-methyl-ethoxy}-1-methyl-ethylamino)-[4-(2-hydroxy-2-methyl-propionyl)-phenyl]-methyl}-phenyl)-2-hydroxy-2-methyl-propan-1-one 1-(4-{{2-[2-(2-{2-[2-(2-Amino-propoxy)-1-methyl-ethoxy]-1-methyl-ethoxy}-1-methyl-ethoxy)-1-methyl-ethoxy]-1-methyl-ethoxy}-1-methyl-ethylamino}-[4-(2-hydroxy-2-methyl-propionyl)-phenyl]-methyl}-phenyl)-2-hydroxy-2-methyl-propan-1-one 1-(4-{{2-[2-(2-{2-[2-(2-Amino-propoxy)-propoxy]-propoxy}-propoxy)-propoxy]-propoxy}-1-methyl-ethylamino}-[4-(2-hydroxy-2-methyl-propionyl)-phenyl]-methyl}-phenyl)-2-hydroxy-2-methyl-propan-1-one 1-(4-{[2-(2-{2-(2-Amino-propoxy)-3-[2-(2-amino-propoxy)-propoxy]-propoxy}-1-methyl-ethoxy)-1-methyl-ethylamino]-[4-(2-hydroxy-2-methyl-propionyl)-phenyl]-methyl}-phenyl)-2-hydroxy-2-methyl-propan-1-one 1-(4-{[2-(2-{2,3-Bis-[2-(2-amino-propoxy)-propoxy]-propoxy}-1-methyl-ethoxy)-1-methyl-ethylamino]-[4-(2-hydroxy-2-methyl-propionyl)-phenyl]-methyl}-phenyl)-2-hydroxy-2-methyl-propan-1-one 1-(4-{{2-[2-(2-[2-(2-Amino-propoxy)-propoxy]-3-{2-[2-(2-amino-propoxy)-propoxy]-propoxy}-propoxy)-1-methyl-ethoxy]-1-methyl-ethylamino}-[4-(2-hydroxy-2-methyl-propionyl)-phenyl]-methyl}-phenyl)-2-hydroxy-2-methyl-propan-1-one 1-(4-{[2-{2-(2-{2,3-Bis-[2-(2-amino-propoxy)-propoxy]-propoxy}-1-methyl-ethoxy)-1-methyl-ethoxy]-1-methyl-ethylamino}-[4-(2-hydroxy-2-methyl-propionyl)-phenyl]-methyl}-phenyl)-2-hydroxy-2-methyl-propan-1-one 1-(4-{(2-{2-[2-(2-[2-(2-Amino-propoxy)-propoxy]-3-{2-[2-(2-amino-propoxy)-propoxy]-propoxy}-propoxy)-1-methyl-ethoxy)-1-methyl-ethoxy}-1-methyl-ethylamino)-[4-(2-hydroxy-2-methyl-propionyl)-phenyl]-methyl}-phenyl)-2-hydroxy-2-methyl-propan-1-one Examples of compounds of formula II are:

a) ether structures with di- and oligo-alcohols, from the list:

1-(4-{[2-(2-{bis[4-(2-hydroxy-2-methyl-propionyl)-phenyl]-methoxy}-ethoxy)-ethoxy]-[4-(2-hydroxy-2-methyl-propionyl)-phenyl]-methyl}-phenyl)-2-hydroxy-2-methyl-propan-1-one 1-(4-{(2-{bis[4-(2-hydroxy-2-methyl-propionyl)-phenyl]-methoxy}-ethoxy)-[4-(2-hydroxy-2-methyl-propionyl)-phenyl]-methyl}-phenyl)-2-hydroxy-2-methyl-propan-1-one 2-hydroxy-1-(4-{[4-(2-hydroxy-2-methyl-propionyl)-phenyl]-[2-(2-{[4-(2-hydroxy-2-methyl-propionyl)-phenyl]-[3-(2-hydroxy-2-methyl-propionyl)-phenyl]-methoxy}-ethoxy)-ethoxy]-methyl}-phenyl)-2-methyl-propan-1-one 2-hydroxy-1-(4-{[3-(2-hydroxy-2-methyl-propionyl)-phenyl]-[2-(2-{[4-(2-hydroxy-2-methyl-propionyl)-phenyl]-[3-(2-hydroxy-2-methyl-propionyl)-phenyl]-methoxy}-ethoxy)-ethoxy]-methyl}-phenyl)-2-methyl-propan-1-one 1-(4-{{2-[2-(2-{bis[4-(2-hydroxy-2-methyl-propionyl)-phenyl]-methoxy}-ethoxy)-ethoxy]-ethoxy}-[4-(2-hydroxy-2-methyl-propionyl)-phenyl]-methyl}-phenyl)-2-hydroxy-2-methyl-propan-1-one 1-(4-{(2-{2-[2-(2-{bis[4-(2-hydroxy-2-methyl-propionyl)-phenyl]-methoxy}-ethoxy)-ethoxy]-ethoxy}-ethoxy)-[4-(2-hydroxy-2-methyl-propionyl)-phenyl]-methyl}-phenyl)-2-hydroxy-2-methyl-propan-1-one 1-(4-{[2-(2-{2-[2-(2-{bis[4-(2-hydroxy-2-methyl-propionyl)-phenyl]-methoxy}-ethoxy)-ethoxy]-ethoxy}-ethoxy)-ethoxy]-[4-(2-hydroxy-2-methyl-propionyl)-phenyl]-methyl}-phenyl)-2-hydroxy-2-methyl-propan-1-one 1-(4-{{2-[2-(2-{2-[2-(2-{bis[4-(2-hydroxy-2-methyl-propionyl)-phenyl]-methoxy}-ethoxy)-ethoxy]-ethoxy}-ethoxy)-ethoxy]-ethoxy}-[4-(2-hydroxy-2-methyl-propionyl)-phenyl]-methyl}-phenyl)-2-hydroxy-2-methyl-propan-1-one 1-(4-{(2-{2-[2-(2-{2-[2-(2-{bis[4-(2-hydroxy-2-methyl-propionyl)-phenyl]-methoxy}-ethoxy)-ethoxy]-ethoxy}-ethoxy)-ethoxy]-ethoxy}-ethoxy)-[4-(2-hydroxy-2-methyl-propionyl)-phenyl]-methyl}-phenyl)-2-hydroxy-2-methyl-propan-1-one 1-(4-{[2-(2-{2-[2-(2-{2-[2-(2-{bis[4-(2-hydroxy-2-methyl-propionyl)-phenyl]-methoxy}-ethoxy)-ethoxy]-ethoxy}-ethoxy)-ethoxy]-ethoxy}-ethoxy)-ethoxy]-[4-(2-hydroxy-2-methyl-propionyl)-phenyl]-methyl}-phenyl)-2-hydroxy-2-methyl-propan-1-one 1-(4-{(2-[2-(2-{2-[2-(2-{2-[2-(2-{bis[4-(2-hydroxy-2-methyl-propionyl)-phenyl]-methoxy}-ethoxy)-ethoxy]-ethoxy}-ethoxy)-ethoxy]-ethoxy}-ethoxy)-ethoxy]-[4-(2-hydroxy-2-methyl-propionyl)-phenyl]-methyl}-phenyl)-2-hydroxy-2-methyl-propan-1-one 1-(4-{(2-{bis[4-(2-hydroxy-2-methyl-propionyl)-phenyl]-methoxy}-propoxy)-[4-(2-hydroxy-2-methyl-propionyl)-phenyl]-methyl}-phenyl)-2-hydroxy-2-methyl-propan-1-one 1-(4-{[2-(2-{bis[4-(2-hydroxy-2-methyl-propiony)-phenyl]-methoxy}-1-methyl-ethoxy)-1-methyl-ethoxy]-[4-(2-hydroxy-2-methyl-propionyl)-phenyl]-methyl}-phenyl)-2-hydroxy-2-methyl-propan-1-one 1-(4-{{2-[2-(2-{bis[4-(2-hydroxy-2-methyl-propionyl)-phenyl]-methoxy}-1-methyl-ethoxy)-1-methyl-ethoxy]-1-methyl-ethoxy}-[4-(2-hydroxy-2-methyl-propionyl)-phenyl]-methyl}-phenyl)-2-hydroxy-2-methyl-propan-1-one 1-(4-{(3-{bis[4-(2-hydroxy-2-methyl-propionyl)-phenyl]-methoxy}-2-hydroxy-propoxy)-[4-(2-hydroxy-2-methyl-propionyl)-phenyl]-methyl}-phenyl)-2-hydroxy-2-methyl-propan-1-one 1-(4-{(2,3-bis{bis[4-(2-hydroxy-2-methyl-propionyl)-phenyl]-methoxy}-propoxy)-[4-(2-hydroxy-2-methyl-propionyl)-phenyl]-methyl}-phenyl)-2-hydroxy-2-methyl-propan-1-one 1-(4-{(4-{bis[4-(2-hydroxy-2-methyl-propionyl)-phenyl]-methoxymethyl}-cyclohexylmethoxy)-[4-(2-hydroxy-2-methyl-propionyl)-phenyl]-methyl}-phenyl)-2-hydroxy-2-methyl-propan-1-one 2-hydroxy-1-(4-{(4-hydroxymethyl-cyclohexylmethoxy)-[4-(2-hydroxy-2-methyl-propionyl)-phenyl]-methyl}-phenyl)-2-methyl-propan-1-one 1-(4-{(4-{bis[4-(2-hydroxy-2-methyl-propionyl)-phenyl]-methoxymethyl}-benzyloxy)-[4-(2-hydroxy-2-methyl-propionyl)-phenyl]-methyl}-phenyl)-2-hydroxy-2-methyl-propan-1-one 2-hydroxy-1-(4-{(4-hydroxymethyl-benzyloxy)-[4-(2-hydroxy-2-methyl-propionyl)-phenyl]-methyl}-phenyl)-2-methyl-propan-1-one 1-(4-{(4-{bis[4-(2-hydroxy-2-methyl-propionyl)-phenyl]-methoxy}-cyclohexyloxy)-[4-(2-hydroxy-2-methyl-propionyl)-phenyl]-methyl}phenyl)-2-hydroxy-2-methyl-propan-1-one 2-hydroxy-1-(4-{(4-hydroxy-cyclohexyloxy)-[3-(2-hydroxy-2-methyl-propionyl)-phenyl]-methyl}-phenyl)-2-methyl-propan-1-one 1-(4-{(4-{bis[4-(2-hydroxy-2-methyl-propionyl)-phenyl]-methoxy}-butoxy)-[4-(2-hydroxy-2-methyl-propionyl)-phenyl]-methyl}-phenyl)-2-hydroxy-2-methyl-propan-1-one 1-(4-{(5-{bis[4-(2-hydroxy-2-methyl-propionyl)-phenyl]-methoxy}-pentyloxy)-[4-(2-hydroxy-2-methyl-propionyl)-phenyl]-methyl}-phenyl)-2-hydroxy-2-methyl-propan-1-one 1-(4-{(6-{bis[4-(2-hydroxy-2-methyl-propionyl)-phenyl]-methoxy}-hexyloxy)-[4-(2-hydroxy-2-methyl-propionyl)-phenyl]-methyl}-phenyl)-2-hydroxy-2-methyl-propan-1-one 1-(4-{(10-{bis[4-(2-hydroxy-2-methyl-propionyl)-phenyl]-methoxy})-decyloxy)-[4-(2-hydroxy-2-methyl-propionyl)-phenyl]-methyl}phenyl)-2-hydroxy-2-methyl-propan-1-one 1-(4-{(12-{bis[4-(2-hydroxy-2-methyl-propionyl)-phenyl]-methoxy}-dodecyloxy)-[4-(2-hydroxy-2-methyl-propionyl)-phenyl]-methyl}-phenyl)-2-hydroxy-2-methyl-propan-1-one 1-(4-{(18-{bis[4-(2-hydroxy-2-methyl-propionyl)-phenyl]-methoxy}-octadecyloxy)-[4-(2-hydroxy-2-methyl-propionyl)-phenyl]-methyl}-phenyl)-2-hydroxy-2-methyl-propan-1-one 1-(4-{[3-(3-{bis[4-(2-hydroxy-2-methyl-propionyl)-phenyl]-methoxy}-2-hydroxy-propoxy)-2-hydroxy-propoxy]-[4-(2-hydroxy-2-methyl-propionyl)-phenyl]-methyl}-phenyl)-2-hydroxy-2-methyl-propan-1-one 1-(4-{[2-{bis[4-(2-hydroxy-2-methyl-propionyl)-phenyl]-methoxy}-3-(3-{bis[4-(2-hydroxy-2-methyl-propionyl)-phenyl]-methoxy}-2-hydroxy-propoxy)propoxy]-[4-(2-hydroxy-2-methyl-propionyl)-phenyl]-methyl}-phenyl)-2-hydroxy-2-methyl-propan-1-one 1-(4-{(1-(2,3-bis{bis[4-(2-hydroxy-2-methyl-propionyl)-phenyl]-methoxy}-propoxymethyl)-2-{bis[4-(2-hydroxy-2-methyl-propionyl)-phenyl]-methoxy}-ethoxy)-[4-(2-hydroxy-2-methyl-propionyl)-phenyl]-methyl}phenyl)-2-hydroxy-2-methyl-propan-1-one 2-hydroxy-1-(4-{(3-hydroxy-2,2-bis-hydroxymethyl-propoxy)-[4-(2-hydroxy-2-methyl-propionyl)-phenyl]-methyl}-phenyl)-2-methyl-propan-1-one 1-(4-{(3-{bis[4-(2-hydroxy-2-methyl-propionyl)-phenyl]-methoxy}-2,2-bis-hydroxymethyl-propoxy)-[4-(2-hydroxy-2-methyl-propionyl)-phenyl]-methyl}-phenyl)-2-hydroxy-2-methyl-propan-1-one 1-(4-{(3-{bis[4-(2-hydroxy-2-methyl-propionyl)-phenyl]-methoxy}-2-{bis[4-(2-hydroxy-2-methyl-propionyl)-phenyl]-methoxymethyl}-2-hydroxymethyl-propoxy)-[4-(2-hydroxy-2-methyl-propionyl)-phenyl]-methyl}-phenyl)-2-hydroxy-2-methyl-propan-1-one 1-(4-{(3-{bis[4-(2-hydroxy-2-methyl-propionyl)-phenyl]-methoxy}-2,2-bis{bis[4-(2-hydroxy-2-methyl-propionyl)-phenyl]-methoxymethyl}-propoxy)-[4-(2-hydroxy-2-methyl-propionyl)-phenyl]-methyl}-phenyl)-2-hydroxy-2-methyl-propan-1-one 2-hydroxy-1-(4-{(3-hydroxy-2-hydroxymethyl-2-methyl-propoxy)-[4-(2-hydroxy-2-methyl-propionyl)-phenyl]-methyl}-phenyl)-2-methyl-propan-1-one 1-(4-{(2-{bis[4-(2-hydroxy-2-methyl-propionyl)-phenyl]-methoxymethyl}-3-hydroxy-2-methyl-propoxy)-[4-(2-hydroxy-2-methyl-propionyl)-phenyl]-methyl}-phenyl)-2-hydroxy-2-methyl-propan-1-one 1-(4-{(3-{bis[4-(2-hydroxy-2-methyl-propionyl)-phenyl]-methoxy}-2-{bis[4-(2-hydroxy-2-methyl-propionyl)-phenyl]-methoxymethyl}-2-methyl-propoxy)-[4-(2-hydroxy-2-methyl-propionyl)-phenyl]-methyl}-phenyl)-2-hydroxy-2-methyl-propan-1-one 1-(4-{(2,2-bis-hydroxymethyl-butoxy)-[4-(2-hydroxy-2-methyl-propionyl)-phenyl]-methyl}-phenyl)-2-hydroxy-2-methyl-propan-1-one 1-(4-{(2-{bis[4-(2-hydroxy-2-methyl-propionyl)-phenyl]-methoxymethyl}-2-hydroxymethyl-butoxy)-[4-(2-hydroxy-2-methyl-propionyl)-phenyl]-methyl}-phenyl)-2-hydroxy-2-methyl-propan-1-one 1-(4-{(2,2-bis{bis[4-(2-hydroxy-2-methyl-propionyl)-phenyl]-methoxymethyl}-butoxy)-[4-(2-hydroxy-2-methyl-propionyl)-phenyl]-methyl}-phenyl)-2-hydroxy-2-methyl-propan-1-one 2-hydroxy-1-(4-{{2-[(2-hydroxy-ethyl)-methyl-amino]-ethoxy}-[4-(2-hydroxy-2-methyl-propionyl)-phenyl]-methyl}-phenyl)-2-methyl-propan-1-one 1-(4-{{2-[2-{bis[4-(2-hydroxy-2-methyl-propionyl)-phenyl]-methoxy}-ethyl)-methyl-amino]-ethoxy}-[4-(2-hydroxy-2-methyl-propionyl)-phenyl]-methyl}-phenyl)-2-hydroxy-2-methyl-propan-1-one 1-(4-{{2-[bis(2-hydroxy-ethyl)-amino]-ethoxy}-[4-(2-hydroxy-2-methyl-propionyl)-phenyl]-methyl}-phenyl)-2-hydroxy-2-methyl-propan-1-one 1-(4-{{2-[(2-{bis[4-(2-hydroxy-2-methyl-propionyl)-phenyl]-methoxy}-ethyl)-(2-hydroxy-ethyl)-amino]-ethoxy}-[4-(2-hydroxy-2-methyl-propionyl)-phenyl]-methyl}-phenyl)-2-hydroxy-2-methyl-propan-1-one 1-(4-{{2-[bis(2-{bis[4-(2-hydroxy-2-methyl-propionyl)-phenyl]-methoxy}-ethyl)-amino]-ethoxy}-[4-(2-hydroxy-2-methyl-propionyl)-phenyl]-methyl}-phenyl)-2-hydroxy-2-methyl-propan-1-one 1-(2-{bis[4-(2-hydroxy-2-methyl-propionyl)-phenyl]-methoxy}-ethyl)-3,5-bis(2-hydroxy-ethyl)-[1,3,5]triazinane-2,4,6-trione 1,3-bis(2-{bis[4-(2-hydroxy-2-methyl-propionyl)-phenyl]-methoxy}-ethyl)-5-(2-hydroxy-ethyl)-[1,3,5]triazinane-2,4,6-trione 1,3,5-tris(2-{bis[4-(2-hydroxy-2-methyl-propionyl)-phenyl]-methoxy}-ethyl)-[1,3,5]triazinane-2,4,6-trione 1-(4-{[3-(4-{1-[4-(3-{bis[4-(2-hydroxy-2-methyl-propionyl)-phenyl]-methoxy}-2-hydroxy-propoxy)-phenyl]-1-methyl-ethyl}-phenoxy)-2-hydroxy-propoxy]-[4-(2-hydroxy-2-methyl-propionyl)-phenyl]-methyl}-phenyl)-2-hydroxy-2-methyl-propan-1-one 1-(4-{[3-(4-{1-[4-(2,3-dihydroxy-propoxy)-phenyl]-1-methyl-ethyl}-phenoxy)-2-hydroxy-propoxy]-[3-(2-hydroxy-2-methyl-propionyl)-phenyl]-methyl}-phenyl)-2-hydroxy-2-methyl-propan-1-one 1-(4-{(3-{4-[4-(3-{bis[4-(2-hydroxy-2-methyl-propionyl)-phenyl]-methoxy}-2-hydroxy-propoxy)-cyclohexylmethyl]-cyclohexyloxy}-2-hydroxy-propoxy)-[4-(2-hydroxy-2-methyl-propionyl)-phenyl]-methyl}-phenyl)-2-hydroxy-2-methyl-propan-1-one 1-(4-{(3-{4-[4-(2,3-dihydroxy-propoxy)-cyclohexylmethyl]-cyclohexyloxy}-2-hydroxy-propoxy)-[4-(2-hydroxy-2-methyl-propionyl)-phenyl]-methyl}-phenyl)-2-hydroxy-2-methyl-propan-1-one 1-(4-{(3-{4-[4-(3-{bis[4-(2-hydroxy-2-methyl-propionyl)-phenyl]-methoxy}-2-hydroxy-propoxy)-benzyl]-phenoxy}-2-hydroxy-propoxy)-[4-(2-hydroxy-2-methyl-propionyl)-phenyl]-methyl}-phenyl)-2-hydroxy-2-methyl-propan-1-one 1-(4-{(3-{4-[4-(2,3-dihydroxy-propoxy)-benzyl]-phenoxy}-2-hydroxy-propoxy)-[4-(2-hydroxy-2-methyl-propionyl)-phenyl]-methyl}-phenyl)-2-hydroxy-2-methyl-propan-1-one 1-(4-{{3-[4-(3-{bis[4-(2-hydroxy-2-methyl-propionyl)-phenyl]-methoxy}-2-hydroxy-propoxy)-butoxy]-2-hydroxy-propoxy}-[4-(2-hydroxy-2-methyl-propionyl)-phenyl]-methyl}-phenyl)-2-hydroxy-2-methyl-propan-1-one 1-(4-{{3-[4-(2,3-dihydroxy-propoxy)-butoxy]-2-hydroxy-propoxy}-[4-(2-hydroxy-2-methyl-propionyl)-phenyl]-methyl}-phenyl)-2-hydroxy-2-methyl-propan-1-one 1-(4-{{3-[5-(3-{bis[4-(2-hydroxy-2-methyl-propionyl)-phenyl]-methoxy}-2-hydroxy-propoxy)-pentyloxy]-2-hydroxy-propoxy}-[4-(2-hydroxy-2-methyl-propionyl)-phenyl]-methyl}-phenyl)-2-hydroxy-2-methyl-propan-1-one 1-(4-{{3-[6-(3-{bis[4-(2-hydroxy-2-methyl-propionyl)-phenyl]-methoxy}-2-hydroxy-propoxy)-hexyloxy]-2-hydroxy-propoxy}-[4-(2-hydroxy-2-methyl-propionyl)-phenyl]-methyl}-phenyl)-2-hydroxy-2-methyl-propan-1-one 1-(4-{{3-[6-(2,3-dihydroxy-propoxy)-hexyloxy]-2-hydroxy-propoxy}-[4-(2-hydroxy-2-methyl-propionyl)-phenyl]-methyl}-phenyl)-2-hydroxy-2-methyl-propan-1-one 1-(4-{[2-(2-{bis[2-(2-{bis[4-(2-hydroxy-2-methyl-propionyl)-phenyl]-methoxy}-ethoxy)-ethoxy]-methylsilyloxy}-ethoxy)-ethoxy]-[4-(2-hydroxy-2-methyl-propionyl)-phenyl]-methyl}-phenyl)-2-hydroxy-2-methyl-propan-1-one 1-(4-{(2-{2-[2-(bis{2-[2-(2-{bis[4-(2-hydroxy-2-methyl-propionyl)-phenyl]-methoxy}-ethoxy)-ethoxy]-ethoxy}-methylsilyloxy)-ethoxy]-ethoxy}-ethoxy)-[4-(2-hydroxy-2-methyl-propionyl)-phenyl]-methyl}-phenyl)-2-hydroxy-2-methyl-propan-1-one b) urethane structures with di- and oligo-isocyanates, from the list:

(6-{bis[4-(2-hydroxy-2-methyl-propionyl)-phenyl]-methoxycarbonylamino}hexyl)-carbamic acid bis[4-(2-hydroxy-2-methyl-propionyl)-phenyl]-methyl ester (6-{bis[4-(2-hydroxy-2-methyl-propionyl)-phenyl]-methoxycarbonylamino}-3,5,5-trimethyl-hexyl)-carbamic acid bis[4-(2-hydroxy-2-methyl-propionyl)-phenyl]-methyl ester (3-{bis[4-(2-hydroxy-2-methyl-propionyl)-phenyl]-methoxycarbonylamino}-4-methyl-phenyl)-carbamic acid bis[4-(2-hydroxy-2-methyl-propionyl)-phenyl]-methyl ester (3-{bis[4-(2-hydroxy-2-methyl-propionyl)-phenyl]-methoxycarbonylamino}-4-methyl-cyclohexyl)-carbamic acid bis[4-(2-hydroxy-2-methyl-propionyl)-phenyl]-methyl ester (3-{bis[4-(2-hydroxy-2-methyl-propionyl)-phenyl]-methoxycarbonylamino}-phenyl)-carbamic acid bis[4-(2-hydroxy-2-methyl-propionyl)-phenyl]-methyl ester (3-{bis[4-(2-hydroxy-2-methyl-propionyl)-phenyl]-methoxycarbonylamino}-cyclohexyl)-carbamic acid bis[4-(2-hydroxy-2-methyl-propionyl)-phenyl]-methyl ester

[3-({bis[4-(2-hydroxy-2-methyl-propionyl)-phenyl]-methoxycarbonylamino}-methyl)-3,5,5-trimethyl-cyclohexyl]-carbamic acid bis[4-(2-hydroxy-2-methyl-propionyl)-phenyl]-methyl ester (5-isocyanato-1,3,3-trimethyl-cyclohexylmethyl)-carbamic acid bis[4-(2-hydroxy-2-methyl-propionyl)-phenyl]-methyl ester {6-[3,5-bis(6-{bis[4-(2-hydroxy-2-methyl-propionyl)-phenyl]-methoxycarbonylamino}-hexyl)-2,4,6-trioxo-[1,3,5]triazinan-1-yl]-hexyl}-carbamic acid bis[4-(2-hydroxy-2-methyl-propionyl)-phenyl]-methyl ester {6-[3-(6-{bis[4-(2-hydroxy-2-methyl-propionyl)-phenyl]-methoxycarbonylamino}-hexyl)-2,4-dioxo-[1,3]diazetidin-1-yl]-hexyl}-carbamic acid bis[4-(2-hydroxy-2-methyl-propionyl)-phenyl]-methyl ester {6-[1-Butoxycarbonyl-3-(6-{bis-[4-(2-hydroxy-2-methyl-propionyl)-phenyl]-methoxycarbonyl-amino}-hexyl)-ureido]-hexyl}-carbamic acid bis-[4-(2-hydroxy-2-methyl-propionyl)-phenyl]-methyl ester c) derivatives of di- and polyamines, from the list:

1-(4-{(2-{2-[2-({Bis-[4-(2-hydroxy-2-methyl-propionyl)-phenyl]-methyl}-amino)ethoxy]-ethoxy}-ethylamino)-[4-(2-hydroxy-2-methyl-propionyl)-phenyl]-methyl}-phenyl)-2-hydroxy-2-methyl-propan-1-one 1-(4-{[2-(2-{2-[2-({Bis-[4-(2-hydroxy-2-methyl-propionyl)-phenyl]-methyl}-amino)-propoxy]-propoxy}-propoxy)-1-methyl-ethylamino]-[4-(2-hydroxy-2-methyl-propionyl)-phenyl]-methyl}-phenyl)-2-hydroxy-2-methyl-propan-1-one 1-(4-{{(2-[2-(2-{2-[2-({Bis-[4-(2-hydroxy-2-methyl-propionyl)-phenyl]-methyl}-amino)-propoxy]-1-methyl-ethoxy)-1-methyl-ethoxy)-1-methyl-ethoxy]-1-methyl-ethylamino}-[4-(2-hydroxy-2-methyl-propionyl)-phenyl]-methyl}-phenyl)-2-hydroxy-2-methyl-propan-1-one 1-(4-{[2-(2-{2-[2-({Bis-[4-(2-hydroxy-2-methyl-propionyl)-phenyl]-methyl}-amino)-propoxy]-propoxy}-ethoxy)-1-methyl-ethylamino]-[4-(2-hydroxy-2-methyl-propionyl)-phenyl]-methyl}-phenyl)-2-hydroxy-2-methyl-propan-1-one 1-(4-{[2-(2-{2-[2-({Bis-[4-(2-hydroxy-2-methyl-propionyl)-phenyl]-methyl}-amino)-propoxy]-ethoxy}-propoxy)-1-methyl-ethylamino]-[4-(2-hydroxy-2-methyl-propionyl)-phenyl]-methyl}-phenyl)-2-hydroxy-2-methyl-propan-1-one 1-(4-{{2-[2-(2-{2-[2-({Bis-[4-(2-hydroxy-2-methyl-propionyl)-phenyl]-methyl}-amino)-propoxy]-propoxy}-propoxy)-propoxy]-1-methyl-ethylamino]-[4-(2-hydroxy-2-methyl-propionyl)-phenyl]-methyl}-phenyl)-2-hydroxy-2-methyl-propan-1-one 1-(4-{(2-{2-[2-(2-{2-[2-({Bis-[4-(2-hydroxy-2-methyl-propionyl)-phenyl]-methyl}-amino)-propoxy]-propoxy}-propoxy)-propoxy]-propoxy}-1-methyl-ethylamino)-[4-(2-hydroxy-2-methyl-propionyl)-phenyl]-methyl}-phenyl)-2-hydroxy-2-methyl-propan-1-one 1-(4-{{2-[2-(2-{2-[2-({Bis-[4-(2-hydroxy-2-methyl-propionyl)-phenyl]-methyl}-amino)-propoxy]-propoxy}-ethoxy)-1-methyl-ethoxy]-1-methyl-ethylamino}-[4-(2-hydroxy-2-methyl-propionyl)-phenyl]-methyl}-phenyl)-2-hydroxy-2-methyl-propan-1-one 1-(4-{(2-{2-[2-(2-{2-[2-({Bis-[4-(2-hydroxy-2-methyl-propionyl)-phenyl]-methyl}-amino)-propoxy]-propoxy}-ethoxy)-ethoxy]-1-methyl-ethoxy}-1-methyl-ethylamino)-[4-(2-hydroxy-2-methyl-propiony)-phenyl]-methyl}-phenyl)-2-hydroxy-2-methyl-propan-1-one 1-(4-{[2-(2-(2-Amino-propoxymethyl)-2-{2-[2-({bis-[4-(2-hydroxy-2-methyl-propionyl)-phenyl]-methyl}-amino)-propoxy]-propoxymethyl}-butoxy)-1-methyl-ethylamino]-[4-(2-hydroxy-2-methyl-propionyl)-phenyl]-methyl}-phenyl)-2-hydroxy-2-methyl-propan-1-one 1-(4-{{2-[2-(2-{2-[2-({Bis-[4-(2-hydroxy-2-methyl-propionyl)-phenyl]-methyl}-amino)-propoxy]-propoxymethyl}-butoxy)-2-[2-(2-(2-amino-propoxymethyl)-1-methyl-ethoxy]-1-methyl-ethylamino}-[4-(2-hydroxy-2-methyl-propionyl)-phenyl]-methyl}-phenyl)-2-hydroxy-2-methyl-propan-1-one 1-(4-{{2-[2-[2-(3-{2-[2-({Bis-[4-(2-hydroxy-2-methyl-propionyl)-phenyl]-methyl}-amino)-propoxy]-propoxy}-2-[2-amino-propoxy]-propoxy)-1-methyl-ethoxy]-1-methyl-ethylamino}-[4-(2-hydroxy-2-methyl-propionyl)-phenyl]-methyl}-phenyl)-2-hydroxy-2-methyl-propan-1-one d) derivatives in which R$_6$ is prepared from two types of divalent precursors, for example, from a diisocyanate and a diol from the lists:

(6-{Bis-[4-(2-hydroxy-2-methyl-propionyl)-phenyl]-methoxycarbonylamino}-hexyl)-carbamic acid bis-[4-(2-hydroxy-2-methyl-propionyl)-phenyl]-methyl ester (6-{Bis-[4-(2-hydroxy-2-methyl-propionyl)-phenyl]-methoxycarbonylamino}-hexyl)-carbamic acid 2-{2-[2-(6-{bis-[4-(2-hydroxy-2-methyl-propionyl)-phenyl]-methoxycarbonylamino}-hexylcarbamoyloxy)-ethoxy]-ethoxy}-ethyl ester

[6-(3-{2-[2-(2-Amino-ethoxy)-ethoxy]-ethyl}-ureido)-hexyl]-carbamic acid bis-[4-(2-hydroxy-2-methyl-propionyl)-phenyl]-methyl ester (6-{Bis-[4-(2-hydroxy-2-methyl-propionyl)-phenyl]-methoxycarbonylamino}-hexyl)-carbamic acid 2-[2-(2-hydroxy-ethoxy)-ethoxy]-ethyl ester (6-isocyanato-hexyl)-carbamic acid bis-[4-(2-hydroxy-2-methyl-propionyl)-phenyl]-methyl ester 6-{3-[2-(2-{2-[3-(6-{Bis-[4-(2-hydroxy-2-methyl-propionyl)-phenyl]-methoxycarbonylamino}-hexyl)-ureido]-ethoxy}-ethoxy)-ethyl]-ureido}-hexyl)-carbamic acid bis-[4-(2-hydroxy-2-methyl-propionyl)-phenyl]-methyl ester (6-{3-[2-(2-{2-[3-(6-{Bis-[4-(2-hydroxy-2-methyl-propionyl)-phenyl]-methoxycarbonylamino}-hexyl)-ureido]-propoxy}-propoxy)-1-methyl-ethyl]-ureido}-hexyl)-carbamic acid bis-[4-(2-hydroxy-2-methyl-propionyl)-phenyl]-methyl ester {6-[3-(2-{2-[2-(2-{2-[3-(6-{Bis-[4-(2-hydroxy-2-methyl-propionyl)-phenyl]-methoxycarbonylamino}hexyl)-ureido]-propoxy}-propoxy)-propoxy]-propoxy}-1-methyl-ethyl)-ureido]-hexyl}-carbamic acid bis-[4-(2-hydroxy-2-methyl-propionyl)-phenyl]-methyl ester (6-{Bis-[4-(2-hydroxy-2-methyl-propionyl)-phenyl]-methoxycarbonylamino}-hexyl)-carbamic acid 2-[2-(2-{2-[2-(6-{bis-[4-(2-hydroxy-2-methyl-propionyl)-phenyl]-methoxycarbonylamino}-hexylcarbamoyloxy)-ethoxy]-ethoxy}-ethoxy]-ethyl ester

[6-(3-{2-[2-(2-Amino-ethoxy)-ethoxy]-ethyl}-ureido)-hexyl]-carbamic acid bis-[4-(2-hydroxy-2-methyl-propionyl)-phenyl]-methyl ester (6-{3-[2-(2-{2-[3-(6-{Bis-[4-(2-hydroxy-2-methyl-propionyl)-phenyl]-methoxycarbonylamino}-hexyl)-ureido]-propoxy}-1-methyl-ethoxy)-1-methyl-ethyl]-ureido}-hexyl)-carbamic acid bis-[4-(2-hydroxy-2-methyl-propionyl)-phenyl]-methyl ester {6-[3-(2-{2-[2-(2-{2-[3-(6-{Bis-[4-(2-hydroxy-2-methyl-propionyl)-phenyl]-methoxycarbonylamino}-hexyl)-ureido]-propoxy}-propoxy)-propoxy]-propoxy}-1-methyl-ethyl)-ureido]-hexyl}-carbamic acid bis-[4-(2-hydroxy-2-methyl-propionyl)-phenyl]-methyl ester {6-[3-(2-{2-[2-(2-{2-[3-(6-{Bis-[4-(2-hydroxy-2-methyl-propionyl)-phenyl]-methoxycarbonylamino}-hexyl)-ureido]-propoxy}-propoxy)-propoxy]-ethoxy}-1-methyl-ethyl)-ureido]-hexyl}-carbamic acid bis-[4-(2-hydroxy-2-methyl-propionyl)-phenyl]-methyl ester {6-[2-({Bis-[4-(2-hydroxy-2-methyl-propionyl)-phenyl]-methyl}-methyl-amino)-ethoxycarbonylamino]-hexyl}-carbamic acid 2-({bis-[4-(2-hydroxy-2-methyl-propionyl)-phenyl]-methyl}-methyl-amino)-ethyl ester {6-[2-({Bis-[4-(2-hydroxy-2-methyl-propionyl)-phenyl]-methyl}-amino)-ethoxycarbonylamino]-hexyl}-carbamic acid 2-({bis-[4-(2-hydroxy-2-methyl-propionyl)-phenyl]-methyl}-amino)-ethyl ester {6-[2-({Bis-[4-(2-hydroxy-2-methyl-propionyl)-phenyl]-methyl}-amino)-ethoxycarbonylamino]-hexyl}-carbamic acid 2-({bis-[4-(2-hydroxy-2-methyl-propionyl)-phenyl]-methyl}-methyl-amino)-ethyl ester (6-isocyanato-hexyl)-carbamic acid 2-({bis-[4-(2-hydroxy-2-methyl-propionyl)-phenyl]-methyl}-methyl-amino)-ethyl ester Oxalic acid bis-[2-({bis-[4-(2-hydroxy-2-methyl-propionyl)-phenyl]-methyl}-methyl-amino)-ethyl]ester Malonic acid bis-[2-({bis-[4-(2-hydroxy-2-methyl-propionyl)-phenyl]-methyl}-methyl-amino)-ethyl]ester Succinic acid bis-[2-({bis-[4-(2-hydroxy-2-methyl-propionyl)phenyl]-methyl}-methyl-amino)-ethyl]ester Hexanedioic acid bis-[2-({bis-[4-(2-hydroxy-2-methyl-propionyl)-phenyl]-methyl}-methyl-amino)-ethyl]ester
Hexanedioic acid mono-[2-({bis-[4-(2-hydroxy-2-methyl-propionyl)-phenyl]-methyl}-methyl-amino)-ethyl]ester
Octanedioic acid bis-[2-({bis-[4-(2-hydroxy-2-methyl-propionyl)-phenyl]-methyl}-methyl-amino)-ethyl]ester
Decanedioic acid bis-[2-({bis-[4-(2-hydroxy-2-methyl-propionyl)-phenyl]-methyl}-methyl-amino)-ethyl]ester
Dodecanedioic acid bis-[2-({bis-[4-(2-hydroxy-2-methyl-propionyl)-phenyl]-methyl}-methyl-amino)-ethyl]ester
Octadecanedioic acid bis-[2-({bis-[4-(2-hydroxy-2-methyl-propionyl)-phenyl]-methyl}-methyl-amino)-ethyl]ester
[2-({Bis-[4-(2-hydroxy-2-methyl-propionyl)-phenyl]-methyl}-methyl-amino)-ethoxycarbonylmethoxy]-acetic acid 2-({bis-[4-(2-hydroxy-2-methyl-propionyl)-phenyl]-methyl}-methyl-amino)-ethyl ester
Terephthalic acid bis-[2-({bis-[4-(2-hydroxy-2-methyl-propionyl)-phenyl]-methyl}-methyl-amino)-ethyl]ester
Especially preferred are:

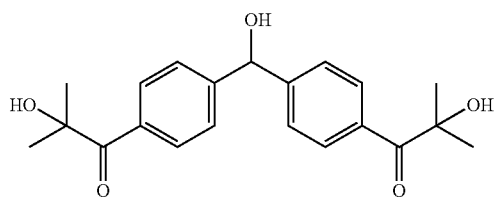

2-hydroxy-1-(4-{hydroxy-[4-(2-hydroxy-2-methyl-propionyl)-phenyl]-methyl}-phenyl)-2-methyl-propan-1-one

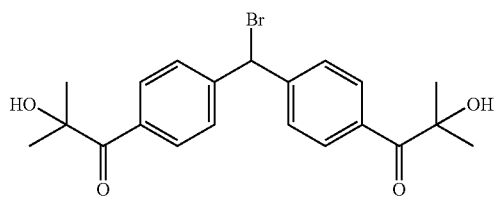

1-(4-{bromo-[4-(2-hydroxy-2-methyl-propionyl)-phenyl]-methyl}-phenyl)-2-hydroxy-2-methyl-propane-1-one

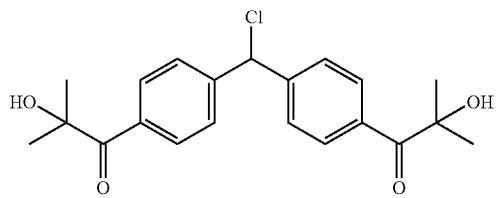

1-(4-{chloro-[4-(2-hydroxy-2-methyl-propionyl)-phenyl]-methyl}-phenyl)-2-hydroxy-2-methyl-propane-1-one

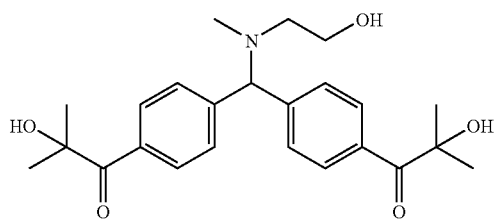

2-hydroxy-1-(4-{[(2-hydroxy-ethyl)-methyl-amino]-[4-(2-hydroxy-2-methyl-propionyl)-phenyl]-methyl}-phenyl)-2-methyl-propane-1-one Preparation of the Compounds:
Preparation of the isomeric mixture is carried out in accordance with the following scheme:
a) reaction of diphenylmethane with an acid halide of formula $R_1R_2CH$—COHal and, optionally, further reaction with an acid halide of formula $R_3R_4CH$—COHal in the presence of a Friedel-Crafts catalyst, whereupon an isomeric mixture of formula A is obtained,

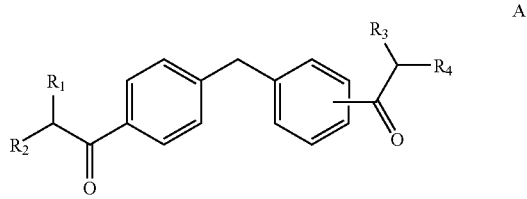

b) halogenation of the isomeric mixture of formula A, followed by bromination and hydrolysis, whereupon an isomeric mixture of formula B is obtained,

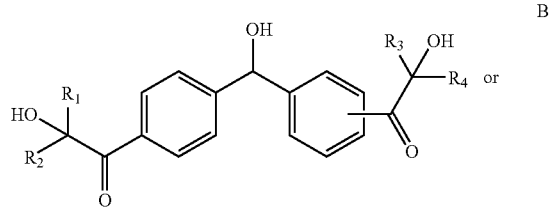

b') halogenation of the isomeric mixture of formula A, followed by bromination, aminolysis of the benzylic bromide, and hydrolysis of the tertiary halides, whereupon an isomeric mixture of formula C is obtained

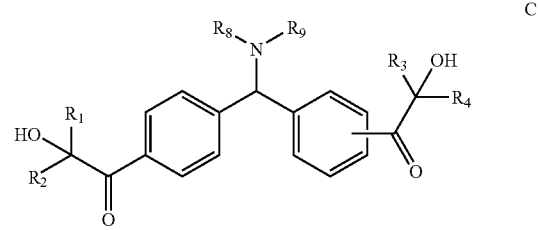

c) optionally, selective substitution of the benzylic hydroxy group in the resulting isomeric mixture of formula B by reaction
with an alcohol in the presence of an acid as catalyst for the preparation of an ether,
with a carboxylic acid for the preparation of an ester,
with an isocyanate for the preparation of a urethane,
with a diol, dicarboxylic acid or diisocyanate for the preparation of a bridged compound,
with a diisocyanate together with a diol or a diamine,
with a siloxane for the preparation of a silicone derivative; or
c') optionally, when $R_8$ or $R_9$ in the isomeric mixture of formula C possess a primary hydroxy group, selective substitution of the primary hydroxy group by reaction
with a carboxylic acid for the preparation of an ester,
with an isocyanate for the preparation of a urethane, with a dicarboxylic acid or diisocyanate for the preparation of a bridged compound,
with a siloxane for the preparation of a silicone derivative
d) optionally, reaction of the alpha-hydroxy group in the resulting isomeric mixture of formula B,
e) optionally, separation of the isomers.

Compound B above is both a suitable photoinitiator and an important intermediate for further reactions.

The preparation of the ketone is carried out by Friedel-Crafts acylation, diphenylmethane being reacted in the presence of a Lewis acid, for example with isobutyric acid halide. The known Friedel-Crafts catalysts are suitable, for example aluminium chloride, aluminium bromide, zinc chloride, tin chloride, iron(III) chloride, bismuth chloride or boron trifluoride. Aluminium chloride is preferred In the present Friedel-Crafts reaction, it is possible to bring the aromatic compound and the catalyst together first and to add the acid halide thereto, as described in German Offenlegungsschrift DE 30 08 411 A1 (1980) of Merck.

It is, however, also possible to bring the aromatic compound and the acid halide together first and to add the catalyst.

It has been found that the sequence of addition of the reagents is important for the success of the reaction. The best yields are obtained when the aromatic compound and the acid halide are brought together first and the catalyst, preferably aluminium chloride, is slowly metered in.

Suitable solvents are any solvents that are inert under the indicated reaction conditions, for example ethylene chloride, trichloroethylene, methylene chloride, tetrachloroethane, chloro-benzene, bromobenzene, dichlorobenzene, cyclohexane, methylcyclohexane, carbon disulfide, nitromethane, nitroethane, nitropropane and nitrobenzene. Preference is given to chlorobenzene or ortho-dichlorobenzene.

The reaction temperature is from –20° C. to 20° C., preferably from 0° C. to 10° C., especially from 0° C. to 5° C.

For the reaction there is used an excess of acid halide, relative to diphenylmethane, of from 1.8 to 2.8 equivalents, preferably from 2.0 to 2.6 equivalents, especially from 2.2 to 2.4 equivalents. Acid chloride is preferred to acid bromide.

For the reaction there is used an excess of aluminium chloride, relative to diphenylmethane, of from 1.9 to 2.9 equivalents, preferably from 2.0 to 2.7 equivalents, especially from 2.3 to 2.5 equivalents. The excess of aluminium chloride should be at least as great as the excess of acid halide.

In a further variant, the aluminium chloride may be brought together with the solvent first, and the acid halide may be added dropwise in excess at from –20° C. to 10° C., with cooling. The aromatic compound may then slowly be metered in at from –20° C. to 10° C., with cooling.

The ketone of step (a) is obtained in the form of an isomeric mixture and can be directly subjected, in step (b), to enol halogenation, preferably enol chlorination, and subsequent bromination without being isolated. Bromination may also be carried out by means of free radicals, with light acting as free-radical-former. It is, however, also possible to use customary free-radical-formers such as dibenzoyl peroxide or azoisobutyronitrile.

Subsequent hydrolysis with aqueous alkali metal hydroxide (step c) yields the crude isomeric mixture, dissolved in the organic phase.

The benzylic hydroxy group is capable of being substituted and can be reacted selectively, for example,
with an alcohol in the presence of an acid as catalyst for the preparation of an ether,
with a carboxylic acid for the preparation of an ester,
with an isocyanate for the preparation of a urethane,
with a siloxane for the preparation of a silicone derivative,
with a diol, dicarboxylic acid or diisocyanate for the preparation of a bridged compound;
with a diisocyanate together with a diol or a diamine,
suitable diols, diisocyanates and siloxanes are indicated in the above list.

The reaction of alpha hydroxy groups can be carried out in accordance with known methods such as those described in, for example, EP-A 003 002, EP 138 754 B1 or U.S. Pat. No. 5,977,357. European Patent Application EP-A 003 002 describes the use of specific ketones as photoinitiators. The ketones have a tertiary alpha carbon atom which is substituted by a hydroxyl group or an amino group or an etherification or silylation product thereof. European Patent Specification EP 138 754 B1 describes photocurable mixtures containing alpha-amino groups. U.S. Pat. No. 5,977,357 likewise describes the preparation of photoinitiators containing alpha-amino groups.

In order to obtain photoinitiators having a high molecular weight and thus, being non-migratory, the benzylic hydroxy group can be substituted by diisocyanates or by diisocyanates together with diols or with diamines to obtain the following structures:

$(Ar)_2$—CH—O—CO—NH—R—NH—CO—O—CH—$(Ar)_2$ $(Ar)_2$—CH—O—CO—NH—R—NH—CO—O—R'—O—CO—NH—R—NH—CO—O—CH—$(Ar)_2$ $(Ar)_2$—CH—O—CO—NH—R—NH—CO—NH—R"—NH—CO—NH—R—NH—CO—O—CH—$(Ar)_2$

The photoinitiator of the formula I or II may be covalently bonded to the resin system used, thus being non migratory and especially suitable for food packaging.

The reaction between the alcohol and the isocyanate is carried out using known catalysts, such as tert. amines, DABCO and Sn-catalysts. Such catalysts are e.g. described Houben-Weyl, E4, p. 182 ff. (1983).

Suitable amines are:

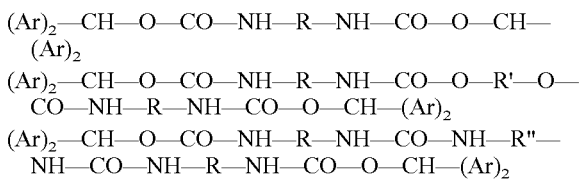

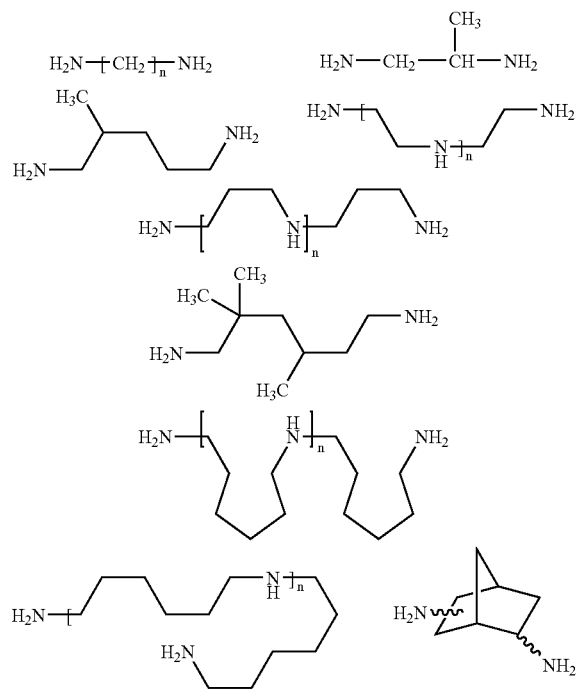

-continued

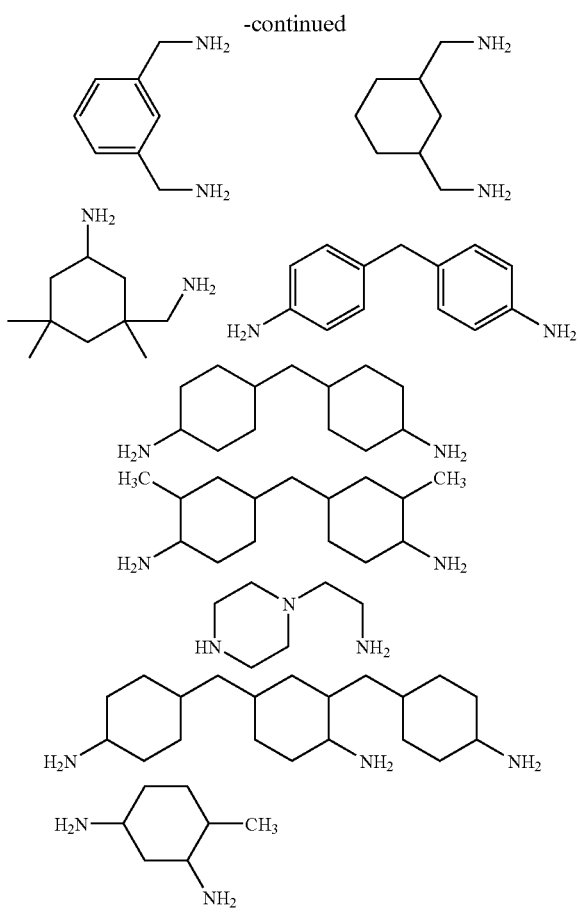

When preparing the substances, mixtures are often to be expected: mono-, bis-, tris-, tetra-derivatives etc. and also para-para and meta-para structures.

The novel compounds of formulae I and II are very generally suitable as photoinitiators.

The invention accordingly relates also to a composition consisting of
(A) at least one ethylenically unsaturated compound,
(B) a photoinitiator of formula I, II, III, IV, V, VI, VII, VIII, IX, or X
(C) optionally, further additives,
(D) optionally, further photoinitiators and coinitiators.

Suitable Ethylenically Unsaturated Compound (A)

The unsaturated compounds (A) may contain one or more olefinic double bonds. They may be low molecular weight (monomeric) or higher molecular weight (oligomeric). Examples of monomers containing a double bond are (meth)acrylic acid and salts thereof,
(meth)acrylic acid esters, e.g. alkyl esters such as methyl, ethyl, 2-chloroethyl, N-dimethyl-aminoethyl, n-butyl, isobutyl, pentyl, hexyl, cyclohexyl, 2-ethylhexyl, octyl, isobornyl [2-exo-bornyl]ester,
phenyl, benzyl and o-, m- and p-hydroxyphenyl ester,
hydroxyalkyl esters, e.g. 2-hydroxyethyl, 2-hydroxypropyl, 4-hydroxybutyl, 3,4-dihydroxy-butyl or glycerol [1,2,3-propanetriol]ester,
epoxyalkyl esters, e.g. glycidyl, 2,3-epoxybutyl, 3,4-epoxybutyl, 2,3-epoxycyclohexyl, 10,11-epoxyundecyl ester,
(meth)acrylamides, N-substituted (meth)acrylamides, e.g. N-methylolacrylamide, N-methylolmethacrylamide, N-ethylacrylamide, N-ethylmethacrylamide, N-hexylacrylamide, N-hexylmethacrylamide, N-cyclohexylacrylamide, N-cyclohexylmethacrylamide, N-hydroxyethylacrylamide, N-phenylacrylamide, N-phenylmethacrylamide, N-benzylacrylamide, N-benzylmethacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide and N-(4-hydroxyphenyl)methacrylamide, IBMM (N-isobutoxymethylacrylamide), (meth)acrylonitriles,
unsaturated acid anhydrides such as itaconic anhydride, maleic anhydride, 2,3-dimethylmaleic anhydride, 2-chloromaleic anhydride,
unsaturated esters such as maleic acid esters, phthalic acid esters, itaconic acid esters [methylenesuccinic acid esters],
styrenes such as methylstyrene, chloromethylstyrene and o-, m- and p-hydroxystyrene, divinylbenzene,
vinyl ethers such as isobutyl vinyl ether, ethyl vinyl ether, 2-chloroethyl vinyl ether, hydroxyethyl vinyl ether, propyl vinyl ether, butyl vinyl ether, isobutyl vinyl ether, octyl vinyl ether and phenyl vinyl ether,
vinyl and allyl esters such as vinyl acetate, vinyl acrylate, vinyl chloroacetate, vinyl butyrate and vinyl benzoate, divinyl succinate, diallyl phthalate, triallyl phosphate,
vinyl chloride and vinylidene chloride,
isocyanurates such as triallyl isocyanurate and tris(2-acryloylethyl)isocyanurate,
N-vinyl-heterocyclic compounds such as N-vinylpyrrolidones or substituted N-vinylpyrrolidones, N-vinylcaprolactam or substituted N-vinylcaprolactams, N-vinylcarbazole, N-vinylpyridine.

Further examples of suitable esters are:
diacrylate esters such as 1,6-hexanediol diacrylate (HDDA), ethylene glycol diacrylate, propylene glycol diacrylate, dipropylene glycol diacrylate, tripropylene glycol diacrylate, neopentyl glycol diacrylate, hexamethylene glycol diacrylate and bisphenol A diacrylate, trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having molecular weights of from 200 to 1500, or mixtures thereof.

There are frequently also used acrylic acid esters of alkoxylated alcohols, e.g. glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Examples of higher-molecular-weight unsaturated compounds (oligomers, prepolymers) are esters of ethylenically unsaturated mono- or poly-functional carboxylic acids and polyols or polyepoxides, and polymers having ethylenically unsaturated groups in the chain or in side groups such as, for example, unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more of such polymers.

Examples of suitable mono- or poly-functional unsaturated carboxylic acids are acrylic acid, methacrylic acid, crotonic acid, cinnamic acid, maleic acid, fumaric acid, itaconic acid, un-saturated fatty acids such as linolenic acid or oleic acid. Acrylic and methacrylic acid are preferred.

However, saturated di- or poly-carboxylic acids in admixture with unsaturated carboxylic acids may also be used. Examples of suitable saturated di- or poly-carboxylic acids include, for example, tetrachlorophthalic acid, tetrabromophthalic acid, phthalic anhydride, adipic acid, tetrahydrophthalic acid, isophthalic acid, terephthalic acid, trimellitic acid, heptane-dicarboxylic acid, sebacic acid; dodecanedicarboxylic acid, hexahydrophthalic acid etc.

As polyols, aromatic and especially aliphatic and cycloaliphatic polyols are suitable. Examples of aromatic polyols are hydroquinone, 4,4'-dihydroxydiphenyl, 2,2-di(4-hydroxy-phenyl)propane, and also novolaks and resols. Examples of polyepoxides are those based on the mentioned polyols, especially aromatic polyols and epichlorohydrin. Also suitable as polyols are polymers and copolymers that contain hydroxyl groups in the polymer chain or in side groups such as, for example, polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Examples of polyurethanes are those composed of saturated diisocyanates and unsaturated diols or unsaturated diisocyanates and saturated diols.

Preference is given to methacrylated epoxy esters, methacrylated polyesters, polyesters carrying vinyl groups, methacrylated polyurethanes, methacrylated polyethers and polyols.

Suitable components (A) are also acrylates which have been modified by reaction with primary or secondary amines, as described, for example, in U.S. Pat. No. 3,844,916 of Gaske, in EP 280 222 of Weiss et al., in U.S. Pat. No. 5,482, 649 of Meixner et al. or in U.S. Pat. No. 5,734,002 of Reich et al. Such amine-modified acrylates are also termed amine acrylates. Amine acrylates are obtainable, for example, under the name EBECRYL 80, EBECRYL 81, EBECRYL 83, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley and GENOMER 5275 from Rahn.

Furthermore, cationically UV-curable compositions may be used as component (A). Such systems typically comprise aliphatic and/or aromatic epoxides, at least one polyol or polyvinyl polyol and also at least one photoinitiator that generates cations. The said epoxides, polyols and polyvinyl polyols are known in the art and commercially available. The customarily used photoinitiators are iodonium and sulfonium salts as described, for example, in U.S. Pat. No. 6,306,555.

In addition, ethylenically unsaturated compounds may be added to the said cationically UV-curable compositions It is also possible to add solvents or water to the compositions used in the process according to the invention. Suitable solvents are solvents which are known to the person skilled in the art and are conventional especially in surface-coating technology. Examples are various organic solvents such as, for example, ketones, e.g. methyl ethyl ketone, cyclohexanone; aromatic hydrocarbons, e.g. toluene, xylene or tetramethylbenzene; glycol ethers, e.g. diethylene glycol monoethyl ether, dipropylene glycol diethyl ether; esters, e.g. ethyl acetate; aliphatic hydrocarbons, e.g. hexane, octane, decane; or petroleum solvents, e.g. petroleum ether.

The invention relates also to compositions comprising, as component (A), at least one ethylenically unsaturated photopolymerisable compound dissolved or emulsified in water. Such radiation-curable aqueous prepolymer dispersions are obtainable commercially in many variations. They are to be understood as being a dispersion consisting of water and at least one prepolymer dispersed therein. The concentration of the water in those systems is, for example, from 5 to 80% by weight, especially from 30 to 60% by weight. The radiation-curable prepolymer or prepolymer mixture is present in concentrations of, for example, from 95 to 20% by weight, especially from 70 to 40% by weight. The sum of the indicated percentages for water and prepolymer in those compositions is in each case 100; auxiliaries and additives, which are present in varying amounts depending on the intended use, are in addition thereto.

The radiation-curable film-forming prepolymers, which are dispersed or in many cases dissolved in water, are mono- or poly-functional ethylenically unsaturated prepolymers capable of initiation by free radicals and known per se for aqueous prepolymer dispersions; for example, they have a content of from 0.01 to 1.0 mol of polymerisable double bonds per 100 g of prepolymer and an average molecular weight of, for example, at least 400, especially from 500 to 10 000, although depending on the intended use prepolymers having higher molecular weights also come into consideration.

There are used, for example, polyesters containing polymerisable C—C double bonds and having an acid number of at most 10, polyethers containing polymerisable C—C double bonds, hydroxyl-group-containing reaction products of a polyepoxide containing at least two epoxide groups per molecule with at least one α,β-ethylenically unsaturated carboxylic acid, polyurethane (meth)acrylates and also acrylic copolymers containing α,β-ethylenically unsaturated acrylic radicals as described, for example, in EP 012 339. Mixtures of those prepolymers may also be used. Also suitable are, for example, the polymerisable prepolymers described in EP 033 896, which are thioether adducts of polymerisable prepolymers having an average molecular weight of at least 600, a carboxyl group content of from 0.2 to 15% and a content of from 0.01 to 0.8 mol of polymerisable C—C double bonds per 100 g of prepolymer. Other suitable aqueous dispersions based on particular (meth)acrylic acid alkyl ester polymerisation products are described in EP 041 125; suitable water-dispersible, radiation-curable prepolymers obtained from urethane acrylates are to be found in, for example, DE 2 936 039.

When compound (A) is a resin containing free OH groups, the benzylic or benzhydrylic hydroxy group of the compound of formula I can be bonded to the uncured or cured resin by etherification. That procedure can be accelerated by means of (lamp) heat or trace amounts of acid.

Such resins are, for example, epoxy acrylates obtained from glycidyl ethers and acrylates, acrylates with diols and polyols such as, for example, pentaerythritol triacrylate, or hydroxylated polyesters such as trimethylolpropane/polycaprolactone (trade names: Capa 301; Capa 305; Capa 310; Niax PCP 0300; Niax Polyol PCP 0300; PCL 305; PCP 0300; Placcel 305; Placcel 312; polycaprolactone, sru, ester with trimethylolpropane; T 301; Tone 030; Tone 0301).

Further examples are OTA480 from UCB and Photomer 4094 from Cognis.

When compound (A) is a resin containing free isocyanate groups, the benzylic or benzhydrylic hydroxy group of the compound of formula I can likewise be bonded to the uncured or cured resin by urethane formation.

When compound (A) is a resin containing free carboxyl groups, the benzylic or benzhydrylic hydroxy group of the compound of formula I can likewise be bonded to the uncured or cured resin by esterification. Such a resin is, for example, Photomer 5429.

There are accordingly obtained compositions without migration of the photoinitiator. The use of photoinitiators without or with a very low level of migration is important especially in the case of compositions that are used for food packaging.

The photopolymerisable compounds (A) may be used singly or in any desired mixture. Preference is given to the use of mixtures of polyol(meth)acrylates.

Component (A) may also comprise binders, that being especially advantageous when the photopolymerisable compounds are liquid or viscous substances. The amount of the binder may be, for example, from 5 to 95% by weight, preferably from 10 to 90% by weight and especially from 40 to 90% by weight, based on the total solid material. The binder is selected according to the field of use and the properties required therefor such as, for example, developability in aqueous and organic solvent systems, adhesion to substrates and sensitivity to oxygen.

Suitable binders are, for example, polymers having molecular weights of about 5 000-2 000 000, preferably 10 000-1 000 000. Examples are: homo- and co-polymers of acrylates and methacrylates, e.g. copolymers of methyl methacrylate/ethyl acrylate/meth-acrylic acid, poly(methacrylic acid alkyl esters), poly(acrylic acid alkyl esters); cellulose esters and ethers, e.g. cellulose acetate, cellulose acetate butyrate, methylcellulose, ethylcellulose; polyvinyl butyral, polyvinyl formal, cyclised rubber, polyethers, e.g. polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers, e.g. polycaprolactam und poly(hexamethylene adipamide), polyesters, e.g. poly(ethylene glycol terephthalate) and poly(hexamethylene glycol succinate).

The unsaturated compounds may also be used in admixture with non-photopolymerisable film-forming components. The latter may be, for example, physically drying polymers or solutions thereof in organic solvents, e.g. nitrocellulose or cellulose acetobutyrate, but may also be chemically or thermally curable resins, e.g. polyisocyanates, polyepoxides or melamine resins. Melamine resins are to be understood as including not only condensation products of melamine (=1, 3,5-triazine-2,4,6-triamine) but also those of melamine derivatives. In general, the binder is a film-forming binder based on a thermoplastic or thermocurable resin, mainly a thermocurable resin. Examples thereof are alkyd, acrylic, polyester, phenol, melamine, epoxy and polyurethane resins and mixtures thereof. The concomitant use of thermally curable resins is of importance for use in so-called hybrid systems, which are both photopolymerised and also thermally crosslinked.

Component (A) may also comprise film-forming binders based on a thermoplastic or thermocurable resin, mainly a thermocurable resin. Examples thereof are alkyd, acrylic, polyester, phenol, melamine, epoxy and polyurethane resins and mixtures thereof. Examples thereof are described in, for example, Ullmann's Encyclopedia of Industrial Chemistry, 5th Ed., Vol. A18, pp. 368-426, VCH, Weinheim 1991.

The binder may be a binder that fully cures at cold or hot temperatures, for which the addition of a curing catalyst may be advantageous. Suitable catalysts which accelerate full curing of the binder are described in, for example, Ullmann's Encyclopedia of Industrial Chemistry, Vol. A18, p. 469, VCH Verlagsgesellschaft, Weinheim 1991.

WO99/03930; WO2000/010974 and WO2000/020517 of DSM describe maleimide-modified binders. Maleimide-modified binders of that kind may likewise be present.

Particular binders are:

1. surface-coatings based on cold- or hot-crosslinkable alkyd, acrylate, polyester, epoxy or melamine resins or mixtures of such resins, optionally with the addition of a curing catalyst;

2. two-component polyurethane surface-coating compositions based on hydroxyl-group-containing acrylate, polyester or polyether resins and aliphatic or aromatic isocyanates, isocyanurates or polyisocyanates;

3. two-component polyurethane surface-coating compositions based on thiol-group-containing acrylate, polyester or polyether resins and aliphatic or aromatic isocyanates, isocyanurates or polyisocyanates;

4. single-component polyurethane surface-coating compositions based on blocked isocyanates, isocyanurates or polyisocyanates, which are unblocked during stoving; optionally, the addition of melamine resins is also possible;

5. single-component polyurethane surface-coating compositions based on aliphatic or aromatic urethanes or polyurethanes and hydroxyl-group-containing acrylate, polyester or polyether resins;

6. single-component polyurethane surface-coating compositions based on aliphatic or aromatic urethane acrylates or polyurethane acrylates having free amine groups in the urethane structure, and melamine resins or polyether resins, optionally with the addition of a curing catalyst;

7. two-component surface-coating compositions based on (poly)ketimines and aliphatic or aromatic isocyanates, isocyanurates or polyisocyanates;

8. two-component surface-coating compositions based on (poly)ketimines and an unsaturated acrylate resin or a polyacetoacetate resin or a methacrylamidoglycolate methyl ester;

9. two-component surface-coating compositions based on carboxyl- or amino-group-containing polyacrylates and polyepoxides;

10. two-component surface-coating compositions based on anhydride-group-containing acrylate resins and a polyhydroxy or polyamino component;

11. two-component surface-coating compositions based on acrylate-containing anhydrides and polyepoxides;

12. two-component surface-coating compositions based on (poly)oxazolines and anhydride-group-containing acrylate resins or unsaturated acrylate resins or aliphatic or aromatic isocyanates, isocyanurates or polyisocyanates;

13. two-component surface-coating compositions based on unsaturated (poly)acrylates and (poly)malonates;

14. thermoplastic polyacrylate surface-coating compositions based on thermoplastic acrylate resins or extrinsically crosslinking acrylate resins, in combination with etherified melamine resins;

15. surface-coating systems, especially clearcoats, based on malonate-blocked isocyanates with melamine resins (e.g. hexamethoxymethyl melamine) as crosslinkers (acid-catalysed);

16. UV-curable systems based on oligomeric urethane acrylates and/or acylate acrylates, optionally with the addition of other oligomers or monomers;

17. dual-cure systems, which are first cured thermally and then UV-cured, or vice versa, wherein constituents of the surface-coating composition contain double bonds which can be made to react by UV light and photoinitiators and/or by electron-beam curing.

Both 1-component (1C) and 2-component (2C) systems may be used as binder. Examples of such systems are described in Ullmann's Encyclopedia of Industrial Chemistry, Vol. A18, Paints and Coatings, page 404-407, VCH Verlagsgesellschaft mbH, Weinheim (1991).

The composition can be optimised by specifically modifying the formulation, e.g. by varying the binder/crosslinker ratio. The person skilled in the art of surface-coating technology will be familiar with such measures.

Additives (C)

In addition to the photoinitiator, the photopolymerisable mixtures may comprise various additives (C). Examples thereof are thermal inhibitors, which are intended to prevent premature polymerisation, e.g. 2,2,6,6-tetramethyl-4-hydroxy-piperidin-1-oxyl (4-hydroxy-TEMPO) and derivatives thereof, e.g. bis(2,2,6,6-tetramethylpiperidin-1-oxyl-4-yl)-decanedioate or polyalkyl-piperidin-N-oxyl radicals, 3-arylbenzofuran-2-one and derivatives thereof, e.g. 5,7-di-tert-butyl-3-phenyl-3H-benzofuran-2-one (as described in, for example, WO 01/42313), hydroquinone, hydroquinone derivatives, p-methoxyphenol, β-naphthol or sterically hindered phenols, e.g. 2,6-di(tert-butyl)-p-cresol. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N-diethylhydroxylamine. For the purpose of excluding atmospheric oxygen during polymerisation it is possible to add paraffin or similar wax-like substances which, being insoluble in the polymer, migrate to the surface at the beginning of the polymerisation and form a transparent surface layer which prevents air from entering. Equally possible is the application of a layer that is impermeable to oxygen.

As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS).

Examples of such UV absorbers and light stabilisers are 1. 2-(2'-Hydroxyphenyl)-benzotriazoles, for example 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)-phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxy-phenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis(α,α-dimethylbenzyl)-2'-hydroxyphenyl)-benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methyl-phenyl)-benzotriazole, 2-(3'-tert-butyl-2'-hydroxy-5'-(2-isooctyloxycarbonylethyl)-phenyl-benzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]-benzotriazole with polyethylene glycol 300; [R—CH$_2$CH$_2$COO—CH$_2$CH$_2$]$_2$— wherein R=3'-tert-butyl-4'-hydroxy-5'-2H-benzotriazol-2-yl-phenyl; 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]-benzotriazole.

2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.

3. Esters of unsubstituted or substituted benzoic acids, for example 4-tert-butyl-phenyl salicylate, phenyl salicylate, octylphenyl salicylate, dibenzoylresorcinol, bis(4-ert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.

4. Acrylates, for example α-cyano-β,β-diphenylacrylic acid ethyl ester or isooctyl ester, α-methoxycarbonylcinnamic acid methyl ester, α-cyano-β-methyl-β-methoxycinnamic acid methyl ester or butyl ester, α-methoxycarbonyl-p-methoxycinnamic acid methyl ester, N-(β-methoxycarbonyl-β-cyanovinyl)-2-methyl-indoline.

5. Sterically hindered amines, for example bis(2,2,6,6-tetramethylpiperidin-4-yl)sebacate, bis(2,2,6,6-tetramethylpiperid-4-yl)succinate, bis(1,2,2,6,6-pentamethylpiperidin-4-yl)sebacate, bis(1-octyloxy-2,2,6,6-tetramethylpiperidin-4-yl)sebacate, n-butyl-3,5-di-tert-butyl-4- hydroxybenzylmalonic acid bis(1,2,2,6,6-pentamethylpiperidyl)ester, condensation product of 1-hydroxyethyl-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetra(2,2,6,6-tetramethylpiperidin-4-yl)-butane-1,2,3,4-tetracarboxylate, tetra-(1,2,2,6,6-pentamethylpiperidin-4-yl)-butane-1,2,3,4-tetracarboxylate, 1,1'-(1,2-ethane-diyl)bis(3,3,5,5-tetramethylpiperazinone), 4-benzoyl-2,2,6,6-tetramethylpiperidine, 4-stearyl-oxy-2,2,6,6-tetramethylpiperidine, bis(1,2,2,6,6-pentamethylpiperidyl)-2-n-butyl-2-(2-hydroxy-3,5di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetra-methylpiperidyl)succinate, linear or cyclic condensation products of N,N'-bis(2,2,6,6-tetramethyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro4,6-di(4-n-butylamino-1,2,2,6,6-pentamethylpiperidyl)-1,3,5-triazine and 1,2-bis(3-aminopropyl-amino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 2,2,4,4-tetramethyl-7-oxa-3,20-diaza-21-oxo-dispiro[5.1.11.2]heneicosane, 8-acetyl-3-dodecyl-1,3,8-triaza-7,7,9,9-tetramethylspiro[4.5]decane-2,4-dione, 1,1-bis(1,2,2,6,6-pentamethylpiperidin-4-yl-oxy-carbonyl)-2-(4-methoxyphenyl)-ethene, 3-dodecyl-1-(1,2,2,6,6-pentamethyl-4-piperidyl)-pyrrolidine-2,5-dione, mixture of 4-hexadecyloxy- and 4-stearyloxy-2,2,6,6-tetramethylpiperidine, condensation product of N,N'-bis(2,2,6,6-tetramethyl-4-piperidyl)hexamethylenediamine and 4-cyclohexylamino-2,6-dichloro-1,3,5-triazine, condensation product of 1,2-bis(3-aminopropylamino)ethane and 2,4,6-trichloro-1,3,5-triazine and 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4.5]decane, reaction product of 7,7,9,9-tetramethyl-2-cycloundecyl-1-oxa-3,8-diaza-4-oxospiro[4.5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxymethylenemalonic acid with 1,2,2,6,6-pentamethyl-4-hydroxypiperidine, poly[methyl-propyl-3-oxy-4-(2,2,6,6-tetramethyl-4-piperidyl)]siloxane, reaction product of maleic anhydride α-olefin copolymer and 2,2,6,6-tetramethyl-4-aminopiperidine or 1,2,2,6,6-pentamethyl-4-aminopiperidine.

6. Oxalic acid diamides, for example 4,4'-dioctyloxy oxanilide, 2,2'-diethoxy oxanilide, 2,2'-dioctyloxy-5,5'-di-tert-butyl oxanilide, 2,2'-didodecyloxy-5,5'-di-tert-butyl oxanilide, 2-ethoxy-2'-ethyl oxanilide, N,N'-bis(3-dimethylaminopropyl)oxalamide, 2-ethoxy-5-tert-butyl-2'-ethyl oxanilide and a mixture thereof with 2-ethoxy-2'-ethyl-5,4'-di-tert-butyl oxanilide, mixtures of o- and p-methoxy- and also of o- and p-ethoxy-di-substituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethyl-phenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethyl-phenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)-phenyl]-4,6-bis(2,4-dimethylphenyl)-1,3,5-triazine, 2-(2-hydroxy-4-hexyloxy)phenyl-4,6-di-phenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxy-propyloxy]phenyl}-4,6-bis(2,4-dimethylphenyl)-1,3,5-triazine.

8. Phosphites and phosphonites, e.g. triphenyl phosphite, diphenylalkyl phosphites, phenyldialkyl phosphites, tris(nonylphenyl)phosphite, trilauryl phosphite, trioctadecyl phosphite, distearyl-pentaerythritol diphosphite, tris(2,4-di-tert-butylphenyl)phosphite, diisodecylpentaerythritol diphosphite, bis(2,4-di-tert-butylphenyl)pentaerythritol diphosphite, bis(2,6-di-tert-butyl-4-methylphenyl)pentaerythritol diphosphite, bis-isodecyloxy-pentaerythritol diphosphite, bis(2,4-di-tert-butyl-6-methylphenyl)pentaerythritol diphosphite, bis(2,4,6-tri-tert-butylphenyl)-pentaerythritol diphosphite, tristearyl sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, bis(2,4-di-tert-butyl-6-methylphenyl)methylphosphite, bis(2,4-di-tert-butyl-6-methylphenyl)ethylphosphite, 6-fluoro-2,4,8,10-tetra-tert-butyl-12-methyl-dibenzo[d,g]-1,3,2-dioxaphosphocine, 2,2',2"-nitrilo[triethyl-tris(3,3',5,5'-tetra-tert-butyl-1,1'-biphenyl-2,2'-diyl)-phosphite], 2-ethylhexyl-(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

In addition, additives that are customary in the art such as, for example, antistatics, flow improvers and adhesion promoters may be used.

In accordance with the invention, if the formulation comprises binder, thermal drying or curing catalysts may additionally be added to the formulation as additional additives (C). Possible drying catalysts, or thermal curing catalysts, are, for example, organic metal compounds, amines or/and phosphines. Organic metal compounds are, for example, metal carboxylates, especially those of the metals Pb, Mn, Hf, Co, Zn, Zr or Cu, or metal chelates, especially those of the metals Hf, Al, Ti or Zr, or organometal compounds, such as e.g. organotin compounds. Examples of metal carboxylates are the stearates of Pb, Mn or Zn, the octoates of Co, Zn or Cu, the naphthenates of Mn and Co or the corresponding linoleates or tallates (tall oil, which contains rosin acids, oleic and linoleic acids). Examples of metal chelates are the aluminium, titanium or zirconium chelates of acetyl acetone, ethylacetyl acetate, salicylaldehyde, salicylaldoxime, o-hydroxyacetophenone or ethyl-trifluoroacetyl acetate and the alkoxides of those metals. Examples of organotin compounds are dibutyltin oxide, dibutyltin dilaurate and dibutyltin dioctoate. Examples of amines are especially tertiary amines such as, for example, tributylamine, triethanolamine, N-methyldiethanolamine, N-dimethylethanolamine, N-ethylmorpholine, N-methylmorpholine and diazabicyclooctane (triethylenediamine) and the salts thereof. Further examples are quaternary ammonium salts, such as e.g. trimethylbenzylammonium chloride. It is also possible to use phosphines such as, for example, triphenylphosphine, as curing catalysts. Suitable catalysts are also described in, for example, J. Bielemann, Lackadditive, Wiley-VCH Verlag GmbH, Weinheim, 1998, pages 244-247. Examples are carboxylic acids such as, for example, p-toluenesulfonic acid, dodecylbenzenesulfonic acid, dinonylnaphthalenesulfonic acid and dinonylnaphthalenedisulfonic acid. There may also be used, for example, latent or blocked sulfonic acids, it being possible for the blocking of the acid to be ionic or non-ionic. Such catalysts are used in concentrations customary in the art and known to the skilled person.

In order to accelerate photopolymerisation, amines may be added as further additives (C), especially tertiary amines, e.g. tributylamine, triethanolamine, p-dimethylaminobenzoic acid ethyl ester, Michler's ketone, N-methyl-diethanolamine, N-dimethylethanolamine, N-ethylmorpholine, N-methylmorpholine, diazabicyclooctane (triethylenediamine), 18-diazabicyclo-[5.4.0]undec-7-ene (DBU), 1,5-diazabicyclo[4.3.0]non-5-ene (DBN) and salts thereof. Further examples are quaternary ammonium salts, e.g. trimethylbenzylammonium chloride. The action of the amines may be reinforced by adding aromatic ketones of the benzophenone type. Amines that are suitable as oxygen capture agents are, for example, N,N-dialkylanilines as described in EP 339 841. Further accelerators, coinitiators and auto-oxidisers are thiols, thioethers, disulfides and phosphines as described in, for example, EP 438 123 and GB 2 180 358.

It is also possible for chain transfer reagents customary in the art to be added to the compositions according to the invention. Examples are mercaptans, amines and benzothiazole.

Photopolymerisation can also be accelerated by addition, as further additives (C), of photosensitisers, which shift or broaden the spectral sensitivity. These include especially aromatic carbonyl compounds such as, for example, benzophenone derivatives, thioxanthone derivatives, including especially isopropyl thioxanthone, anthraquinone derivatives and 3-acylcoumarin derivatives, terphenyls, styryl ketones, and 3-(aroyl-methylene)-thiazolines, camphorquinone and also eosin, rhodamine and erythrosine dyes. The amines mentioned above, for example, may also be regarded as photosensitisers.

The curing process, especially of pigmented (e.g. pigmented with titanium dioxide) compositions, can also be assisted by adding an additional additive (C) which under thermal conditions is a free-radical-forming component, for example an azo compound, e.g. 2,2'-azobis(4-methoxy-2,4-dimethylvaleronitrile), a triazene, a diazo sulfide, a pentazadiene or a peroxy compound such as a hydroperoxide or peroxycarbonate, e.g. tert-butyl hydroperoxide as described in, for example, EP 245 639.

Further customary additives (C) are—depending on the intended use—fluorescent whitening agents, fillers, e.g. kaolin, talc, barite, gypsum, chalk or silicate-type fillers, wetting agents or flow improvers.

For curing thick and pigmented coatings, the addition of glass microspheres or powdered glass fibres is suitable, as described in, for example, U.S. Pat. No. 5,013,768.

The formulations may also comprise dyes and/or white or coloured pigments. Depending on the intended use, both inorganic and organic pigments may be used. Such additives will be known to the person skilled in the art; a few examples are titanium dioxide pigments, e.g. of the rutile or anatase type, carbon black, zinc oxide, e.g. zinc white, iron oxides, e.g. iron oxide yellow, iron oxide red, chromium yellow, chromium green, nickel titanium yellow, ultramarine blue, cobalt blue, bismuth vanadate, cadmium yellow or cadmium red. Examples of organic pigments are mono- or bis-azo pigments, and also metal complexes thereof, phthalocyanine pigments, polycyclic pigments, e.g. perylene, anthraquinone, thioindigo, quin-acridone or triphenylmethane pigments, and also diketo-pyrrolo-pyrrole, isoindolinone, e.g. tetrachloroisoindolinone, isoindoline, dioxazine, benzimidazolone and quinophthalone pigments.

The pigments may be used in the formulations singly or in admixture.

The pigments are added to the formulations, in accordance with the intended use, in amounts customary in the art, for example in an amount of from 1 to 60% by weight, or from 10 to 30% by weight, based on the total mass.

The formulations may also comprise, for example, organic dyes from a very wide variety of classes. Examples are azo dyes, methine dyes, anthraquinone dyes or metal complex dyes. Customary concentrations are, for example, from 0.1 to 20%, especially from 1 to 5%, based on the total mass.

Selection of the additives is based on the particular field of use and the properties desired in that field.

The additives (C) described hereinbefore are customary in the art and are accordingly used in amounts customary in the art.

Further Photoinitiators (D)

It is, of course, also possible to use mixtures with known photoinitiators (D), e.g. mixtures with camphorquinone, benzophenone, benzophenone derivatives (e.g. 1-[4-(4-benzoyl-phenylsulfanyl)-phenyl]-2-methyl-2-(toluene-4-sulfonyl)-propan-1-one), acetophenone, acetophenone derivatives, e.g. α-hydroxycycloalkyl phenyl ketones or 2-hydroxy-2-methyl-1-phenyl-propanone, dialkoxyacetophenones, α-hydroxy- or α-amino-acetophenones, e.g. oligo[2-hydroxy-2-methyl-1-[4-(1-methylvinyl)phenyl]-propanone], 2-dimethylamino-2-(4-methyl-benzyl)-1-(4-morpholin-4-yl-phenyl)-butan-1-one, 2-benzyl-2-dimethylamino-1-(4-morpholin-4-yl-phenyl)-butan-1-one, 2-methyl-1-(4-methylsulfanyl-phenyl)-2-morpholin-4-yl-propan-1-one, 4-aroyl-1,3-dioxolanes, benzoin alkyl ethers and benzil ketals, e.g. benzil dimethyl ketal, phenyl glyoxalates and derivatives thereof, e.g. methylbenzoyl formate, dimeric phenyl glyoxalates, e.g. oxo-phenyl-acetic acid 2-[2-(2-oxo-2-phenyl-acetoxy)-ethoxy]-ethyl ester, peresters, e.g. benzophenone-tetracarboxylic acid peresters, as described in, for example, EP 126 541, monoacylphosphine oxides, e.g. (2,4,6-trimethylbenzoyl)-diphenyl-phosphine oxide, bisacylphosphine oxides, e.g. (2,6-dimethoxybenzoyl)-(2,4,4-trimethyl-pent-1-yl)phosphine oxide, bis(2,4,6-trimethylbenzoyl)-phenyl-phosphine oxide or bis(2,4,6-trimethylbenzoyl)-(2,4-dipentyloxyphenyl)phosphine oxide, trisacyl-phosphine oxides, halomethyltriazines, e.g. 2-[2-(4-methoxy-phenyl)-vinyl]-4,6-bis-trichloro-methyl-[1,3,5]triazine 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaarylbisimidazole/coinitiator systems, e.g. ortho-chlorohexaphenyl-bisimidazole together with 2-mercaptobenzthiazole, ferrocenium compounds or titanocenes, e.g. dicyclopentadienyl bis(2,6-difluoro-3-pyrrolo-phenyl)titanium, borate photoinitiators or O-acyloxime photoinitiators, as described in, for example, GB 2 339 571.

Special mention is made of mixtures with the following photoinitiators:

Benzophenones of Formula

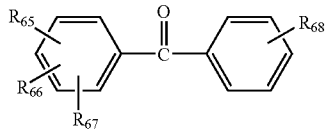

wherein $R_{65}$, $R_{66}$ and $R_{67}$ are each independently of the others hydrogen, $C_1$-$C_4$alkyl, $C_1$-$C_4$haloalkyl, $C_1$-$C_4$alkoxy, chlorine or $N(C_1$-$C_4$alkyl$)_2$;

$R_{68}$ is hydrogen, $C_1$-$C_4$alkyl, $C_1$-$C_4$haloalkyl, phenyl, $N(C_1$-$C_4$-alkyl$)_2$, $COOCH_3$,

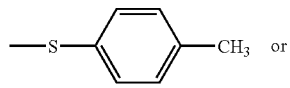

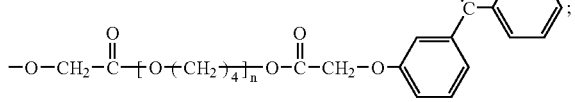

n is an integer of 2-10.

For example:

ESACURE TZT® obtainable from Lamberti, (mixture of 2,4,6-trimethylbenzophenone and 4-methylbenzophenone)

Benzophenone, Darocur® BP

Alpha-hydroxy Ketones, Alpha-alkoxy Ketones or Alpha-amino Ketones of Formula

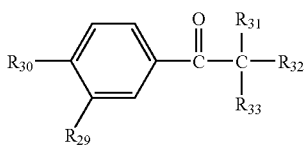

wherein $R_{29}$ is hydrogen or $C_1$-$C_{18}$alkoxy;

$R_{30}$ is hydrogen, $C_1$-$C_{18}$alkyl, $C_1$-$C_{18}$alkoxy, —$OCH_2CH_2$—$OR_{47}$, morpholino, $SCH_3$, one of the following groups

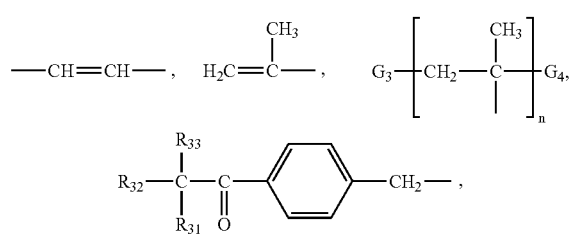

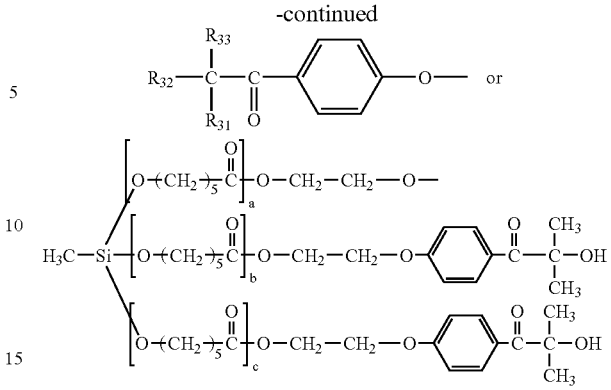

wherein a, b and c=1-3 and n=2-10;

$G_3$ and $G_4$ are each independently of the other terminal groups of polymeric structures, especially hydrogen or methyl;

$R_{47}$ is hydrogen,

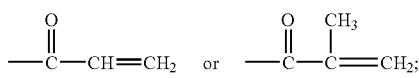

$R_{31}$ is hydroxy, $C_1$-$C_{16}$alkoxy, morpholino, dimethylamino or —$O(CH_2CH_2O)_m$—$C_1$-$C_{16}$alkyl;

$R_{32}$ and $R_{33}$ are each independently of the other hydrogen, $C_1$-$C_6$alkyl, $C_1$-$C_{16}$alkoxy or —$O(CH_2CH_2O)_m$—$C_1$-$C_{16}$alkyl; or unsubstituted phenyl or benzyl, or phenyl or benzyl substituted by $C_1$-$C_{12}$alkyl; or $R_{32}$ and $R_{33}$, together with the carbon atom to which they are bonded, form a cyclohexyl ring;

m is a number from 1 to 20;

$R_{31}$, $R_{32}$ and $R_{33}$ not all simultaneously being $C_1$-$C_{16}$alkoxy or —$O(CH_2CH_2O)_m$—$C_1$-$C_{16}$alkyl.

Examples are:

1-hydroxy-cyclohexyl-phenyl ketone (IRGACURE® 184) or IRGACUR® 500 (a mixture of IRGACURE® 184 with benzophenone);

2-methyl-1-[4-(methylthio)phenyl]-2-morpholinopropan-1-one; (IRGACURE® 907)

2-benzyl-2-dimethylamino-1-(4-morpholinophenyl)-butan-1-one; (IRGACURE® 369)

1-[4-(2-hydroxyethoxy)-phenyl]-2-hydroxy-2-methyl-1-propan-1-one; (IRGACURE® 2959)

2,2-dimethoxy-1,2-diphenylethan-1-one; (IRGACURE® 651)

2-hydroxy-2-methyl-1-phenyl-propan-1-one; (DAROCUR® 1173)

2-dimethylamino-2-(4-methyl-benzyl)-1-(4-morpholin-4-yl-phenyl)-butan-1-one;

2-benzyl-1-(3,4-dimethoxy-phenyl)-2-dimethylamino-butan-1-one;

2-hydroxy-1-{4-[4-(2-hydroxy-2-methyl-propionyl)-benzyl]-phenyl}-2-methyl-propan-1-one;

2-hydroxy-1-{4-[4-(2-hydroxy-2-methyl-propionyl)-phenoxy]-phenyl}-2-methyl-propan-1-one, Irgacure and Darocur are products of Ciba Specialty Chemicals Inc.

Acylphosphine Oxides of Formula

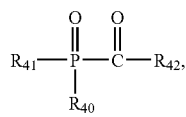
(V)

wherein $R_{40}$ and $R_{41}$ are each independently of the other $C_1$-$C_{20}$alkyl, cyclohexyl, cyclopentyl, phenyl, naphthyl or biphenylyl, those radicals being unsubstituted or substituted by halogen, $C_1$-$C_{12}$alkyl, $C_1$-$C_{12}$alkoxy, $C_1$-$C_1$alkylthio or by $NR_{52}R_{53}$;

$R_{42}$ is cyclohexyl, cyclopentyl, phenyl, naphthyl or biphenylyl, those radicals being unsubstituted or substituted by halogen, $C_1$-$C_4$alkyl or/and by $C_1$-$C_4$alkoxy, or $R_{42}$ is a sulfur- or nitrogen-containing, 5- or 6-membered heterocyclic ring;

$R_{52}$ and $R_{53}$ are each independently of the other hydrogen; $C_1$-$C_{12}$alkyl which is uninterrupted or interrupted by oxygen atoms and which is unsubstituted or substituted by OH or by SH; or $R_{52}$ and $R_{53}$ are $C_2$-$C_{12}$alkenyl, cyclopentyl, cyclohexyl, benzyl or phenyl.

Examples are:
bis(2,4,6-trimethylbenzoyl)-phenylphosphine oxide IRGACURE® 819
2,4,6-trimethylbenzoyl-diphenyl-phosphine oxide; Darocur® TPO
bis(2,6-dimethoxybenzoyl)-2,4,4-trimethyl pentylphosphine oxide Titanocenes of Formula

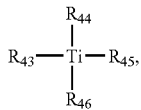
(VI)

wherein $R_{43}$ and $R_{44}$ are each independently of the other cyclopentadienyl which is unsubstituted or mono-, di- or tri-substituted by $C_1$-$C_{18}$alkyl, $C_1$-$C_{18}$alkoxy, cyclopentyl, cyclohexyl or by halogen;

$R_{45}$ and $R_{46}$ are each independently of the other phenyl which, in at least one of the two positions ortho to the titanium-carbon bond, is substituted by fluorine atoms or by $CF_3$ and which may contain as further substituents on the aromatic ring pyrrolinyl or polyoxaalkyl which are unsubstituted or mono- or di-substituted by $C_1$-$C_{12}$alkyl, di($C_1$-$C_{12}$alkyl)amino-methyl, morpholinomethyl, $C_2$-$C_4$alkenyl, methoxymethyl, ethoxymethyl, trimethylsilyl, formyl, methoxy or by phenyl, or $R_{45}$ and $R_{46}$ are

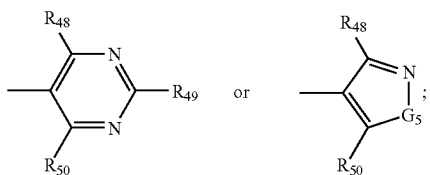

$R_{48}$, $R_{49}$ and $R_{50}$ are each independently of the others hydrogen, halogen, $C_2$-$C_{12}$alkenyl, $C_1$-$C_{12}$alkoxy, $C_2$-$C_{12}$alkoxy interrupted by from one to four oxygen atoms, cyclohexyloxy, cyclopentyloxy, phenoxy, benzyloxy, or phenyl or biphenylyl which are unsubstituted or substituted by $C_1$-$C_4$alkoxy, halogen, phenylthio or by $C_1$-$C_4$alkylthio, $R_{48}$ and $R_{50}$ not both simultaneously being hydrogen and, in the radical

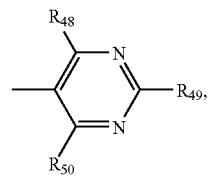

at least one radical $R_{48}$ or $R_{50}$ being $C_1$-$C_{12}$alkoxy, $C_2$-$C_{12}$alkoxy interrupted by from one to four oxygen atoms, cyclohexyloxy, cyclopentyloxy, phenoxy or benzyloxy;

$G_5$ is O, S or $NR_{51}$; and $R_{51}$ is $C_1$-$C_8$alkyl, phenyl or cyclohexyl.

Examples are
bis(eta-5,2,4-cyclopentadien-1-yl)-bis(2,6-difluoro-3-(1H-pyrrol-1-yl)-phenyl)titanium IRGACURE® 784
bis(2,6-difluorophenyl)bis[(1,2,3,4,5-eta)-1-methyl-2,4-cyclopentadien-1-yl]titanium IRGACURE® 727

Phenyl Glyoxalates of Formula

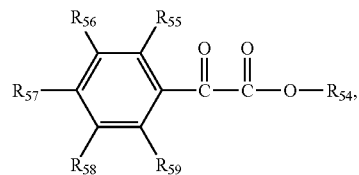
(VII)

wherein $R_{54}$ is hydrogen, $C_1$-$C_{12}$alkyl or a group

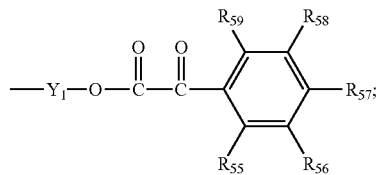

$R_{55}$, $R_{56}$, $R_{57}$, $R_{58}$ and $R_{59}$ are each independently of the others hydrogen; $C_1$-$C_{12}$alkyl which is unsubstituted or substituted by OH, $C_1$-$C_4$alkoxy, phenyl, naphthyl, halogen or by CN and which is uninterrupted or interrupted by one or more oxygen atoms, or $R_{55}$, $R_{56}$, $R_{57}$, $R_{58}$ and $R_{59}$ are $C_1$-$C_4$alkoxy, $C_1$-$C_4$alkylthio or $NR_{52}R_{53}$;

$Y_1$ is a bivalent aliphatic or aromatic radical, especially $C_1$-$C_{12}$alkylene.

An example is:
oxo-phenylacetic acid 2-[2-(2-oxo-2-phenyl-acetoxy)-ethoxy]-ethyl ester;

Surface-active Photoinitiators as Described in WO02/48204

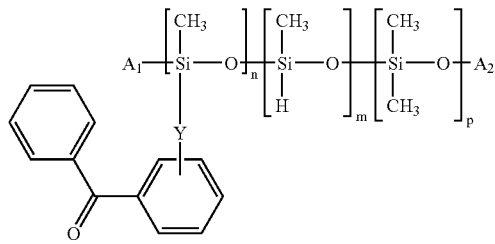

wherein
$A_1$ is methyl or —O—Si(CH$_3$)$_3$;
$A_2$ is methyl or —Si(CH$_3$)$_3$;
Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—;
a and b are 1-10;
n is 1-10;
m is 0-25;
p is 0-25.
An example is

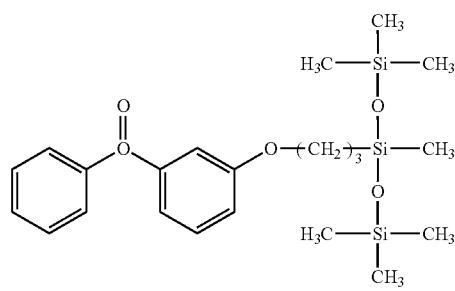

Siloxane-modified hydroxy ketones as described in EP 1 072 326

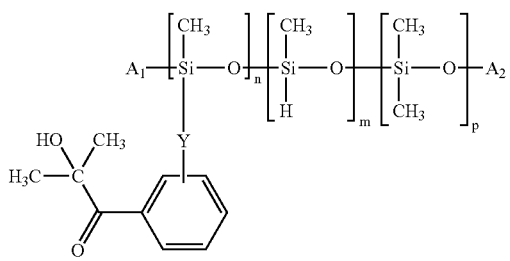

wherein
$A_1$ is methyl or —O—Si(CH$_3$)$_3$;
$A_2$ is methyl or —Si(CH$_3$)$_3$;
Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—;
a and b are 1-10;
n is 1-10;
m is 0-25;
p is 0-25.

An example is

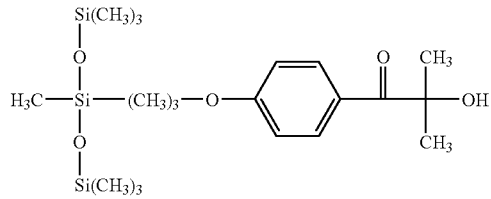

Surface-active benzil dialkyl ketals (BDK) or benzoins as described in WO 02/48203

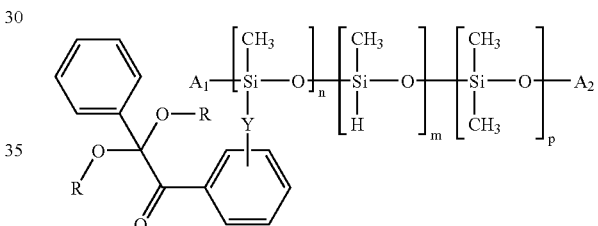

wherein
R is H or $C_1$-$C_4$alkyl;
$A_1$ is methyl or —O—Si(CH$_3$)$_3$;
$A_2$ is methyl or —Si(CH$_3$)$_3$;
Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—;
a and b are 1-10;
n is 1-10;
m is 0-25;
p is 0-25.
Examples are:

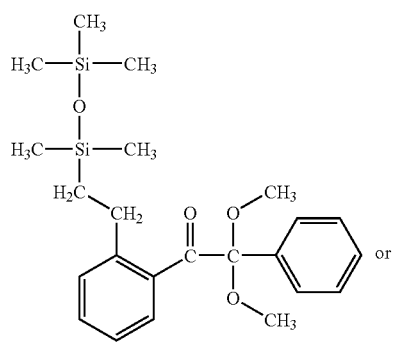

or

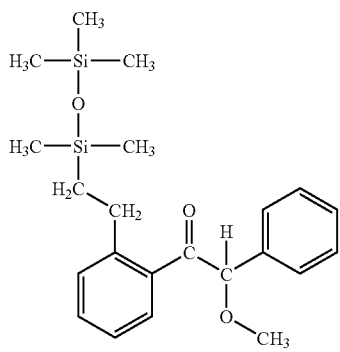

Monomeric and dimeric arylglyoxalic acid esters modified with siloxane as described in WO 02/14439

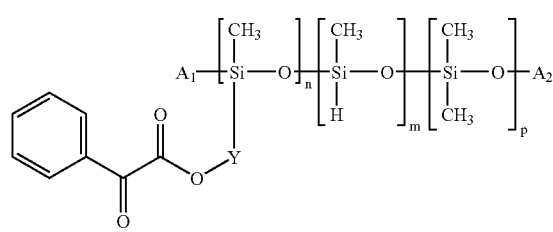

wherein
A$_1$ is methyl or —O—Si(CH$_3$)$_3$;
A$_2$ is methyl or —Si(CH$_3$)$_3$;
Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—;
a and b are 1-10;
n is 1-10;
m is 0-25;
p is 0-25.
An example is:

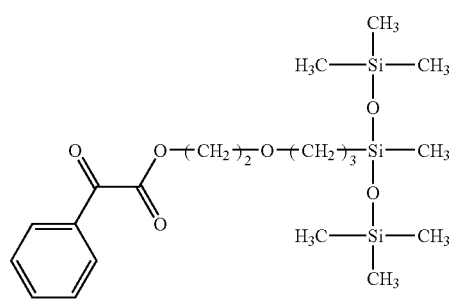

Monomeric and dimeric arylglyoxalic acid esters modified with siloxane as described in WO 02/14326

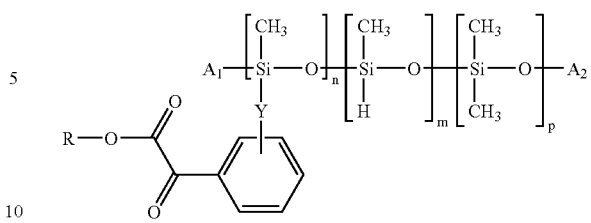

wherein
R is C$_1$-C$_4$alkyl;
A$_1$ is methyl or —O—Si(CH$_3$)$_3$;
A$_2$ is methyl or —Si(CH$_3$)$_3$;
Y is —(CH$_2$)$_a$—, —(CH$_2$)$_a$—O—, —(CH$_2$)$_b$—O—(CH$_2$)$_a$— or —(CH$_2$)$_b$—O—(CH$_2$)$_a$—O—;
a and b are 1-10;
n is 1-10;
m is 0-25;
p is 0-25.
An example is

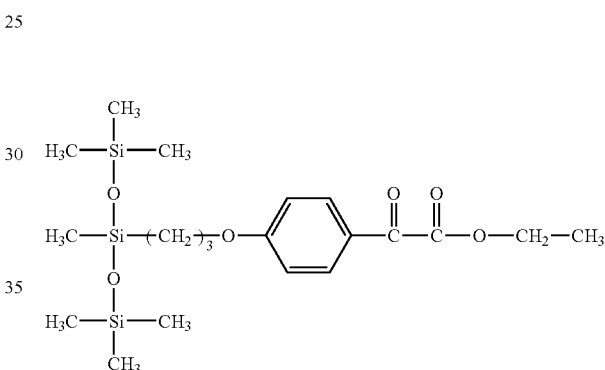

Long-chain alkyl-modified hydroxy ketones, as described in WO 02/48202, e.g. 1-(4-docosyloxy-phenyl)-2-hydroxy-2-methyl-1-propanone

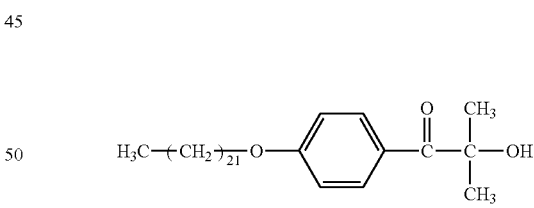

A further example of a benzophenone derivative is 1-[4-(4-benzoylphenylsulfanyl)phenyl]-2-methyl-2-(4-methylphenylsulfonyl)propan-1-one, obtainable as Esacure 1001 from Lamberti:

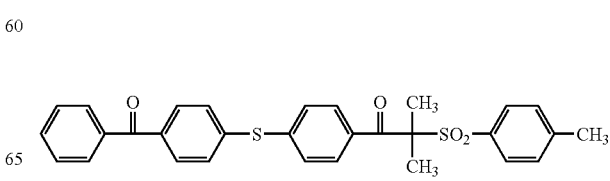

Other known photoinitiators (E) are, for example, mixtures with camphorquinone, acetophenones, 4-aroyl-1,3-dioxolanes, benzoin alkyl ethers and benzil ketals, such as benzil dimethyl ketal, peresters, for example benzophenonetetracarboxylic peresters as described, for example, in EP 126 541, halomethyltriazines, e.g. 2-[2-(4-methoxyphenyl)-vinyl]-4, 6-bistrichloromethyl[1,3,5]triazine, 2-(4-methoxyphenyl)-4, 6-bistrichloromethyl-[1,3,5]triazine, 2-(3,4-dimethoxyphenyl)-4,6-bistrichloromethyl[1,3,5]triazine, 2-methyl-4,6-bistrichloromethyl[1,3,5]triazine, hexaarylbisimidazole/coinitiator systems, e.g. ortho-chloro-hexaphenylbisimidazole together with 2-mercaptobenzothiazole, ferrocenium compounds or borate photoinitiators.

The photopolymerisable compositions contain the photoinitiator in an amount of, advantageously, from 0.05 to 15% by weight, preferably from 0.1 to 8% by weight, based on the composition. The indicated amount of photoinitiator is based on the total of all photoinitiators added when mixtures thereof are used, that is to say on photoinitiator (B) or on photoinitiators (B)+(D).

Use

The compositions according to the invention can be used for various purposes, for example in overprint coatings, as printing inks, as inkjet inks, as clearcoats, white coats or colour-pigmented coats, e.g. for wood or metal, as powder coatings, as paints, inter alia for paper, wood, metal or plastics, as daylight-curable paints for marking structures and roads, for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as etch resists or permanent resists, both liquid and dry films, as photostructurable dielectrics, and as solder masks for electronic circuits, as resists in the production of colour filters for any type of display screen or in the creation of structures during the manufacture of plasma displays and electroluminescent displays, in the production of optical switches, optical gratings (interference gratings), in the manufacture of three-dimensional articles by curing in the mass (UV curing in transparent moulds) or according to the stereolithography process, as described in, for example, U.S. Pat. No. 4,575,330, in the manufacture of composite materials (e.g. styrene polyesters which may include glass fibres and/or other fibres and other adjuvants) of gel coats and thick-layered compositions, in the coating or sealing of electronic components or as coatings for optical fibres. The compositions are also suitable for the production of optical lenses, e.g. contact lenses or Fresnel lenses, and also in the manufacture of medical apparatus, aids or implants. The compositions can also be used for the preparation of gels having thermotropic properties. Such gels are described in, for example, DE 197 00 064 and EP 678 534.

The photoinitiators according to the invention are also suitable for use in UV-curable adhesives. The adhesives may be both high-temperature adhesives and also those based on aqueous solutions or other solvents. Pressure-sensitive adhesives are especially suitable. Such adhesives comprise, for example, at least one rubber component, at least one resin as tackifier and at least one oil component, for example in the weight ratio 30:50:20. Natural or synthetic resins are suitable as tackifiers. Appropriate compounds, and also suitable oils and rubber components, will be known to the person skilled in the art.

The compounds according to the invention may also be used as initiators for emulsion, bead or suspension polymerisation processes or as initiators of polymerisation for the fixing of orientation states of liquid-crystalline monomers and oligomers, or as initiators for the fixing of dyes on organic materials.

A preferred field of use comprises overprint coatings and also pigmented thin coatings (layer thickness <20 μm), for example printing inks that are used in printing methods such as, for example, flexographic printing, offset printing, screen printing, intaglio printing, letterpress printing, tampon printing and inkjet printing.

Overprint coatings typically comprise ethylenically unsaturated compounds such as oligomeric and/or monomeric acrylates. Amine acrylates may also be included.

As mentioned hereinbefore, the overprint coatings and printing inks may also comprise further photoinitiators and coinitiators.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, fumarates, vinyl ethers, (meth)acrylates, (meth) acrylamides and mixtures thereof. A free-radical UV-curable powder coating may be formulated by mixing unsaturated polyester resins with solid acrylamides (e.g. methylacrylamido-glycolate methyl ester) and a free-radical photoinitiator according to the invention, for example as described in the lecture "Radiation Curing of Powder Coating", Conference Proceedings, Radtech Europe 1993 by M. Wittig and Th. Gohmann. Free-radical UV-curable power coatings may also be formulated by mixing unsaturated polyester resins with solid acrylates, methacrylates or vinyl ethers and a photoinitiator (or photoinitiator mixture) according to the invention. The powder coatings may also comprise binders, as described in, for example, DE 4228 514 and EP 636 669. The powder coating formulations described in EP 636 669 comprise, for example, a) an unsaturated resin from the group of (semi-) crystalline or amorphous unsaturated polyesters, unsaturated polyacrylates or mixtures thereof with unsaturated polyesters, with special preference being given to those derived from maleic acid or fumaric acid; b) an oligomeric or polymeric crosslinking agent containing vinyl ether-, vinyl ester- or (meth)acrylate-functional groups, with special preference being given to vinyl ether oligomers, for example divinyl ether-functionalised urethanes; c) the photoinitiator. The UV-curable powder coatings may also comprise white or coloured pigments. Accordingly, for example, there may preferably be used rutile titanium dioxide in concentrations of up to 50% by weight in order to obtain a cured powder coating with good hiding power. The process normally comprises electrostatic or tribostatic spraying of the powder onto the substrate, e.g. metal or wood, melting of the powder as a result of heating and, after a smooth film has been formed, radiation-curing of the coating using ultraviolet and/or visible light, for example using medium-pressure mercury lamps, metal halide lamps or xenon lamps. A particular advantage of radiation-curable powder coatings compared to corresponding thermally curable coatings is that the flow time after melting of the powder particles can be extended as desired in order to ensure the formation of a smooth high-gloss coating. In contrast to thermally curable systems, radiation-curable powder coatings can be formulated so that they melt at relatively low temperatures, without the undesirable effect of a reduction in shelf-life. For that reason they are also suitable as coatings for heat-sensitive substrates, for example wood or plastics. However, if the powder coatings are to be applied to non-heat-sensitive substrates, for example metals (vehicle coatings), it is also possible to make available "dual cure" powder coating formulations using the photoinitiators according to the invention. Such formulations will be known to the person skilled in the art; they are cured both thermally and also by means of UV and can be found in, for example, U.S. Pat. No. 5,922,473.

The compounds according to the invention may also be used in the form of an aqueous, for example 0.5-5%, preferably 0.5-2%, dispersion in polymer dispersions, for example in aqueous polyurethane dispersions, so-called PUDs.

The photocurable compositions according to the invention are suitable, for example, as coating substances for substrates of all kinds, e.g. wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which a protective layer or, by means of image-wise exposure, an image is to be applied.

The substrates can be coated by applying a liquid composition, a solution or a suspension or a powder to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents are, for example, ketones, ethers and esters, e.g. methyl ethyl ketone, isobutyl methyl ketone, cyclopentanone, cyclohexanone, N-methylpyrrolidone, dioxane, tetrahydrofuran, 2-methoxy-ethanol, 2-ethoxyethanol, 1-methoxy-2-propanol, 1,2-dimethoxy-ethane, ethyl acetate, n-butyl acetate and ethyl 3-ethoxypropionate.

The formulation is applied uniformly to a substrate by means of known coating methods, for example by spin-coating, immersion, roller application, knife coating, curtain pouring, brush application or spraying, especially by electro-static spraying and reverse-roll coating, and also by electrophoretic deposition. It is also possible to apply the photosensitive layer to a temporary flexible support and then coat the final substrate by transferring the layer via lamination. Examples of types of application are to be found, for example, in Ullmann's Encyclopedia of Industrial Chemistry, 5th Ed., Vol. A18, pp. 491-500.

The amount applied (layer thickness) and the nature of the substrate (layer support) are dependent on the desired field of use.

A further field of use comprises compositions that are suitable for the coating of glass fibres, both for the inner and also for the middle and outer layers. The coated glass fibres may also be gathered into bundles giving a further coating. Such coating layers comprise UV-curable oligomers, UV-curable monomers and also at least one photoinitiator and additives.

Any UV-curable oligomer is suitable for the coating of glass fibres. Preference is given to oligomers having an average molecular weight of at least 500, for example 500-10 000, 700-10 000, 1000-8000 or 1000-7000. Urethane oligomers or urethane methacrylates and also mixtures with further oligomers as described in, for example, U.S. Pat. No. 6,136,880 are especially suitable.

The UV-curable monomer may be used to influence the viscosity of the coating composition and to establish a desired viscosity, for example in the range from 1000 to 10 000 mPas. Accordingly, there are used, for example, suitable low-viscosity functionalised monomers (monomers containing acrylate radicals, vinyl ether radicals, polyether radicals or radicals of higher alkyl ethers) in an amount of from 10 to 90% by weight. Examples of suitable monomers are described in U.S. Pat. No. 6,136,880. U.S. Pat. No. 6,136,880 is incorporated in the invention by way of reference.

In order to improve the adhesion properties, suitable compositions may furthermore comprise polysiloxanes as described in U.S. Pat. No. 5,595,820.

The composition may comprise further additives as described hereinbefore (Additives section). There may be mentioned, for example, antioxidants, light stabilisers, UV absorbers such as, for example, ®IRGANOX 1035, 1010, 1076, 1222, ®TINUVIN P, 234, 320, 326, 327, 328, 329, 213, 292, 144, 622LD (commercially available from Ciba Specialty Chemicals), ®ANTIGENE P, 3C, FR, GA-80, ®SUMISORB TM-061 (commercially available from Sumitomo Chemical Industries Co.), ®SEESORB 102, 103, 501, 202, 712, 704 (commercially available from Sypro Chemical Co., Ltd.), ®SANSOL LS770 (Sankyo Co. Ltd.). Especially advantageous are combinations of sterically hindered piperidine derivatives (HALS) and sterically hindered phenols, for example additives of IRGANOX 1035 and TINUVIN 292, for example in a quantitative ratio of 1:1 (see U.S. Pat. No. 4,923,915).

The composition may also comprise silane coupling reagents as additives, e.g. γ-amino-propyltriethoxysilane, γ-mercaptopropyltrimethoxysilane, γ-methacryloxypropyl-trimethoxy-silane, SH6062, SH6030 (commercially available from Toray-Dow Corning Silicone Co., Ltd.), KBE 903, KBE 603, KBE 403 (commercially available from Shin-Etsu Chemical Co.).

In order to prevent yellowing of the coating, fluorescent whitening agents may be added, e.g. ®UVITEX OB, commercially available from Ciba Specialty Chemicals.

As described above, further photoinitiators may be added to the photoinitiators according to the invention also in the case of glass fibre coatings.

During coating, the layer applied first may be cured before the next layer is applied, or the layers are applied first and then cured together.

In order to be able to differentiate between individual glass fibres in a strand, the glass fibres may be coated with a colouring layer comprising pigments or dyes ("ink coating"). Examples of suitable pigments are those given above.

Further fields of use of photocuring are metal coating, for example the application of a finish to sheet metals and tubes, cans or bottle closures, and also photocuring on plastics coatings, for example PVC-based floor or wall coverings.

Examples of the photocuring of paper coatings are the application of a colourless finish to labels, packaging materials or book covers.

The photosensitivity of the compositions according to the invention usually extends from approximately 200 nm into the IR range. Suitable radiation is present, for example, in sunlight or light from artificial light sources. Accordingly a large number of the most varied kinds of light source may be used. Both point sources and planiform radiators (lamp arrays) are suitable. Examples are: carbon arc lamps, xenon arc lamps, medium-pressure, high-pressure and low-pressure mercury radiators doped, where appropriate, with metal halides (metal halide lamps), microwave-excited metal vapour lamps, excimer lamps, superactinic fluorescent tubes, fluorescent lamps, argon incandescent lamps, flash lamps, e.g. high-energy flash lamps, photographic floodlight lamps, light-emitting diodes (LED), electron beams and X-rays. The distance between the lamp and the substrate to be exposed may vary according to the intended use and the type and strength of the lamp and may be, for example, from 2 cm to 150 cm. Especially suitable are laser light sources, for example excimer lasers, such as Krypton-F lasers for exposure at 248 nm. Lasers in the visible and infrared or NIR range may also be used.

As already mentioned, curing in the process according to the invention can be carried out solely by irradiation with electromagnetic radiation. Depending on the composition of the formulation to be cured, however, thermal curing before, during or after the irradiation is advantageous.

Thermal curing is carried out by methods known to the person skilled in the art. In general, the curing is carried out in an oven, e.g. a circulating air oven, on a heating plate or by irradiation with IR lamps. Unassisted curing at room temperature is also possible, depending on the binder system used. The curing temperatures are generally between room temperature and 150° C., for example from 25 to 150° C. or from 50 to 150° C. In the case of powder coatings or coil coatings, the curing temperatures may be even higher, e.g. up to 350° C.

The invention relates also to a process for the production of a scratch-resistant durable surface, wherein
(1) a composition as described hereinbefore is prepared;
(2) that formulation is applied to a support; and
(3) curing of the formulation is carried out either solely by means of irradiation with electro-magnetic radiation having a wavelength of from 200 nm into the IR range, or by irradiation with electromagnetic radiation and prior, simultaneous and/or subsequent application of heat.

The invention relates also to the use of the above-described composition and to a process for the production of pigmented and non-pigmented surface coatings, overprint coatings, powder coatings, printing inks, inkjet inks, gel coats, composite materials or glass fibre coatings.

The invention relates also to a coated substrate which is coated on at least one surface with a composition as described above.

The following Examples illustrate the invention in greater detail:

EXAMPLE 1

Preparation of bis[4-(2-methyl-propionyl)-phenyl]-methane

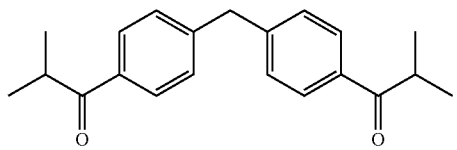

EXAMPLE 1a

Friedel-Crafts Reaction, Addition of AlCl₃ in Solid Form, Steam Distillation of 1,2-dichlorobenzene and then Crystallisation of the p,p-isomer from Mixed Hexanes 109.4 g (0.65 mol) of diphenylmethane, 159.3 g (1.495 mol) of isobutyric acid chloride and 196 g of 1,2-dichlorobenzene are combined and cooled in an ice bath to 5-0° C. Then, over the course of about four hours, at an internal temperature of 5-0° C., 208.0 g (1.56 mol) of aluminium chloride are added in small portions. HCl gas is evolved. Stirring is then carried out at an internal temperature of 0-5° C. for about 16 hours. At the end all the aluminium chloride has dissolved. The dark-red reaction mixture is then poured into ice and water and stirred to complete the reaction. The two phases are separated in a separating funnel. The organic phase is washed with water and then concentrated for a short time in a vacuum rotary evaporator at about 60° C. and about 25 mbar, resulting in 398 g of a yellow liquid, an isomeric mixture having bis[4-(2-methyl-propionyl)-phenyl]-methane as the main component. In the GC and $^1$H NMR spectrum there are found, excluding the solvent 1,2-dichlorobenzene, 87.3% p,p-isomer, 11.8% m,p-isomer, 0.7% m,m-isomer and 0.2% mono p-compound. The product is freed of the solvent 1,2-dichlorobenzene by steam distillation. The overhead temperature during the distillation is about 95° C. and the distillation takes about 3 hours. About 150 ml of 1,2-dichlorobenzene are recovered. The residue, a yellowish emulsion, is diluted with 70 g of mixed hexanes at about 50° C. and separated from the water whilst still warm. The organic phase is crystallised at room temperature and then at 5-0° C. A further 120 g of mixed hexanes are added in portions. The crystals are filtered off, washed with mixed hexanes and dried in vacuo at 30° C. 145.3 g of faintly yellowish crystals are obtained. In the GC there are now found 94% p,p-isomer and 6% m,p-isomer. The mother liquor is concentrated. The yellow oil obtained (47 g) contains, according to GC, 59% p,p-isomer, 30% m,p-isomer, 2% m,m-isomer and unknowns.

The 145.3 g of crystals are dissolved in 150 g of mixed hexanes in the warm state and recrystallised. The crystals are filtered off at 5° C., washed with mixed hexanes and dried. 135.2 g of faintly yellowish crystals are obtained. In the GC there are now found 96.6% p,p-isomer and 3.4% m,p-isomer. The mother liquor is concentrated. The yellow oil obtained (8 g) contains, according to GC, 50% p,p-isomer, 34% m,p-isomer, 2% m,m-isomer and unknowns.

The 135.2 g of crystals are dissolved in 135 g of mixed hexanes in the warm state and recrystallised. The crystals are filtered off at 5° C., washed with mixed hexanes and dried. 132.5 g of faintly yellowish crystals are obtained. In the GC there are now found 98.7% p,p-isomer and 1.3% m,p-isomer. The mother liquor is concentrated. The yellow oil obtained (5.4 g) contains, according to GC, 66% p,p-isomer and 27% m,p-isomer.

The 132.5 g of crystals are dissolved in 135 g of mixed hexanes in the warm state and recrystallised. The crystals are filtered off at 5° C., washed with mixed hexanes and dried. 122.7 g of faintly yellowish crystals are obtained, which melt at 43.1-44.1 ° C. In the GC there are now found 99.6% p,p-isomer and 0.4% m,p-isomer.

EXAMPLE 1b

Friedel-Crafts Reaction, AlCl₃ Added Dropwise in Dissolved Form 130.0 g (1.22 mol) of isobutyric acid chloride and 100 g of 1,2-dichlorobenzene are introduced into a 500 ml reaction flask and cooled to 5-0° C. using an ice bath. Then, over about 20 minutes, at an internal temperature of 5-0° C., 104.0 g (0.78 mol) of aluminium chloride are added in small portions. The dissolution process is slightly exothermic. The yellowish solution is kept at an internal temperature of 5-0° C.

109.4 g (0.65 mol) of diphenylmethane, 29.3 g (0.275 mol) of isobutyric acid chloride and 100 g of 1,2-dichlorobenzene are introduced into a 750 ml reaction flask and cooled to 5-0° C. using an ice bath. The aluminium chloride solution is then added dropwise over two hours at an internal temperature of 0-5° C. The solution becomes dark-yellow and HCl gas is evolved. In the GC there are now found about 90% mono compound. Then, over 90 minutes and at an internal temperature of 5-0° C., a further 104.0 g (0.78 mol) of aluminium chloride are added in small portions. HCl gas is further evolved. The suspension is subsequently stirred for about twenty hours at an internal temperature of 0-5° C. At the end, all the aluminium chloride has dissolved. The red reaction mixture is then poured into ice and water and stirred to complete the reaction. The two phases are separated in a separating funnel. The organic phase is washed with water and then concentrated for a short time in a vacuum rotary evaporator at about 60° C. and about 25 mbar, resulting in 456 g of a yellowish liquid. The product, an isomeric mixture having bis[4-(2-methyl-propionyl)-phenyl]-methane as the main component, is used in the next reaction without further purification. In the GC there are found, excluding the solvent 1,2-dichlorobenzene, 86.4% p,p-isomer, 11.9% m,p-isomer, 0.7% m,m-isomer and 1.0% mono p-compound.

EXAMPLE 1c

Friedel-Crafts-reaction 218.8 g (1.30 mol) diphenylmethane, 318.6 g (2.99 mol) of isobutyric acid chloride and 490 g 1,2-dichlorbenzene (375 ml) are combined and cooled in an ice bath to 5-0° C. Then, over the course of about four hours, at an internal temperature of 5-0° C., 416.0 g (3.12 mol) of aluminium chloride are added in small portions. HCl gas is evolved. Stirring is then carried out at an internal temperature of 0-5° C. for 16-20 hours. At the end all the aluminium chloride has dissolved. The reaction was monitored by means of GC. When the amount of mono product is less than 1.5%, the dark-red reaction mixture is then poured into ice and water and stirred for 30 min. to complete the reaction. The two phases are separated in a separating funnel. The aqueous phase is extracted with 50 g of dichlorobenzene. The organic phase is washed with water and then concentrated for a short time in a vacuum rotary evaporator at about 60° C. and about 25 mbar, resulting in 962 g of a yellow liquid, an isomeric mixture having bis[4-(2-methyl-propionyl)-phenyl]-methane as the main component. In the GC and $^1$H NMR spectrum there are found, excluding the solvent 1,2-dichlorobenzene, 87.3% p,p-isomer, 11.8% m,p-isomer, 0.7% m,m-isomer and 0.2% mono p-compound. The crude product is further reacted without purification in the enol chlorination process.

EXAMPLE 2

Enol Chlorination and Bromination

Preparation of bis[4-(2-chloro-2-methyl-propionyl)-phenyl]-methane and then bis[4-(2-chloro-2-methyl-propionyl)-phenyl]-bromomethane

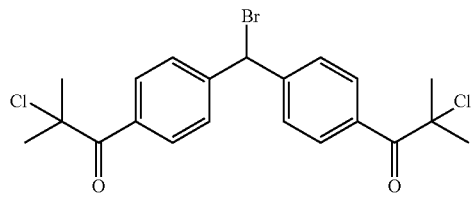

EXAMPLE 2a

Enol Chlorination and Bromination in 1,2-dichlorobenzene, 456 g (0.65 mol) of solution of the isomeric mixture of bis[4-(2-methyl-propionyl)-phenyl]-methane with [3-(2-methyl-propionyl)-phenyl]-[4-(2-methyl-propionyl)-phenyl]-methane in 1,2-dichlorobenzene from the Friedel-Crafts reaction are heated to 55-60° C. in a 750 ml reaction flask using an oil bath. Then, at 55-60° C., whilst stirring well, 92.2 g (1.30 mol) of chlorine gas are introduced through a glass frit, relatively quickly at the start and just slowly at the end. HCl gas is evolved. The duration of introduction is about 5 hours. 497 g of a yellowish liquid are obtained. The product, an isomeric mixture having bis[4-(2-chloro-2-methyl-propionyl)-phenyl]-methane as the main component, is used in the next reaction without further purification. In the $^1$H NMR spectrum there are found, excluding the solvent 1,2-dichlorobenzene, about 3% ketone and about 97% α-chloroketone, which consists of about 86% p,p-isomer and about 12% m,p-isomer.

Following chlorination, the 497 g (0.65 mol) of solution of the isomeric mixture of bis[4-(2-chloro-2-methyl-propionyl)-phenyl]-methane with [3-(2-chloro-2-methyl-propionyl)-phenyl]-[4-(2-chloro-2-methyl-propionyl)-phenyl]-methane in 1,2-dichlorobenzene are cooled to about 40° C. The 750 ml reaction flask is wrapped in aluminium foil and irradiated with a 60 Watt daylight lamp. 103.9 g (0.65 mol) of bromine are then slowly added dropwise. HBr gas is evolved and the temperature slowly rises to 50-55° C. After about 80% of the bromine has been added, the addition is stopped and a second 60 Watt daylight lamp is additionally switched on. The reaction proceeds slowly in 1,2-dichlorobenzene. On the next day, the addition of bromine is resumed and completed. Later, a further 13.5 g (0.0845 mol) of bromine are added dropwise. When only a very small amount of starting material is still to be seen in the $^1$H NMR spectrum, the solution is concentrated using a vacuum rotary evaporator and subjected to steam distillation. 336 g of dark oil are obtained.

The oil is diluted with 150 ml of ethyl acetate and filtered through a 3 cm thick silica gel bed, rinsing with 200 ml of ethyl acetate. Beige crystals crystallise out from the filtrate overnight. The crystals are filtered off and dried. These crystals (84.3 g) are recrystallised from 300 g of cyclohexane, filtered and dried. 73.8 g of white crystals are obtained which melt at 93.3-94.8° C. In the $^1$H NMR spectrum there is found the isomer-free dichlorobromo compound 1-(4{bromo-[4-(2-chloro-2-methyl-propionyl)-phenyl]-methyl}-phenyl)-2-chloro-2-methyl-propan-1-one.

The mother liquor is concentrated using a vacuum rotary evaporator. The dark oil (209 g) solidifies overnight and is stirred with 100 g of cyclohexane. The crystals are filtered off, washed and dried. There are obtained 29.4 g of beige crystals which are again identified as the isomer-free dichlorobromo compound in the $^1$H NMR spectrum.

Further crystals crystallise out from the mother liquor in a refrigerator.

When a sample of the isomer-free dichlorobromo compound is recrystallised from methanol, the dichloromethoxy compound 1-(4-{methoxy-[4-(2-chloro-2-methyl-propionyl)-phenyl]-methyl}-phenyl)-2-chloro-2-methyl-propan-1-one, in the form of an oil, is obtained according to the $^1$H NMR spectrum.

EXAMPLE 2b

Enol Chlorination and Bromination in CCl₄

400.9 g (1.30 mol tq) of the isomeric mixture of bis[4-(2-methyl-propionyl)-phenyl]-methane with [3-(2-methyl-propionyl)-phenyl]-[4-(2-methyl-propionyl)-phenyl]-methane from the Friedel-Crafts reaction are dissolved in 450 g of carbon tetrachloride in a 1.5 litre reaction flask and heated to 55-60° C. using an oil bath. Then, at 55-60° C., whilst stirring well, 184.4 g (2.60 mol) of chlorine gas are introduced through a glass frit, relatively quickly at the start and more slowly at the end. HCl gas is evolved. The duration of introduction is about six hours. The product, an isomeric mixture having bis[4-(2-chloro-2-methyl-propionyl)-phenyl]-methane as the main component, is cooled and then brominated without being isolated in the interim. In the $^1$H NMR spectrum there are still found about 2% monochloro compound.

The solution is diluted with a further 250 g of carbon tetrachloride at about 26° C. The reaction flask is wrapped in aluminium foil and irradiated with two 60 Waft daylight lamps. 207.8 g (1.30 mol) of bromine are then added dropwise over about three hours. The temperature rises to about 62° C. The colour of the solution is discharged continuously and HBr gas is evolved. Later on, the colour of the solution is discharged more slowly and it remains red. In the $^1$H NMR spectrum there are still found, in addition to the main component bis[4-(2-chloro-2-methyl-propionyl)-phenyl]-bromomethane, about 15% of an intermediate product. The solution is diluted with a further 300 g of carbon tetrachloride. Whilst irradiating, a further 31.2 g (0.195 mol) of bromine are added dropwise at 60° C. The intermediate product is reduced to about 8%. The reddish solution is concentrated in vacuo. 643.3 g tq of dark oil are obtained, which starts to crystallise.

492.6 g of oil are recrystallised from 300 g of cyclohexane, followed by filtration and washing. 134 g of white crystals are obtained. From the mother liquor there are obtained, by means of concentration, a further 356 g of yellow crystals, which are recrystallised from 300 g of cyclohexane, filtered and washed with 100 g of cyclohexane. 200 g of yellowish crystals are thereby obtained. From the next mother liquor there are obtained, by means of partial concentration, a further 16.1 g of white crystals, and 112.4 g of dark-yellow oil remain. Unfortunately, all those crystal fractions of bis[4-(2-chloro-2-methyl-propionyl)-phenyl]-bromomethane are, according to the $^1$H NMR spectrum, mixed with the subsidiary product bis[4-(2-chloro-2-methyl-propionyl)-phenyl]-dibromomethane (the first fractions to the greatest extent). The product has been over-brominated in this experiment. The subsidiary product is expected to give rise to bis[4-(2-chloro-2-methyl-propionyl)-phenyl]-methanone during hydrolysis.

EXAMPLE 2c

Enol Chlorination 962 g (1.30 mol) of a solution of bis-(4-isobutyrylphenyl)-methane in 1,2-dichlorbenzene is heated to 55-60° C. Then, at 55-60° C., whilst stirring well, 184.4 g (2.60 mol) of chlorine gas are introduced through a glass frit, relatively quickly at the start and just slowly at the end. HCl gas is evolved. The duration of introduction is about 8 hours. 1053 g of a yellowish liquid are obtained. The product is an isomeric mixture having bis[4-(2-chloro-2-methyl-propionyl)-phenyl]-methane as the main component. In the $^1$H NMR spectrum there are found, excluding the solvent 1,2-dichlorobenzene, about 5% ketone and small amount of the trichloro compound. The solvent is distilled off. The distillation takes about 7 hours. 526 g of the solvent 1,2-dichlorbenzene are obtained back.

Then 150 g of chlorobenzene are added. The reaction mixture is cooled and the acid water is separated. The organic phase is concentrated. Yield: 578.8 g of a yellow liquid, an isomeric mixture of the main component bis-[4-(2-chlor-2-methyl-propionyl)-phenyl]-methane. There is more educt to be seen in the $^1$H-NMR-Spectrum. The product is further reacted in the following bromination step.

Bromination 289.4 g (0.65 mol) of bis-[4-(2-chlor-2-methyl-propionyl)-phenyl]-methane are dissolved in 500 g of carbon tetrachloride. The reaction flask is wrapped in aluminium foil and irradiated with a 100 Watt daylight lamps. 103.9 g (0.65 mol) of bromine are then added dropwise. The temperature rises to 60-70° C. The colour of the solution is discharged continuously and HBr gas is evolved. Later on, the colour of the solution is discharged more slowly and it remains red. After two hours half of the bromine is added, after four hours 75% of the bromine is added and after 5.5 hours 90% of the bromine is added. The remaining bromine is added diluted with 20 ml of carbon tetrachloride. In the $^1$H NMR spectrum there are still found, in addition to the main component bis [4-(2-chloro-2-methyl-propionyl)-phenyl]-brom-methane, about 6% of the dibromo compound bis-[4-(2-chlor-2-methyl-propionyl)-phenyl]-dibrom-methane and ca. 13% educt bis-[4-(2-chlor-2-methyl-propionyl)-phenyl]-methane.

After 7 hours, there are found in the $^1$H NMR spectrum, in addition to the main component ca 8% of the dibromo compound and 8% of the educt. The bromine addition is stopped.

The reaction mixture is irradiated for another 45 minutes and cooled. The solution obtained is concentrated. The a small amount of toluene is added and concentrated again. Yield: 328.5 g of a yellow oil, an isomeric mixture having as main component bis-[4-(2-chlor-2-methyl-propionyl)-phenyl]-brom-methane, which starts to crystallise. The crystals are dissoved in 540 g of cyclohexane, recrystallised, filtered off at room temperature, washed with 100 g of cyclohexane. The white crystals are dried (60° C., 150 mbar). Yield: 189 g of white crystals, mp. 88-90° C. In the $^1$H-NMR-Spectrum there is found only the main compound bis-[4-(2-chlor-2-methyl-propionyl)-phenyl]-brom-methane.

The mother liquor is concentrated. 112.3 g of an oil is obtained, which slowly starts to crystallise.

The crystals are recrystallised in 200 g of cyclohexane, washed, dried. Yield: 25 g of white crystals. In the $^1$H-NMR-Spectrum there is found 67% of the main component bis-[4-(2-chlor-2-methyl-propionyl)-phenyl]-brom-methane and 33% of bis-[4-(2-chlor-2-methyl-propionyl)-phenyl]-dibrom-methane.

EXAMPLE 3

Preparation of bis[4-(2-bromo-2-methyl-propionyl)-phenyl]-methane and then bis[4-(2-bromo-2-methyl-propionyl)-phenyl]-bromomethane

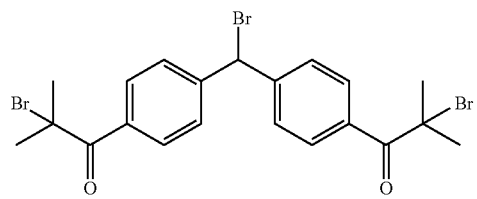

Enol bromination and bromination in CCl$_4$ 61.6 g (0.20 mol) of recrystallised bis[4-(2-methyl-propionyl)-phenyl]-methane from the Friedel-Crafts reaction are dissolved in 210 ml of carbon tetrachloride in a 750 ml reaction flask. Then, at room temperature, 63.4 g (0.40 mol) of bromine, diluted with 45 ml of carbon tetrachloride, are slowly added dropwise over one hour. The colour of the solution is discharged continuously and HBr gas is evolved. At the end, the solution remains reddish. In the $^1$H NMR spectrum there is now found, exclusively, bis[4-(2-bromo-2-methyl-propionyl)-phenyl]-methane. The 750 ml reaction flask is wrapped in aluminium foil and irradiated with a 60 Watt daylight lamp. Then 31.7 g (0.20 mol) of bromine, diluted with 25 ml of carbon tetrachloride, are slowly added dropwise over three hours. The colour of the solution is discharged continuously in the light, and HBr gas is evolved. The lamp slowly heats the solution and the temperature increases to 60° C. In the $^1$H NMR spectrum there are found, at the end, about 92% dibromo compound and about 8% tribromo compound. Then, an additional 1.6 g (0.01 mol) of bromine, diluted with 5 ml of carbon tetrachloride, are slowly added dropwise. After two hours, the colour of the solution has been discharged under irradiation, and in the $^1$H NMR spectrum there is now found, practically exclusively, 2-bromo-1-(4-{bromo-[4-(2-bromo-2-methyl-propionyl)-phenyl]-methyl}-phenyl)-2-methyl-propan-1-one. The yellowish solution is concentrated using a vacuum rotary evaporator. 113.9 g of a yellowish viscous oil are obtained, which later crystallises out slowly. The crystals are recrystallised from diethyl ether and dried, resulting in 64.6 g of white crystals which melt at 96.5-97.5° C. In the $^1$H NMR spectrum there is found, exclusively, 2-bromo-1-(4-{bromo-[4-(2-bromo-2-methyl-propionyl)-phenyl]-methyl}-phenyl)-2-methyl-propan-1-one. From the mother liquor there are obtained a further 42.7 g of almost white crystals.

Elemental analysis of the tribromo compound: (545,11)

|  | % C |  | % H |  | % Br |
|---|---|---|---|---|---|
| calculated | 46.27 | calculated | 3.88 | calculated | 43.97 |
| found | 46.47 | found | 3.93 | found | 43.8 |

EXAMPLE 4

Synthesis of 1-(4-{Bromo-[4-(2-hydroxy-2-methyl-propionyl)-phenyl]-methyl}-phenyl)-2-hydroxy-2-methyl-propan-1-one

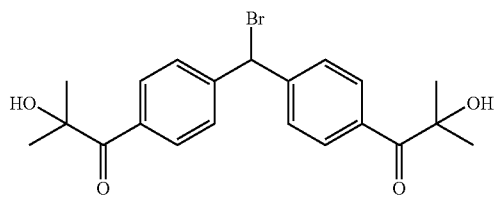

11.2 g (0.063 mol) N-bromosuccinimide, and 0.12 g AIBN (2,2-azobis(2-methylpropionitrile)) were suspended in 50 ml carbon tetrachloride and heated to 40° C. under argon. Then a solution of 20.45 g (0.06 mol) of 2-Hydroxy-1{-4-[4-(2-hydroxy-2-methyl-propionyl)-benzyl]-phenyl}2-methyl-propan-1-one (known from PCT Int. Appl. WO 2003040076) in 50 ml carbon tetrachloride was added dropwise over 15 min. After stirring at 75° C. for 3 h, the reaction mixture was cooled to 25° C., filtered, and washed neutral with water, dried over magnesium sulfate and concentrated by evaporation. The raw product (28.4 g) was a brownish resin that was pure enough for further derivatization of the benzylic bromide. The structure was confirmed by $^1$H-NMR (CDCl$_3$): δ [ppm]: 8.04 (d, 4H), 7.53 (d, 4H), 6.28 (s, 1H, benzylic), 3.95, (s, 2H, OH), 1.61 (s, 12H),

EXAMPLE 5

Preparation of bis[4-(2-hydroxy-2-methyl-propionyl)-phenyl]-methoxymethane

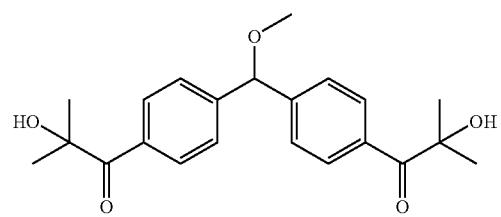

Hydrolysis of the tribromo compound in water and methanol 33.5 g (0.251 mol) of 30% concentrated NaOH and 34 ml of deionised water and 34 g of methanol are combined in a 350 ml reaction flask. Then, whilst stirring well, 38.0 g (0.0697 mol) of 2-bromo-1-(4-{bromo-[4-(2-bromo-2-methyl-propionyl)-phenyl]-methyl}-phenyl)-2-methyl-propan-1-one, dissolved in 50 g of toluene and 17 g of methanol, are added dropwise at 50° C. over about one hour. The internal temperature slowly increases to 55-60° C. The alkaline emulsion (about pH 12) is subsequently stirred for about one hour at 55-60° C. The conversion is checked using a $^1$H NMR sample. The mixture is then cooled to 20° C. and adjusted to about pH 1-2 using about 11.4 g of 16% hydrochloric acid dropwise. The mixture is heated to 55° C. and subsequently stirred for about 50 minutes. After hydrolysis is complete, the reaction mixture is neutralised using a small amount of dilute sodium hydroxide solution. The two phases are separated in a separating funnel at about 30° C. The organic phase is concentrated in a vacuum rotary evaporator. 23.6 g of reddish-yellow viscous oil are obtained. In the $^1$H NMR spectrum there are found the methyl ether 2-hydroxy-1-(4-{[4-(2-hydroxy-2-methyl-propionyl)-phenyl]-methoxy-methyl}-phenyl)-2-methyl-propan-1-one and the tris-hydroxy compound 2-hydroxy-1-(4-{hydroxy-[4-(2-hydroxy-2-methyl-propionyl)-phenyl]-methyl}-phenyl)2-methyl-propan-1-one in a ratio of 4:1. 17.6 g of that oil are resolved using a silica gel column. A 1:1 mixture of ethyl acetate and mixed hexanes is used as mobile phase, resulting in 11.3 g of yellowish viscous oil of the methyl ether 2-hydroxy-1-(4-{[4-(2-hydroxy-2-methyl-propionyl)-phenyl]-methoxy-methyl}-phenyl)-2-methyl-propan-1-one and 2.5 g of yellowish viscous oil of the tris-hydroxy compound 2-hydroxy-1-(4-{hydroxy-[4-(2-hydroxy-2-methyl-propionyl)-phenyl]-methyl}-phenyl)-2-methyl-propan-1-one.

Elemental analysis of the methyl ether: (370.45)

|  | % C |  | % H |
|---|---|---|---|
| calculated: | 71.33 | calculated: | 7.07 |
| found: | 71.71 | found: | 7.20 |

EXAMPLE 6

Preparation of bis[4-(2-hydroxy-2-methyl-propionyl)-phenyl]-methanol

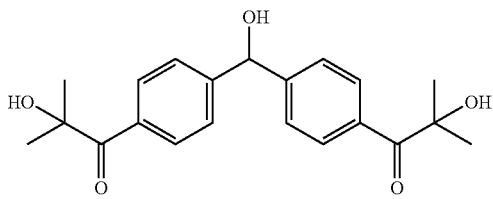

Hydrolysis of the tribromo Compound in Water and dioxane 27.3 g (0.05 mol) of recrystallised 2-bromo-1-(4-{bromo-[4-(2-bromo-2-methyl-propionyl)-phenyl]-methyl}-phenyl)-2-methyl-propan-1-one are dissolved in 100 g of dioxane in a 350 ml reaction flask. A solution of 0.5 g (1.5 mmol) of tetrabutylammonium bromide in 10 g of water is then added. 48 g (0.18 mol) of 15% NaOH are then added dropwise over 30 minutes. The temperature increases from 26 to 39° C. The pH is between 10 and 11. After checking the reaction by means of the $^1$H NMR spectrum, the mixture is heated to 87° C. After 2 hours, the conversion is complete according to the $^1$H NMR spectrum. The reaction mixture is cooled and neutralised using 6.0 g of 16% HCl solution. The aqueous phase is separated off and the organic phase is concentrated. The crude product is dissolved in ethyl acetate and freed from a small amount of salt. The crude product, 21 g of dark oil, is purified over a silica gel column. A 1:1 mixture of ethyl acetate and mixed hexanes is used as mobile phase. The main fraction is concentrated and recrystallised from a small amount of toluene. 9.4 g of white crystals are obtained, which melt at 130.1-131.9° C. In the $^1$H NMR spectrum there is found, exclusively, 2-hydroxy-1-(4-{hydroxy-[4-(2-hydroxy-2-methyl-propionyl)-phenyl]-methyl}-phenyl)-2-methyl-propan-1-one.

EXAMPLE 7

Hydrolysis of the Tribromo Compound in Water and Dioxane 43.6 g (0.08 mol) of recrystallised 2-bromo-1-(4-{bromo-[4-(2-bromo-2-methyl-propionyl)-phenyl]-methyl}-phenyl)-2-methyl-propan-1-one are dissolved in 160 g of dioxane in a 350 ml reaction flask. A solution of 0.77 g (2.4 mmol) of tetrabutylammonium bromide in 16 g of water is then added. The solution is heated at reflux, about 87° C. 71.6 g (0.269 mol) of 15% NaOH are then slowly added dropwise over about 6 hours and the conversion is checked by means of a $^1$H NMR spectrum. The yellowish reaction mixture is cooled and neutralised using 4.5 g of 16% HCl solution. The aqueous phase is separated off and the organic phase is washed with a small amount of water and concentrated. The crude product, 35.7 g of slightly yellowish oil, is seeded. The crystals are recrystallised from 240 g of toluene, washed and dried in vacuo. 21.4 g of white crystals are obtained, which melt at 130.1-131.9° C. In the $^1$H NMR spectrum there are found, exclusively, 2-hydroxy-1-(4-{hydroxy-[4-(2-hydroxy-2-methyl-propionyl)-phenyl]-methyl}-phenyl)-2-methyl-propan-1-one. The mother liquor is concentrated, resulting in 6.8 g of yellowish oil. The oil is purified over a silica gel column. A 1:1 mixture of ethyl acetate and mixed hexanes is used as mobile phase. A further 3.7 g of product are obtained.

Elemental analysis of the tris-hydroxy compound: (356.42)

|  | % C |  | % H |
|---|---|---|---|
| calculated: | 70.77 | calculated: | 6.79 |
| found: | 70.83 | found: | 6.80 |

EXAMPLE 8

Hydrolysis of the dichloromonobromo Compound 45.6 g (0.10 mol) of recrystallised 1-(4-{bromo-[4-(2-chloro-2-methyl-propionyl)-phenyl]-methyl}-phenyl)-2-chloro-2-methyl-propan-1-one are introduced into 200 g of dioxane in a 500 ml reaction flask and heated until dissolved. Then, at 31° C., a solution of 1.0 g (3.0 mmol) of tetrabutylammonium bromide in 20 g of water is added. Then 96 g (0.36 mol) of 15% NaOH are added dropwise over 30 minutes. The temperature increases from 31 to 39° C. The pH is between 10 and 11. The solution is heated at reflux, about 85° C. After three hours, the reaction is about 75% complete according to the $^1$H NMR spectrum. The reaction proceeds no further and, after a further three hours, is terminated. The emulsion is neutralised using 7.8 g of 16% HCl solution and the aqueous phase is separated off. The organic phase is washed with a small amount of water and concentrated. The crude product, 35.2 g of yellowish oil, is seeded. The crystals are crystallised from 100 g of toluene. 21.3 g of white crystals are obtained. In the $^1$H NMR spectrum there is found, exclusively, 2-hydroxy-1-(4-{hydroxy-[4-(2-hydroxy-2-methyl-propionyl)-phenyl]-methyl}-phenyl)-2-methyl-propan-1-one. The mother liquor is concentrated, resulting in 11.4 g of yellowish oil.

EXAMPLE 9

Hydrolysis of the dichloromonobromo Compound 68.4 g (0.15 mol) of recrystallised 1-(4-{bromo-[4-(2-chloro-2-methyl-propionyl)-phenyl]-methyl}-phenyl)-2-chloro-2-methyl-propan-1-one are dissolved in 300 g of dioxane in a 750 ml reaction flask and heated to 87° C. A solution of 1.5 g (4.7 mmol) of tetrabutylammonium bromide in 30 g of water is then added. Then, at 87° C., a total of 130 g (0.487 mol) of 15% NaOH are slowly added dropwise over about five hours. The conversion is checked by means of a ¹H NMR spectrum. Towards the end of the addition, the pH increases towards 10. The emulsion is cooled to 35° C. and is then neutralised using 5.1 g of 16% HCl solution. The two phases are separated in a separating funnel. The aqueous phase is extracted twice with 50 ml of ethyl acetate and the extract is evaporated using a vacuum rotary evaporator. 2.3 g of yellow oil are obtained. The organic phase is also concentrated using a vacuum rotary evaporator. 59.9 g of dark oil remain behind. The oil is dissolved in 35 g of ethyl acetate in the hot state and, in the warm state, diluted with 120 g of toluene in portions. On stirring to complete the reaction, the solution slowly crystallises. The crystals are filtered off, washed with toluene and dried. 25.5 g of pale beige crystals are obtained. In the ¹H NMR spectrum there is found, exclusively, 2-hydroxy-1-(4-{hydroxy-[4-(2-hydroxy-2-methyl-propionyl)-phenyl]-methyl}-phenyl)-2-methyl-propan-1-one. The mother liquor is concentrated, resulting in 26.7 g of reddish-yellow oil. This oil is resolved using a silica gel column. A 1:1 mixture of ethyl acetate and mixed hexanes is used as mobile phase. There are obtained two relatively large fractions, which crystallise. In the main fraction there are obtained a further 10.2 g of pure 2-hydroxy-1-(4-{hydroxy-[4-(2-hydroxy-2-methyl-propionyl)-phenyl]-methyl}phenyl)-2-methyl-propan-1-one. In the subsidiary fraction there are found 9.0 g of the bis-hydroxychloro compound 1-(4-{Chloro-[4-(2-hydroxy-2-methyl-propionyl)-phenyl]-methyl}-phenyl)-2-hydroxy-2-methyl-propan-1-one. The bis-hydroxychloro compound is not pure, however, and according to the ¹H NMR spectrum is also accompanied by the benzophenone derivative 2-hydroxy-1-{4-[4-(2-hydroxy-2-methyl-propionyl)-benzoyl]-phenyl}-2-methyl-propan-1-one.

Elemental analysis of the bis-hydroxychloro compound×1 H₂O: (374.87+18.02)

|  | % C |  | % H |  | % Cl |
|---|---|---|---|---|---|
| calculated | 64.20 | calculated | 6.41 | calculated | 9.02 |
| found | 64.25 | found | 6.44 | found | 8.92 |

EXAMPLE 10

Hydrolysis of Example 2c 68.4 g (0.15 mol) of recrystallised bis-[4-(2-chlor-2-methyl-propionyl)-phenyl]-brommethane are dissolved in 300 g of dioxane and heated to 80° C. A solution of 1.5 g (4.5 mmol) of tetrabutylammonium bromide in 30 g of water is then added. 112.8 g (0.423 mol) NaOH 15% are then added dropwise over two hours at 80° C. The pH value is pH 9-10. The reaction is monitored by means of ¹H NMR spectrum. The intermediate compound bis-[4-(2-hydroxy-2-methyl-propionyl)-phenyl]-chlormethan is obtained and the reaction does not proceed despite the addition of NaOH. The NaOH addition is now stopped. The aqueous phase (139 g) containing the salt is separated off. The remaining reaction mixture is now acid. Then a further amount of 20.5 g (0,077 mol) NaOH 15% is added at 80° C. to obtain a pH value of pH 8-9. The intermediate compound bis-[4-(2-hydroxy-2-methyl-propionyl)-phenyl]-chlormethane hydrolyses slowly. After cooling 16 g of NaCl 26.5% are added. The dioxane phase is separated off and concentrated. The oil obtained is mixed with 120 g of ethyl acetate at 60° C. and concentrated again. The oil now obtained is suspended in 180 g of toluene. The suspension is filtered off, washed with toluene and dried. Yield: 39.8 g of white crystals of bis-[4-(2-hydroxy-2-methyl-propionyl)-phenyl]-hydroxy methane, mp: 121-123° C. In the ¹H-NMR-Spectrum there is found quantitatively 2-hydroxy-1-(4-{hydroxy-[4-(2-hydroxy-2-methyl-propionyl)-phenyl]-methyl}-phenyl)-2-methyl-propane-1-one. The filtrate and the wash solutions are concentrated. Yield: 10.9 g of a reddish yellow oil.

EXAMPLE 11

Preparation of (6-{bis[4-(2-hydroxy-2-methyl-propionyl)-phenyl]-methoxycarbonylamino}-hexyl)-carbamic acid bis[4-(2-hydroxy-2-methyl-propionyl)-phenyl]-methyl ester bisurethane compound

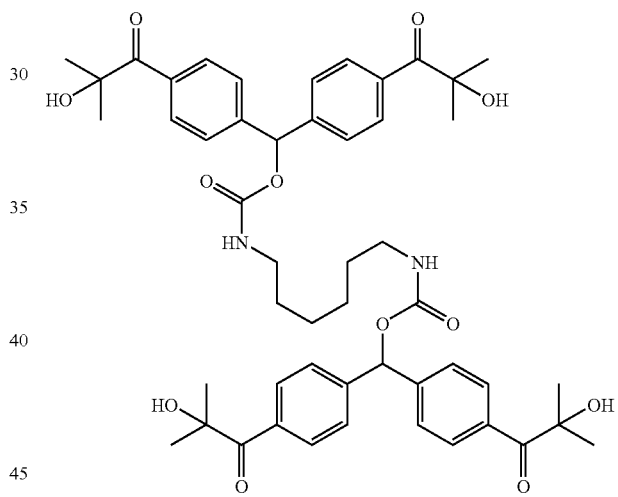

2.50 g (7.01 mmol) of recrystallised 2-hydroxy-1-(4-{hydroxy-[4-(2-hydroxy-2-methyl-propionyl)-phenyl]-methyl}-phenyl)-2-methyl-propan-1-one are dissolved in 15 ml of dioxane under nitrogen in a 50 ml multi-neck flask. One drop of dibutyltin dilaurate is then added. A solution of 0.59 g (3.51 mmol) of 1,6-hexamethylene diusocyanate in 10 ml of dioxane is then added dropwise. The mixture is then heated and the temperature is maintained at 50° C. for two hours and at 70° C. for three hours. The reaction is monitored by means of the ¹H NMR spectrum and thin-layer chromatography. The crude product is concentrated and purified over a silica gel column. A 2:1 mixture of ethyl acetate and mixed hexanes is used as mobile phase. 0.4 g of white crystals is obtained in the main fraction. They melt at 73-76° C. They are confirmed by means of the ¹H NMR spectrum as being the bisurethane derivative of the tris-hydroxy compound, (6-{bis[4-(2-hydroxy-2-methyl-propionyl)-phenyl]-methoxycarbonylamino}hexyl)-carbamic acid bis[4-(2-hydroxy-2-methyl-propionyl)-phenyl]-methyl ester.

EXAMPLE 12

Synthesis of (8{Bis-[4-(2-hydroxy-2-methyl-propionyl)-phenyl]-methoxycarbonylamino}-octyl)-carbamic acid bis-[4-(2-hydroxy-2-methyl-propionyl)-phenyl]-methyl ester

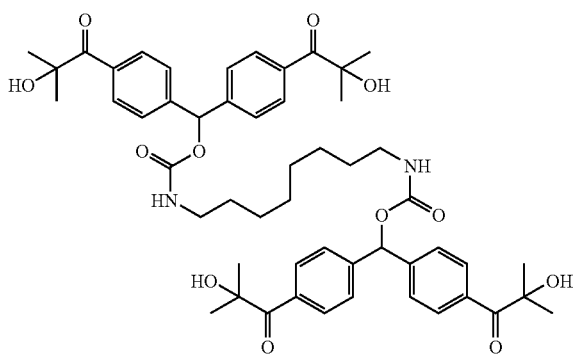

This compound was prepared according to the method described in example 11, using 1,8-diisocyanatooctane, and replacing 1,4-dioxane by tetrahydrofuran as solvent. The raw product was purified by column chromatography (SiO$_2$; hexane:ethyl acetate 1:1) and was obtained as a colorless solid, mp. 75-79° C. The structure was confirmed by $^1$H-NMR (CDCl$_3$): δ [ppm]: 8.01 (d, 8H), 7.42 (d, 8H), 6.82 (s, 2H, benzylic), 4.97 (t, 4H, NH), 3.91, (s, 4H, OH), 3.17 (m, 4H, CH$_2$N); 1.60 (s, 24H, CH$_3$), 1.48 (m, 4H), 1.2-1.3 (m, 8H).

EXAMPLE 13

Synthesis of (12-{Bis-[4-(2-hydroxy-2-methyl-propionyl)-phenyl]-methoxycarbonylamino}-dodecyl)-carbamic acid bis-[4-(2-hydroxy-2-methyl-propionyl)-phenyl]-methyl ester

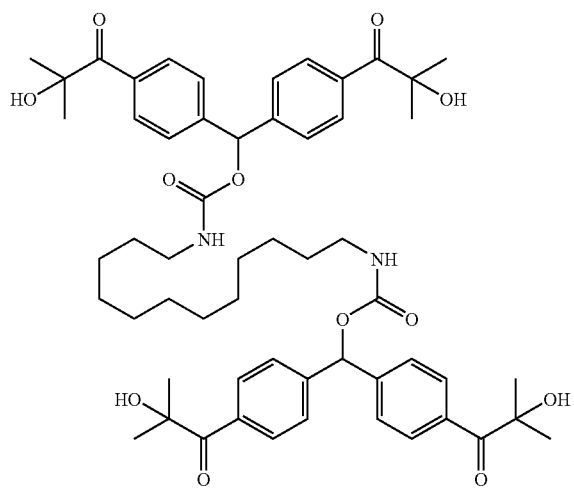

This compound was prepared according to the method described in example 11, using 1,12-diisocyanatododecane in tetrahydrofuran and 1,4-diazabicyclo[2.2.2]octane as catalyst. The raw product was purified by column chromatography (SiO$_2$; hexane:ethylacetate 1:1) and was obtained as a colorless, waxy solid, mp. 68-77° C. The structure was confirmed by $^1$H-NMR (CDCl$_3$): δ [ppm]: 8.01 (d, 8H), 7.42 (d, 8H), 6.82 (s, 2H, benzylic), 5.02 (t, 4H, NH), 3.94, (s, 4H, OH), 3.18 (m, 4H, CH$_2$N); 1.60 (s, 24H, CH$_3$), 1.52 (m, 4H), 1.2-1.3 (m, 16H).

Elemental analysis: C$_{56}$H$_{72}$N$_2$O$_{12}$ (965.20)

|  | % C |  | % H |  | % N |
|---|---|---|---|---|---|
| calculated | 69.69 | calculated | 7.52 | calculated | 2.90 |
| found | 69.35 | found | 7.64 | found | 2.76 |

EXAMPLE 14

Synthesis of {1-[3-(1-{Bis-[4-(2-hydroxy-2-methyl-propionyl)phenyl]-methoxycarbonylamino}-1-methyl-ethyl)-phenyl]-1-methyl-ethyl}-carbamic acid bis-[4-(2-hydroxy-2-methyl-propionyl)-phenyl]-methyl ester

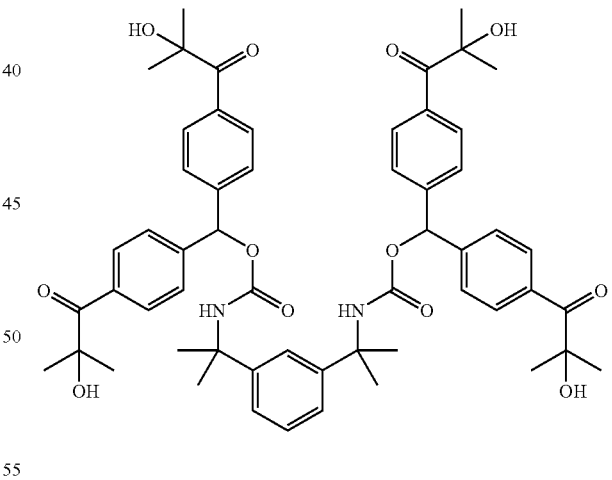

This compound was prepared according to the method described in example 11, using 1,3-bis(1-isocyanato-1-methylethyl)benzene, and replacing 1,4-dioxane by tetrahydrofuran as solvent. The raw product was purified by column chromatography (SiO$_2$; hexane:ethylacetate 1:1) and was obtained as a colorless solid, mp. 68-81. The structure was confirmed by $^1$H-NMR (CDCl$_3$): δ [ppm]: 8.01 (d, 8H), 7.42 (d, 8H), 6.9-7.3 (m, 4H), 6.75 (s, 2H, benzylic), 5.33 (s, 4H, NH), 3.91, (s, 4H, OH), 1.60 (bs, 36H, CH$_3$).

EXAMPLE 15

Preparation of 1-(4-{[2-(2-{bis[4-(2-hydroxy-2-methyl-propionyl)-phenyl]-methoxy}-ethoxy)-ethoxy]-[4-(2-hydroxy-2-methyl-propionyl)-phenyl]-methyl}-phenyl)-2-hydroxy-2-methyl-propan-1-one, diethylene glycol diether

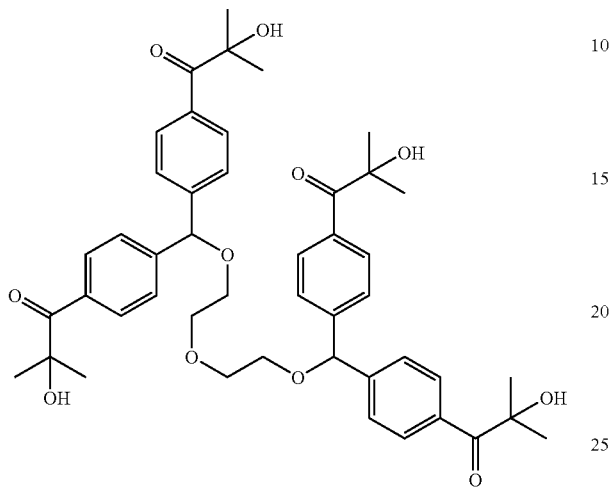

2.50 g (7.01 mmol ) of recrystallised 2-hydroxy-1-(4-{hydroxy-[4-(2-hydroxy-2-methyl-propionyl)-phenyl]-methyl}-phenyl)-2-methyl-propan-1-one, 0.372 g (3.51 mmol) of diethylene glycol and 0.013 g of toluenesulfonic acid monohydrate are introduced into a 10 ml two-necked round-bottom flask and heated at 150° C. After five hours, practically no more starting product is present in the ¹H NMR spectrum. The product is purified over a silica gel column. A 3:1 mixture of ethyl acetate and mixed hexanes is used as mobile phase. 0.4 g of thick oil is obtained in the main fraction and is confirmed by means of the ¹H NMR spectrum as being the diethylene glycol diether of the tris-hydroxy compound, 1-(4-{[2-(2{bis[4-(2-hydroxy-2-methyl-propionyl)-phenyl]-methoxy}-ethoxy)-ethoxy]-[4-(2-hydroxy-2-methyl-propionyl)-phenyl]-methyl}phenyl)-2-hydroxy-2-methyl-propan-1-one.

EXAMPLE 16

Hydrolyse of the dichlormonobromine Compound with triethylene glycol

2-Hydroxy-1-(4-{{2-[2-(2-hydroxy-ethoxy)-ethoxy]-ethoxy}-[4-(2-hydroxy-2-methyl-propionyl)-phenyl]-methyl}-phenyl)-2-methyl-propan-1-one

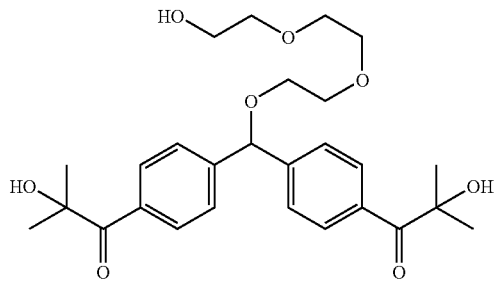

1.2 g (2.6 mmol) of the dichlormonobromine compound 1-(4-{bromo-[4-(2-chloro-2-methyl-propionyl)-phenyl]-methyl}-phenyl)-2-chloro-2-methyl-propane-1-one and 0.8 g (5.3 mmol) tri-ethylene glykol are dissolved in 3 g of dioxane. A small amount of p-toluene sulfonic acid is added. The reaction mixture is treated for two hours at 110° C. in a microwave reactor. ("Emry Optimizer"; Personal Chemistry, Uppsala, Sweden ). The reaction mixture is concentrated. 10 ml of dioxane and 1.4 g (10.5 mmol) NaOH, 30% are added. The reaction mixture is heated to 80° C. for three hours. The pH value is adjusted to pH 1-2 with 16% HCl. 0.5 g of NaOH (15%) are added to obtain a pH value of circa 7. The reaction mixture is concentrated. The crude product is extracted with toluene. and purified over a silica column. Yield : 0.8 g 2-hydroxy-1-(4-{{2-[2-(2-hydroxy-ethoxy)-ethoxy]-ethoxy}-[4-(2-hydroxy-2-methyl-propionyl)-phenyl]-methyl}-phenyl)-2-methyl-propan-1-one.

EXAMPLE 17

Aminolysis of the dichlormonobromine compound with 2-methylaminoethanol 2-Hydroxy-1-(4-{[(2-hydroxy-ethyl)-methyl-amino]-[4-(2-hydroxy-2-methyl-propionyl)-phenyl]-methyl}-phenyl)-2-methyl-propan-1-one

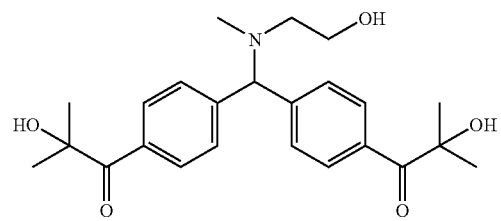

6.8 g (15 mmol) of the dichlormonobromine compound, 1-(4-{-bromo-[4-(2-chloro-2-methyl-propionyl)-phenyl]-methyl}-phenyl)-2-chloro-2-methyl-propane-1-on are dissolved in 35 g of dioxane. 1.2 g (16 mmol) 2-Methylaminoethanol are added. The solution is heated to 85° C. The reaction is monitored by means of ¹H-NMR spectrum. Another 1.2 g (16 mmol) 2-methyl-aminoethanol are added for complete reaction. The solution obtained is added under nitrogen to an aqueous NaOH solution.(15%). The reaction mixture is heated to 80° C. and stirred for two hours. The reaction mixture is cooled. 11 g HCl (16%) is added to adjust the pH-value to 1-2. 4.6 g NaOH (15%) is added to adjust the pH-value to pH 8. The reaction mixture is concentrated using a vacuum rotary evaporator. The oil obtained is extracted with 60 ml of toluene and concentrated again. Yield: 5.6 g of a yellow oil. In the ¹H-NMR-Spectrum it is confirmed that the product obtained is 2-hydroxy-1-(4-{[(2-hydroxy-ethyl)-methyl-amino]-[4-(2-hydroxy-2-methyl-propionyl)-phenyl]-methyl}-phenyl)-2-methyl-propane-1-one.

EXAMPLE 18

Synthesis of 2-Hydroxy-1-(4-{hydroxy-[4-(1-hydroxy-cyclohexanecarbonyl)-phenyl]-methyl}-phenyl)-2-methyl-propan-1-one

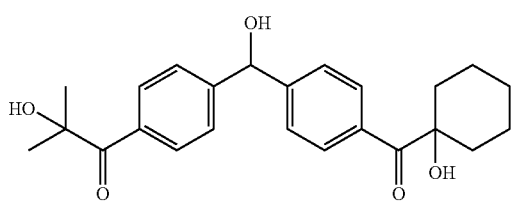

18.a 1-[4-(4-Cyclohexanecarbonyl-benzyl)-phenyl]-2-methyl-propan-1-one

In a 200 ml sulfonation flask under nitrogen, 11.9 g (0.05 mol) of 1-(4-benzyl-phenyl)-2-methyl-propan-1-one (compound known from patent application DE3008411) and 8.6 g (0.055 mol) isobutyryl chloride were dissolved in 50 ml 1,2-dichlorobenzene. The solution was cooled to 0° C. in an ice bath, and treated with 15.0 g (0.11 mol) aluminum chloride added by portions over 2.5 h, keeping the temperature below 5° C. The reaction mixture became progressively more viscous and dark brown. After stirring for 30 h at 0° C., the mixture was poured onto a mixture of 300 g ice and 35 g of aqueous 32% hydrogen chloride, and stirred during 1 h. Dichloromethane (70 ml) was added, the organic layer was separated, washed to pH 5 with deionized water, dried over magnesium sulfate, and concentrated by evaporation to give 10.55 of a yellow oil that was purified by flash column chromatography on silica gel (hexane:ethyl acetate 7:1). 9.21 of 1-[4-(4-Cyclohexanecarbonyl-benzyl)-phenyl]-2-methyl-propan-1-one were obtained as a yellow oil and used for the next step. The structure was confirmed by $^1$H-NMR (CDCl$_3$): δ [ppm]: 7.87-7.91 (m, 4H), 7.23-7.28 (m, 4H), 4.07 (s, 2H, benzylic), 3.52 (m, 1H, Me-CH-Me), 3.23 (m, 1H, cyclohexyl), 1.26-1.88 (m, 10H), 1.20 (d, 6H).

18.b 2-Bromo-1-(4-{bromo-[4-(1-bromo-cyclohexanecarbonyl)-phenyl]-methyl}-phenyl)-2-methyl-propan-1-one 9.15 g (26.2 mmol) of 1-[4-(4-Cyclohexanecarbonyl-benzyl)-phenyl]-2-methyl-propan-1-one were dissolved in 80 ml carbon tetrachloride. 9.2 g bromine (57.8 mmol) diluted with 5 ml carbon tetrachloride were added dropwise at 23° C., and the reaction mixture was stirred during 4 h with evolution of hydrogen bromide. Then the mixture was heated to 60° C., and 4.2 g (26.2 mmol) bromine were added dropwise over 1 h with simultaneous irradiation from a 100 W light bulb. After stirring for 2 h, the mixture was cooled to 20° C., washed with sodium hydrogene carbonate and concentrated by evaporation. The crude tribromide was obtained as a dark yellow oil (14.85 g) and used for the next step without further purification.

18.c 2-Hydroxy-1-(4-{hydroxy-[4-(1-hydroxy-cyclohexanecarbonyl)-phenyl]-methyl}-phenyl)-2-methyl-propan-1-one 14.85 g of crude 2-Bromo-1-(4-{bromo-[4-(1-bromo-cyclohexanecarbonyl)-phenyl]-methyl}-phenyl)-2-methyl-propan-1-one were dissolved in 80 ml dioxan, and 0.3 g tetra(n-butyl)ammonium bromide dissolved in 8 ml water were added. The yellow solution was heated to 90° C., and 24.4 g of 15% aqueous sodium hydroxide were added dropwise over 5 h. The reaction mixture was cooled and neutralized with 10% HCl. 50 ml water were added, the organic phase was separated, and the aqueous phase was extracted with 70 ml ethyl acetate. The combined organic phases were dried with brine and magnesium sulfate, and concentrated by evaporation. A brown oil (9.5 g) was obtained and purified by flash column chromatography (SiO$_2$; hexane:ethyl acetate 2:1) to give 3.2 g of pure 2-hydroxy-1-(4-{hydroxy-[4-(1-hydroxy-cyclohexanecarbonyl)-phenyl]-methyl}-phenyl)-2-methyl-propan-1-one as a yellowish resin that solidified upon standing (mp: 115-118° C.). The structure was confirmed by $^1$H-NMR (CDCl$_3$): δ [ppm]: 7.98-8.02 (m, 4H), 7.44-7.50 (m, 4H), 5.92 (s, 1H, benzylic), 4.01 (s, 1H, OH), 3.30 (s, 1H, OH), 2.68 (s, 1H, OH), 1.81-2.04 (m, 2H), 1.63-1.81 (m, 3H), 1.60 (s, 6H), 1.3-1.4 (m, 1H).

Elemental analysis: C$_{24}$H$_{28}$O$_5$: (396.49)

|  | % C |  | % H |
|---|---|---|---|
| calculated | 72.71 | calculated | 7.12 |
| found | 72.31 | found | 7.14 |

EXAMPLE 19

EXAMPLE 19a

1-[4-(4-butyryl-benzyl)-phenyl]-butan-1-one

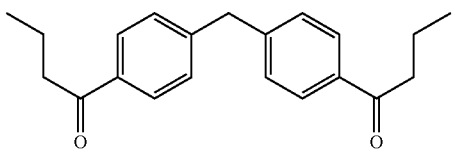

67.3 g (0.40 mol) diphenylmethane, 98.0 g (0.92 mol) butyryl chloride and 200 g chlorobenzene are combined and cooled to 15-20° C. Then, over the course of about three hours, at an internal temperature of 20-25° C., 128.0 g (0.96 mol) of aluminium chloride are added in small portions. HCl gas is evolved. Stirring is then carried out at an internal temperature of 20-25° C. for about 16 hours. The reaction mixture is then heated to 45° C. for another three hours. At the end all the aluminium chloride has dissolved. The dark-red reaction mixture is then poured into ice and water and stirred to complete the reaction. The two phases are separated in a separating funnel. The organic phase is washed with water and then concentrated for a short time in a vacuum rotary evaporator at about 60° C. and about 25 mbar, resulting in 143 g of a yellow liquid which starts to crystallise. The oil is diluted with 300 g of hexane and recrystallised. 84.0 g of white crystals are obtained which melt at 84-85° C. In the $^1$H-NMR-spectrum there is found isomer-free 1-[4-(4-butyryl-benzyl)-phenyl]-butane-1-on. In the $^1$H-NMR-spectrum of the concentrated mother liquor (44.2 g yellow oil) there is found a mixture of isomers.

EXAMPLE 19b

2-Bromo-1-(4-{bromo-[4-(2-bromo-butyryl)-phenyl]-methyl}-phenyl)-butane-1-on

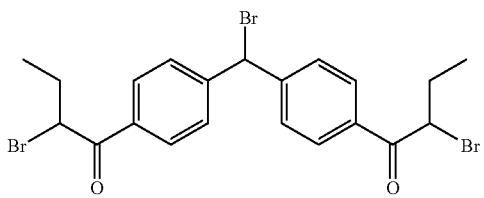

32.1 g (0.104 mol) recrystallised 1-[4-(4-butyryl-benzyl)-phenyl]-butane-1-on are dissolved in 120 ml of carbon tetrachloride in a 0.75 litre reaction flask and heated 40° C. 31.7 g (0.20 mol) of bromine are then added dropwise over about two hours at 45-50° C. The colour of the solution is discharged continuously and HBr gas is evolved. Later on, the colour of the solution is discharged more slowly and it remains red. The reaction flask is wrapped in aluminium foil and irradiated with two 150 Watt daylight lamps. 16.0 g (0.10 mol) of bromine diluted with 25 ml carbon tetrachloride are then added dropwise over about four hours. The colour of the solution is discharged continuously and HBr gas is evolved. The temperature rises to about 62° C. A further 8.0 g (0.05 mol) of bromine diluted with 20 ml carbon tetra-chloride are added dropwise. The solution is concentrated. The crude product (66.4 g of brown oil) is purified over a silica gel column. A 1:6 mixture of ethyl acetate and mixed hexanes is used as mobile phase. 28.0 g of yellow oil is obtained in the main fraction and 7.9 g of yellow oil is obtained in the second fraction. In the $^1$H-NMR-pectrum there is found (2-bromo-1-(4-{bromo-[4-(2-bromo-butyryl)-phenyl]-methyl}-phenyl)-butane-1-on ) which is used for the next reaction step.

EXAMPLE 19c

2-Dimethylamino-1-(4-{dimethylamino-[4-(2-dimethylamino-butyryl)-phenyl]-methyl}-phenyl)-butan-1-one

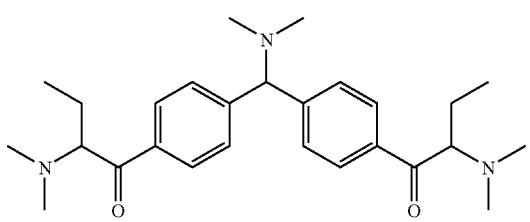

14.0 g (0.026 mol ) 2-bromo-1-(4{bromo-[4-(2-bromo-butyryl)-phenyl]-methyl}-phenyl)-butane-1-on (product of the main fraction) are dissolved in 70 ml methylethyl ketone and heated to 50° C. 17.4 g (0.15 mol) dimetyl amine (40% in water) is added dropwise over one hour. 7.2 g NaOH 30% are added over one hour. The aqueous phase is separated using a separating funnel. 50 ml of saturated NaOH are added to the organic phase. The pH value is adjusted to pH 8-9 with acetic acid. The organic phase is concentrated using in a vacuum rotary evaporator. 11.0 g of reddish crystals are obtained. Recrystallisation is carried out in 40 g of hexane. Yield: 6.6 g of yellow crystals (mp 115-117° C.). In the $^1$H-NMR-spectrum there are found pure 2-dimethylamino-1-(4{dimethylamino-[4-(2-dimethylamino-butyryl)-phenyl]-methyl}phenyl)-butane-1-on. From the mother liquor 3.4 g of a reddish oil is obtained.

Elemental analysis of the trisamino compound $C_{27}H_{39}N_3O_2$: (437,63)

| | % C | | % H | | % N |
|---|---|---|---|---|---|
| calculated | 74.10 | calculated | 8.98 | calculated | 9.60 |
| found | 73.90 | found | 8.94 | found | 9.54 |

EXAMPLE 20

2-Benzyl-1-(4-{[4-(2-benzyl-2-dimethylamino-butyryl)-phenyl]-dimethylamino-methyl}-phenyl)-2-dimethylamino-butan-1-one

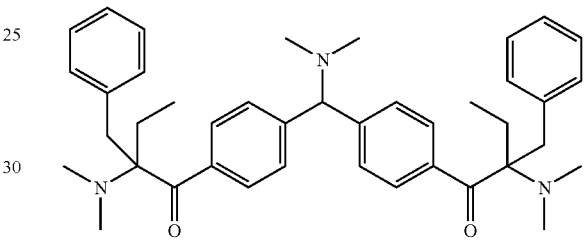

6.3 g (14.4 mmol) of recrystallised 2-dimethylamino-1-(4-{dimethylamino-[4-(2-dimethyl-amino-butyryl)-phenyl]-methyl}-phenyl)-butane-1-on are dissolved in 60 ml of methylethy ketone and heated to 60° C. 7.8 g (45.3 mmol) of benzylbromid are added dropwise and stirred over four hours at 60-65° C. Then 12.1 g NaOH (30%) are added dropwise. The suspension is maintained at 60° C. for two hours. The suspension is then diluted with 40 ml of water. The aqueous phase is separated. 50 ml of saturated NaOH are added to the organic phase. The organic phase is concentrated using in a vacuum rotary evaporator. 11.2 g of yellow oil are obtained. The product is monitored by means of the $^1$H-NMR-sectrum. The crude product is purified over a silica gel column. Mobile phase: ethylacetate:hexane 1:3. 3.8 g of 2-benzyl-1-(4-{ [4-(2-benzyl-2-dimethylamino-butyryl)-phenyl]-dimethylamino-methyl}-phenyl)-2-dimethylamino-butane-1-on are obtained. (yellow oil)

Elemental analysis of the compound $C_{41}H_{51}N_3O_2$: (617, 88)

| | % C | | % H | | % N |
|---|---|---|---|---|---|
| calculated | 79.70 | calculated | 8.32 | calculated | 6.80 |
| found | 79.56 | found | 8.29 | found | 6.59 |

Application Examples

UV-curable Overprint Coating (Containing Amino Acrylate)

The compound, in accordance with the invention, of Example 6 was tested for its suitability as a photoinitiator in a UV-curable overprint coating (OPV) and compared with commercially available initiators. The composition of the OPV can be found in the Table below.

| Component | % by weight |
| --- | --- |
| Ebecryl 605 | 30.0 |
| Ebecryl 7100 | 10.0 |
| Ebecryl 40 | 5.0 |
| OTA 480 | 30.0 |
| TPGDA | 24.0 |
| Ebecryl 1360 | 0.5 |
| Dow Corning 57 | 0.5 |
| Σ | 100.0 |

OTA 480: glycerol propoxylate triacrylate (UCB)
TPGDA: tripropylene glycol diacrylate (UCB)
Ebecryl 605: bisphenol A epoxy acrylate, diluted with 25% TPGDA (UCB)
Ebecryl 7100: amine acrylate (UCB)
Ebecryl 40: pentaerythritol ethoxylate tetraacrylate (UCB)
Ebecryl 1360: hexafunctional silicone acrylate (UCB)
Dow Corning 57: silicone additive, flow improver (DOW Corning)

The samples were applied in a layer thickness of 6 μm to white card using a knife and then cured using a UV exposure device (2 medium-pressure mercury lamps of 120 W/cm, variable-speed conveyor belt; IST). Immediately after exposure, the resistance of the coating surface to wiping was determined by means of a paper towel. The curing speed is the maximum conveyor belt speed of the exposure device, in m/min, at which the coating surface remains resistant to wiping.

The results obtained can be found in the following Table.

| 6% photoinitiator | Curing speed [m/min] |
| --- | --- |
| DAROCUR 1173 | 70 |
| IRGACURE 184 | 50 |
| Example 6 | 110 |

DAROCUR 1173: 2-hydroxy-2-methyl-1-phenyl-propanone (Ciba Specialty Chemicals)
IRGACURE 184: 1-hydroxy-cyclohexyl-phenyl ketone (Ciba Specialty Chemicals).

UV-curable Flexographic Printing Ink

The compounds, in accordance with the invention were tested for its suitability as a photoinitiator in a UV-curable flexographic printing ink and compared with commercially available initiators. The composition of the printing ink can be found in the Table below.

| Component | % by weight |
| --- | --- |
| IRR 440 | 26.9 |
| OTA 480 | 19.0 |
| Ebecryl 645 | 18.0 |
| hexanediol diacrylate | 13.0 |
| Ebecryl 220 | 10.0 |
| Ebecryl 168 | 1.3 |

-continued

| Component | % by weight |
| --- | --- |
| Dow Corning 57 | 0.7 |
| Irgalite Blue GLO | 11.1 |
| Σ | 100.0 |

IRR 440: acrylate oligomer (UCB)
Ebecryl 645: modified bisphenol A epoxy acrylate (UCB)
HDDA: hexanediol diacrylate (UCB)
Ebecryl 220: hexafunctional aromatic urethane acrylate (UCB)
Ebecryl 168: acid methacrylate, adhesion agent (UCB)
Dow Corning 57: silicone additive, flow improver (DOW Corning)
Irgalite Blue GLO: blue phthalocyanine pigment (Ciba Specialty Chemicals)

The samples were printed on white PE film at 1.38 g/m² (corresponding to an optical density of 1.45) using a Prüfbau test printing apparatus and then cured using a UV exposure device (1 medium-pressure mercury lamp of 120 W/cm, variable-speed conveyor belt; IST). The samples thereby obtained were tested for through-curing (TC) and surface-curing (SF). The Table below shows the results obtained.

| Product | Concentration [% by weight] | TC [m/min] | SF [m/min] |
| --- | --- | --- | --- |
| Example 6 | 7.0 | 200 | 180 |
| Example 12 | 7.0 | 10 | 10 |
| Example 13 | 7.0 | 60 | 70 |
| Example 14 | 7.0 | 50 | 50 |
| Irgacure 907/ Quantacure ITX | 6.0/0.5 | 100 | 100 |
| Irgacure 369 | 7.0 | 100 | 170 |

Irgacure 907: 2-methyl-1[4-(methylthio)phenyl]-2-(4-morpholinyl)-1-propanone (Ciba Specialty Chemicals)
Quantacure ITX: isopropyl thioxanthone (Lambson)
Irgacure 369: 2-benzyl-2-dimethylamino-1-(4-morpholinophenyl)-butan-1-one (Ciba Specialty Chemicals)

UV-curable Inkjet Ink

The compound, in accordance with the invention, of Example 8 was tested for its suitability as a photoinitiator in a UV-curable inkjet ink and compared with commercially available initiators.

For that purpose, a pigment concentrate was first prepared in accordance with the Table below, using a bead mill. Then 15 parts of concentrate were mixed with 79.5 parts of reactive diluent (Viajet 400, UCB), 6 or 8 parts of initiator and 0.4 part of flow improver (Dow Corning 57, Dow Corning) to form the finished ink.

| Component | Parts |
| --- | --- |
| Viajet 100 | 78.45 |
| Irgalite Blue GLO | 20.00 |
| Florstab UV1 | 1.00 |
| Solsperse 5000 | 0.55 |

ViaJet 100: base resin for the preparation of concentrates for UV-curable inkjet inks (UCB)
Irgalite Blue GLO: blue phthalocyanine pigment (Ciba Specialty Chemicals)
Florstab UV1: storage stabiliser for UV-curable systems (Kromachem)
Solsperse 5000: dispersant (Avecia)

The inks were applied in a layer thickness of 12 μm to metallised paper using a knife and cured under the UV exposure system (2 medium-pressure mercury lamps of 120 W/cm, variable-speed conveyor belt; IST). Immediately after exposure, the resistance of the coating surface to wiping was determined by means of a paper towel. The curing speed is the maximum conveyor belt speed of the exposure device, in m/min, at which the surface of the printing ink remains resistant to wiping.

| Photoinitiator | Curing speed [m/min] | |
|---|---|---|
| | 6 parts of initiator | 8 parts of initiator |
| Irgacure 369 | 20 | 30 |
| Irgacure 907/ITX (4:1) | 20 | 30 |
| Example 8 | 30 | 70 |

Volatility Assessment

The volatility of the photoinitiator from example 6 was determined by thermogravimetric analysis (TGA) and compared with the volatiliy of reference photoinitiators. Measurements were carried out on a Mettler Toledo Star$^\ominus$ System with neat photoinitiators (ca. 10 mg) under nitrogen, starting at 35° C., and heating at a rate of 10° C./min. The temperature at which weight loss reached 5, 10, and 15% was determined from the TGA plots.

| Product | 5% weight loss [° C.] | 10% weight loss [° C.] | 15% weight loss [° C.] |
|---|---|---|---|
| Example 6 | 324 | 344 | 355 |
| Darocur 1173 | 106 | 120 | 128 |
| Irgacure 184 | 163 | 183 | 196 |
| Irgacure 2959 | 234 | 254 | 262 |

The invention claimed is:
1. A photoinitiator of formula I or II

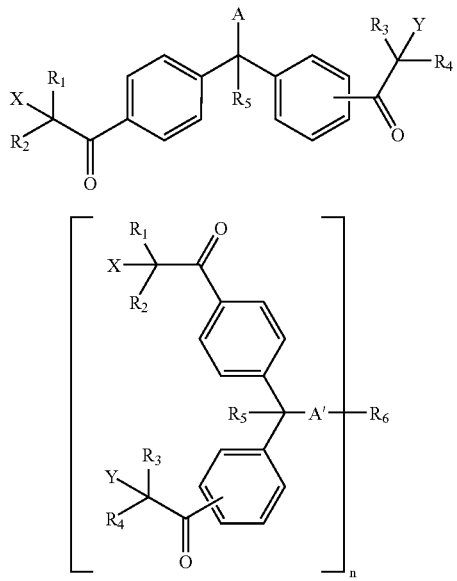

wherein $R_1$, $R_2$, $R_3$ and $R_4$ are each independently of the others $C_1$-$C_8$alkyl; $C_1$-$C_4$alkyl substituted by OH, $C_1$-$C_4$alkoxy, —CN, —COO($C_1$-$C_8$alkyl), ($C_1$-$C_4$alkyl)-COO—, benzyl, phenyl or by —N($R_{13}$)($R_{14}$);

$C_3$-$C_6$alkenyl, benzyl, —CH$_2$—C$_6$H$_4$—(C$_1$-C$_4$alkyl) or phenyl; or $R_1$ and $R_2$ together and/or $R_3$ and $R_4$ together are unbranched or branched $C_2$-$C_9$alkylene or $C_3$-$C_6$-oxa- or -aza-alkylene;

$R_5$ is hydrogen, $C_1$-$C_8$alkyl, $C_3$-$C_6$alkenyl, benzyl, —CH$_2$—C$_6$H$_4$—(C$_1$-C$_4$alkyl) or phenyl;

A is Cl, Br, —O—$R_7$, —N$R_8$$R_9$ or —S—$R_{16}$;

A' is —O—, —NH— or —N$R_8$—;

X and Y are each independently of the other —O—$R_{10}$ or —N($R_{11}$)($R_{12}$);

n is an integer from 1 to 10, $R_6$ is an n-valent radical of linear or branched $C_2$-$C_{20}$alkyl the carbon chain of which may be interrupted by cyclohexanediyl, phenylene, —CH(OH)—, —C(C$_2$H$_5$)(CH$_2$—CH$_2$—OH)—, —C(CH$_3$)(CH$_2$—CH$_2$—OH)—, —C(CH$_2$—CH$_2$—OH)$_2$—, —N(CH$_3$)—, —N(C$_2$H$_5$)—, —N(CH$_2$—CH$_2$—OH)—, —CO—O—, —O—CO—, —O—CO—NH, NH—CO—O—, —P(CH$_2$—CH$_2$—OH)—, —P(O)(CH$_2$—CH$_2$—OH)—, —O—P(O—CH$_2$—CH$_2$—OH)—O—, —O—P(O)(O—CH$_2$—CH$_2$—OH)—O—, —O-cyclohexanediyl-C(CH$_3$)$_2$-cyclohexanediyl-O—, —O-phenylene-C(CH$_3$)$_2$-phenylene-O—, —O-phenylene-CH$_2$-phenylene-O—, —Si(CH$_3$)$_2$—, —O—Si(CH$_3$)$_2$—O—, —O—Si(CH$_3$)(O—CH$_3$)—O—, —Si(CH$_3$)($R_{17}$)—O—Si(CH$_3$)($R_{18}$)—, 5-(2-hydroxyethyl)-[1,3,5]triazinane-2,4,6-trione-1,3-diyl and/or by from one to nine oxygen atoms, or $R_6$ is an n-valent radical of linear or branched —CO—NH—(C$_2$-C$_{16}$alkylene)-(NH—CO)$_{n-1}$— or linear or branched —CO—NH—(C$_0$-C$_9$alkylene)-(NH—CO)$_{n-1}$— which may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl, 3-(6-isocyanatohexyl)-biuret-1,5-diyl or 5-(6-isocyanatohexyl)-[1,3,5]triazinane-2,4,6-trione-1,3-diyl radical(s), or $R_6$ is an n-valent radical of linear or branched —CO-(C$_0$-C$_{12}$alkylene)-(CO)$_{n-1}$-and the alkylene may be interrupted by oxygen, phenylene, cyclohexanediyl or by norbornanediyl; or $R_6$ is an n-valent radical of linear or branched —C$_2$-C$_{50}$alkylene the carbon chain of which is interrupted by one to 15 oxygen, and may be subsituted by OH or NH$_2$;

$R_7$ is hydrogen, —Si(C$_1$-C$_6$alkyl)$_3$, $C_1$-$C_{12}$alkyl, $R_{21}$, $C_2$-$C_{18}$acyl, —CO—NH—$C_1$-$C_{12}$alkyl, $C_2$-$C_{20}$hydroxyalkyl, $C_2$-$C_{20}$methoxyalkyl, 3-(C$_1$-C$_{18}$alkoxy)-2-hydroxy-propyl, 3-[1,3,3,3-tetramethyl-1-[(trimethylsilyl)oxy]disiloxanyl]-propyl, 2,3-dihydroxy-propyl or linear or branched $C_2$-$C_{21}$hydroxyalkyl or (C$_1$-C$_4$alkoxy)-$C_2$-$C_{21}$alkyl the carbon chain of which is interrupted by from one to nine oxygen atoms;

$R_8$ and $R_9$ are each independently of the other hydrogen, $C_1$-$C_{12}$alkyl; $C_2$-$C_4$alkyl substituted by one or more of the groups OH, $C_1$-$C_4$alkoxy, —CN, —COO(C$_1$-$C_4$alkyl); $C_3$-$C_5$alkenyl, cyclohexyl or $C_7$-$C_9$phenylalkyl, or when $R_9$=H or methyl, $R_8$ is also $C_2$-$C_{50}$alkyl substituted by one or more of the groups methyl, ethyl, OH, NH$_2$, and is interrupted by one or more oxygen, —NH—, cyclohexanediyl, norbornanediyl or phenylene, or $R_8$ and $R_9$ together are unbranched or branched $C_3$-$C_9$alkylene which may be interrupted by —O— or by —N($R_{15}$)—;

$R_{10}$ is hydrogen, $-Si(C_1-C_6alkyl)_3$, $C_1-C_8alkyl$, $C_3-C_6alkenyl$ or benzyl, $R_{11}$ and $R_{12}$ are each independently of the other $C_1-C_{12}alkyl$; $C_2-C_4alkyl$ substituted by one or more of the groups OH, $C_1-C_4alkoxy$, $-CN$, $-COO(C_1-C_4alkyl)$; $C_3-C_5alkenyl$, cyclohexyl or $C_7-C_9phenylalkyl$, or $R_{11}$ and $R_{12}$ together are unbranched or branched $C_3-C_9alkylene$ which may be interrupted by $-O-$ or by $-N(R_{15})-$;

$R_{13}$ and $R_{14}$ are each independently of the other hydrogen, $C_1-C_{12}alkyl$; $C_2-C_4alkyl$ substituted by one or more of the groups OH, $C_1-C_4alkoxy$, $-CN$, $-COO(C_1-C_4alkyl)$; $C_3-C_5alkenyl$, cyclohexyl or $C_7-C_9phenylalkyl$, or $R_{13}$ and $R_{14}$ together are unbranched or branched $C_3-C_9alkylene$ which may be interrupted by $-O-$ or by $-N(R_{15})-$;

$R_{15}$ is hydrogen, $C_1-C_4alkyl$, allyl, benzyl, $C_1-C_4hydroxyalkyl$, $-CH_2CH_2-COO(C_1-C_4alkyl)$ or $-CH_2CH_2CN$;

$R_{16}$ is $C_1-C_{18}alkyl$, hydroxyethyl, 2,3-dihydroxypropyl, cyclohexyl, benzyl, phenyl, $C_1-C_{12}alkylphenyl$, $-CH_2-COO(C_1-C_{18}alkyl)$, $-CH_2CH_2-COO(C_1-C_{18}alkyl)$ or $-CH(CH_3)-COO(C_1-C_{18}alkyl)$;

$R_{17}$ and $R_{18}$ are each independently of the other a monovalent radical methyl, $-O-Si(CH_3)_3$, $-O-Si(CH_3)_2-O-Si(CH_3)_3$, $-O-Si(CH_3)[-(CH_2)_p-OH]-O-Si(CH_3)$ or a bivalent radical $-O-Si(CH_3)_2-$, $-O-Si(CH_3)[-(CH_2)_p-OH]-$, $-O-Si(CH_3)(R_{19})-$, $-O-Si(CH_3)(R_{20})-$ and form chains;

$R_{19}$ and $R_{20}$ are each independently of the other a monovalent radical methyl, $-O-Si(CH_3)_3$, $-O-Si(CH_3)_2-O-Si(CH_3)_3$, $-O-Si(CH_3)[-(CH_2)_p-OH]-O-Si(CH_3)$ or a bivalent radical $-O-Si(CH_3)_2-$, $-O-Si(CH_3)[-(CH_2)_p-OH]-$, and extend chains and, when $R_{19}$ and $R_{20}$ are linked into a ring, $-(R_{19})-(R_{20})-$ is the bridge $-O-$;

$R_{21}$ is, independently of formula I, a radical of formula p is an integer from 2 to 12, it being possible for the carbon chain of the alkylene to be interrupted by from one to three oxygen atoms.

2. A photoinitiator according to claim 1 of formula III or IV

III

IV wherein $R_1$, $R_2$, $R_3$ and $R_4$ are each independently of the others $C_1-C_8alkyl$, $C_3-C_6alkenyl$, benzyl, $-CH_2-C_6H_4-(C_1-C_4alkyl)$ or phenyl, or $R_1$ and $R_2$ together and/or $R_3$ and $R_4$ together are unbranched or branched $C_2-C_9alkylene$;

$R_5$ is hydrogen, $C_1-C_8alkyl$, $C_3-C_6alkenyl$, benzyl, $-CH_2-C_6H_4-(C_1-C_4alkyl)$ or phenyl;

n is an integer from 1 to 10; and $R_6$ is an n-valent radical of linear or branched $C_2-C_{20}alkyl$ the carbon chain of which may be interrupted by cyclohexanediyl, phenylene, $-CH(OH)-$, $-C(C_2H_5)(CH_2-CH_2-OH)-$, $-C(CH_3)(CH_2-CH_2-OH)-$, $-C(CH_2-CH_2-OH)_2-$, $-N(CH_3)-$, $-N(C_2H_5)-$, $-N(CH_2-CH_2-OH)-$, $-CO-O-$, $-O-CO-$, $-P(CH_2-CH_2-OH)-$, $-P(O)(CH_2-CH_2-OH)-$, $-O-P(O-CH_2-CH_2-OH)-O-$, $-O-P(O)(O-CH_2-CH_2-OH)-O-$, $-O-cyclohexanediyl-C(CH_3)_2-cyclohexanediyl-O-$, $-O-phenylene-C(CH_3)_2-phenylene-O-$, $-O-phenylene-CH_2-phenylene-O-$, $-Si(CH_3)_2-$, $-O-Si(CH_3)_2-O-$, $-O-Si(CH_3)(O-CH_3)-O-$, $-Si(CH_3)(R_{17})-O-Si(CH_3)(R_{18})-$, 5-(2-hydroxyethyl)-[1,3,5]triazinane-2,4,6-trione-1,3-diyl and/or by from one to nine oxygen atoms, or $R_6$ is an n-valent radical of linear or branched $-CO-NH-(C_2-C_9alkylene)-(NH-CO)_{n-1}-$ or linear or branched $-CO-NH-(C_0-C_9alkylene)-(NH-CO)_{n-1}-$ which may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl, 5-(6-isocyanatohexyl)-[1,3,5]triazinane-2,4,6-trione-1,3-diyl or 3-(6-isocyanatohexyl)-biuret-1,5-diyl radical(s), or $R_6$ is an n-valent radical of linear or branched $-CO-(C_0-C_{12}alkylene)-(CO)_{n-1}-$ and the alkylene may be interrupted by oxygen, phenylene, cyclohexanediyl or by norbornanediyl;

$R_7$ is hydrogen, $-Si(C_1-C_6alkyl)_3$, $C_1-C_{12}alkyl$, $R_{21}$, $C_2-C_{18}acyl$, $-CO-NH-C_1-C_{12}alkyl$, $C_2-C_{20}hydroxyalkyl$, $C_2-C_{20}methoxyalkyl$, 3-($C_1-C_{18}alkoxy$)-2-hydroxy-propyl, 3-[1,3,3,3-tetramethyl-1-[(trimethylsilyl)oxy]disiloxanyl]-propyl, 2,3-dihydroxypropyl or linear or branched $C_2-C_{21}hydroxyalkyl$ or ($C_1-C_4alkoxy$)-$C_2-C_{21}alkyl$ the carbon chain of which is interrupted by from one to nine oxygen atoms;

$R_{10}$ is hydrogen, $-Si(C_1-C_6alkyl)(CH_3)_2$, $C_1-C_8alkyl$, $C_3-C_6alkenyl$ or benzyl;

$R_{17}$ and $R_{18}$ are each independently of the other a monovalent radical methyl, $-O-Si(CH_3)_3$, $-O-Si(CH_3)_2-O-$ Si(CH₃)₃, —O—Si(CH₃)[—(CH₂)ₚ—OH]—O—Si(CH₃) or a bivalent radical —O—Si(CH₃)₂—, —O—Si(CH₃)[—(CH₂)ₚ—OH]—, —O—Si(CH₃)(R₁₉)—, —O—Si(CH₃)(R₂₀)— and form chains;

R₁₉ and R₂₀ are each independently of the other a monovalent radical methyl, —O—Si(CH₃)₃, —O—Si(CH₃)₂—O—Si(CH₃)₃, —O—Si(CH₃)[—(CH₂)ₚ—OH]—O—Si(CH₃) or a bivalent radical —O—Si(CH₃)₂—, —O—Si(CH₃)[—(CH₂)ₚ—OH]—, and extend chains and, when R₁₉ and R₂₀ are linked into a ring, —(R₁₉)—(R₂₀)— is the bridge —O—;

R₂₁ is, independently of formula III, a radical of the formula

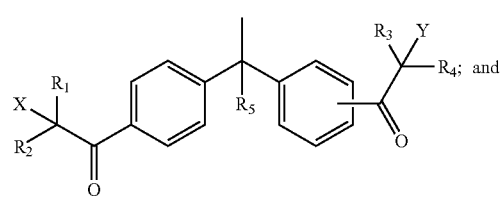

p is an integer from 2 to 12, it being possible for the carbon chain of the alkylene to be interrupted by from one to three oxygen atoms.

3. A photoinitiator according to claim 1 of formula V

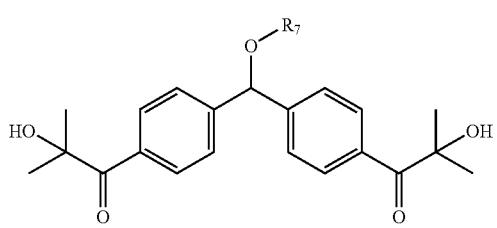

wherein

R₇ is hydrogen, —Si(CH₃)₃, C₁-C₈alkyl, bis[4-(2-hydroxy-2-methyl-propionyl)-phenyl]-methyl, C₂-C₁₈acyl, —CO—NH—C₁-C₈alkyl, C₂-C₂₀hydroxyalkyl, C₂-C₂₀methoxyalkyl or C₂-C₂₀hydroxyalkyl the carbon chain of which is interrupted by from one to nine oxygen atoms.

4. A photoinitiator according to claim 1 of the formula B

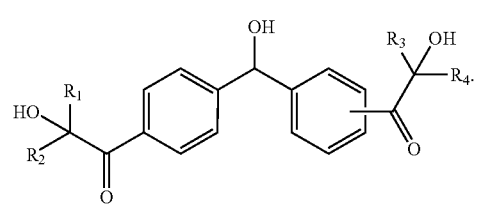

5. A photoinitiator according to claim 1 of formula

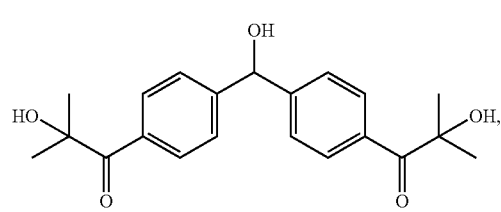

-continued

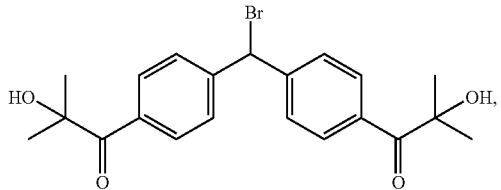

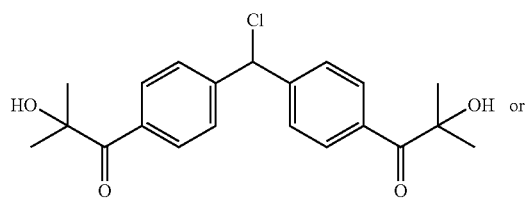

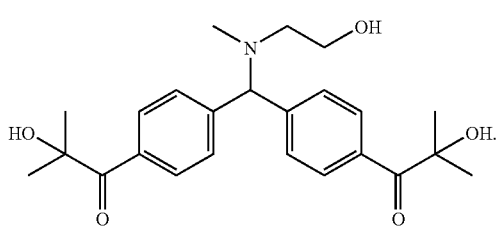

6. A photoinitiator according to claim 1 of formula VI, VII or VIII

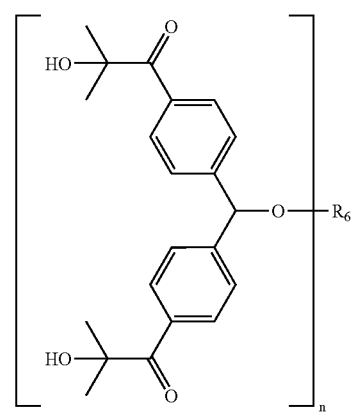

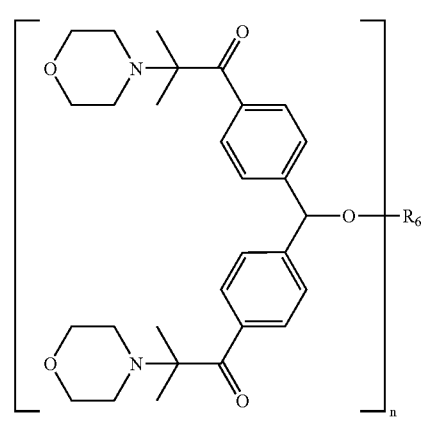

7. A photoinitiator according to claim 1 of formula IX

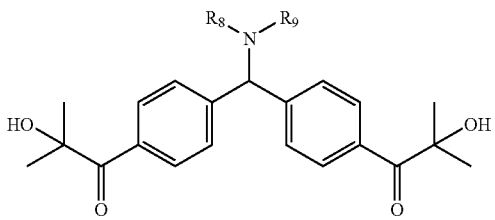

IX wherein $R_8$ and $R_9$ are each independently of the other hydrogen, $C_1$-$C_{12}$alkyl, $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl, or when $R_9$=H or methyl, $R_8$ is also $C_2$-$C_{50}$alkyl substituted by one or more of the groups methyl, ethyl, OH or $NH_2$, and is interrupted by one or more oxygen, —NH—, cyclohexanediyl, norbornanediyl or phenylene, or $R_8$ and $R_9$ together are unbranched or branched $C_3$-$C_9$alkylene which may be interrupted by —O— or by —N($R_{15}$)—.

8. A photoinitiator according to claim 1 of formula X

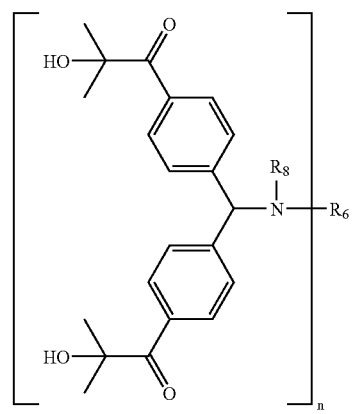

X wherein n is an integer from 1 to 4, and $R_6$ is an n-valent radical of linear or branched $C_2$-$C_{16}$alkyl the carbon chain of which may be interrupted by cyclohexanediyl, phenylene, —CH(OH)—, —C($CH_2$—$CH_2$—OH)$_2$—, —C($CH_3$)($CH_2$—$CH_2$—OH)—, —C($C_2H_5$)($CH_2$—$CH_2$—OH)—, —N($CH_3$)—, —N($CH_2$—$CH_2$—OH)—, —CO—O—, —O—CO—, —O—CO—NH, NH—CO—O—, —Si($CH_3$)$_2$—, —Si($CH_3$)($R_{17}$)—O—Si($CH_3$)($R_{18}$)—, —O—Si($CH_3$)$_2$—O—, —O—Si($CH_3$)(O—$CH_3$)—O—, 5-(2-hydroxyethyl)-[1,3,5]triazinane-2,4,6-trione-1,3-diyl and/or by from one to six oxygen atoms, or $R_6$ is an n-valent radical of linear or branched —$C_2$-$C_{50}$alkylene the carbon chain of which is interrupted by one to 15 oxygen, and may be subsituted by OH or $NH_2$; and $R_8$ is hydrogen, $C_1$-$C_4$alkyl; $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl.

9. A composition consisting of (A) at least one ethylenically unsaturated compound, (B) a photoinitiator of formula I or II according to claim 1, (C) optionally, further additives and -continued

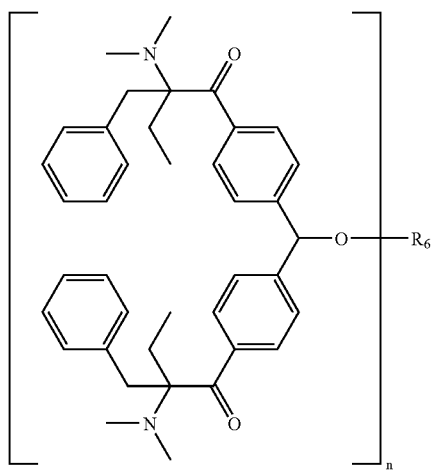

VIII wherein n is an integer from 1 to 4, and $R_6$ is an n-valent radical of linear or branched $C_2$-$C_{16}$alkyl the carbon chain of which may be interrupted by cyclohexanediyl, phenylene, —CH(OH)—, —C($CH_2$—$CH_2$—OH)$_2$—, —C($CH_3$)($CH_2$—$CH_2$—OH)—, —C($C_2H_5$)($CH_2$—$CH_2$—OH)—, —N($CH_3$)—, —N($CH_2$—$CH_2$—OH)—, —CO—O—, —O—CO—, —Si($CH_3$)$_2$—, —Si($CH_3$)($R_{17}$)—O—Si($CH_3$)($R_{18}$)—, —O—Si($CH_3$)$_2$—O—, —O—Si($CH_3$)(O—$CH_3$)—O—, 5-(2-hydroxyethyl)-[1,3,5]triazinane-2,4,6-trione-1,3-diyl and/or by from one to six oxygen atoms, or $R_6$ is an n-valent radical of linear or branched —CO—NH—($C_2$-$C_{16}$alkylene)-(NH—CO)$_{n-1}$— or linear or branched —CO—NH—($C_0$-$C_9$alkylene)-(NH—CO)$_{n-1}$— which may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl, 5-(6-isocyanatohexyl)-[1,3,5]triazinane-2,4,6-trione-1,3-diyl or 3-(6-isocyanatohexyl)-biuret-1,5-diyl radical(s), $R_{17}$ and $R_{18}$ are each independently of the other a monovalent radical methyl, —O—Si($CH_3$)$_3$, —O—Si($CH_3$)$_2$—O—Si($CH_3$)$_3$, —O—Si($CH_3$)[—($CH_2$)$_p$—OH]—O—Si($CH_3$) or a bivalent radical —O—Si($CH_3$)$_2$—, —O—Si($CH_3$)[—($CH_2$)$_p$—OH]—, —O—Si($CH_3$)($R_{19}$)—, —O—Si($CH_3$)($R_{20}$)— and form chains, $R_{19}$ and $R_{20}$ are each independently of the other a monovalent radical methyl, —O—Si($CH_3$)$_3$, —O—Si($CH_3$)$_2$—O—Si($CH_3$)$_3$, —O—Si($CH_3$)[—($CH_2$)$_p$—OH]—O—Si($CH_3$) or a bivalent radical —O—Si($CH_3$)$_2$—, —O—Si($CH_3$)[—($CH_2$)$_p$—OH]—, and extend chains and, when $R_{19}$ and $R_{20}$ are linked into a ring, —($R_{19}$)—($R_{20}$)— is the bridge —O—, and p is an integer from 2 to 12, it being possible for the carbon chain of the alkylene to be interrupted by from one to three oxygen atoms.

(D) optionally, further photoinitiators and coinitiators.

10. A composition according to claim 9, wherein the compound (A) is a resin containing free OH groups, free isocyanate groups or free carboxy groups and the photoinitiator (B) is bonded to the resin.

11. A composition according to claim 10 which is a surface coating for food packaging materials.

12. A process for the production of a scratch-resistant durable surface, wherein a composition according to claim 9 is applied to a support; and curing is carried out either solely by means of irradiation with electromagnetic radiation having a wavelength of from 200 nm into the IR range, or by irradiation with electromagnetic radiation and prior, simultaneous and/or subsequent application of heat.

13. A composition according to claim 9 which is a pigmented or non-pigmented surface coating, overprint coating, powder coating, printing ink, inkjet ink, gel coat, composite material or a glass fibre coating.

14. A process for the preparation of a compound of formula I or II, comprising the following steps:

a) reaction of diphenylmethane with an acid halide of formula $R_1R_2CH$—COHal and, optionally, further reaction with an acid halide of formula $R_3R_4CH$—COHal in the presence of a Friedel-Crafts catalyst, whereupon an isomeric mixture of formula A is obtained,

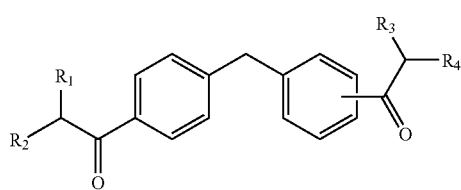

b) halogenation of the isomeric mixture of formula A, followed by bromination and hydrolysis, whereupon an isomeric mixture of formula B is obtained,

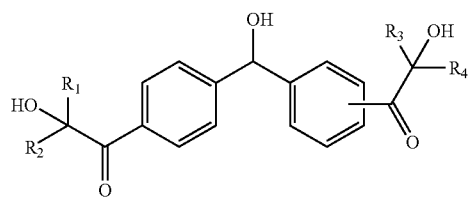

c) optionally, selective substitution of the benzylic hydroxy group in the resulting isomeric mixture of formula B by reaction
  with an alcohol in the presence of an acid as catalyst for the preparation of an ether,
  with a carboxylic acid for the preparation of an ester,
  with an isocyanate for the preparation of a urethane,
  with a diol, dicarboxylic acid or diisocyanate for the preparation of a bridged compound,
  with a diisocyanate together with a diol or a diamine or
  with a siloxane for the preparation of a silicone derivative, d) optionally, reaction of the alpha-hydroxy group in the resulting isomeric mixture of formula B and e) optionally, separation of the isomers,
where the compounds of formula I and II are

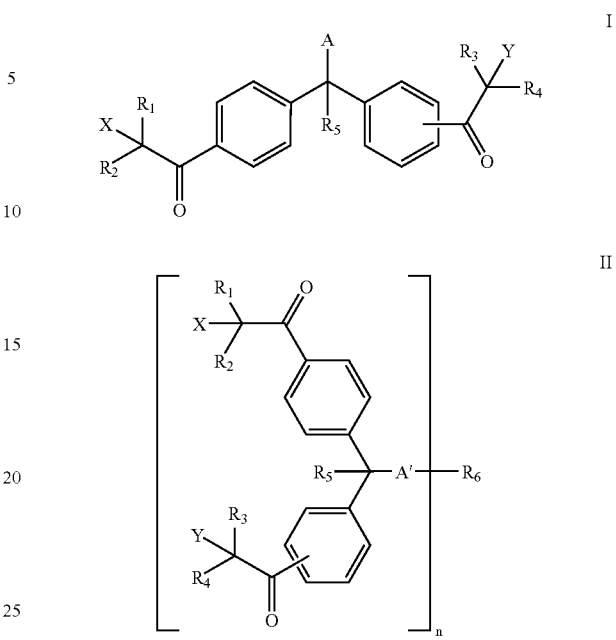

wherein $R_1$, $R_2$, $R_3$ and $R_4$ are each independently of the others $C_1$-$C_8$alkyl; $C_1$-$C_4$alkyl substituted by OH, $C_1$-$C_4$alkoxy, —CN, —COO($C_1$-$C_8$alkyl), ($C_1$-$C_4$alkyl)-COO—, benzyl, phenyl or by —N($R_{13}$)($R_{14}$);

$C_3$-$C_6$alkenyl, benzyl, —CH$_2$—C$_6$H$_4$—(C$_1$-C$_4$alkyl) or phenyl; or $R_1$ and $R_2$ together and/or $R_3$ and $R_4$ together are unbranched or branched $C_2$-$C_9$alkylene or $C_3$-$C_6$-oxa- or -aza-alkylene;

$R_5$ is hydrogen, $C_1$-$C_8$alkyl, $C_3$-$C_6$alkenyl, benzyl, —CH$_2$—C$_6$H$_4$—(C$_1$-C$_4$alkyl) or phenyl;

A is Cl, Br, —O—$R_7$—N$R_8R_9$ or —S—$R_{16}$;

A' is —O—, —NH— or —N$R_8$—;

X and Y are each independently of the other —O—$R_{10}$ or —N($R_{11}$)($R_{12}$);

n is an integer from 1 to 10;

$R_6$ is an n-valent radical of linear or branched $C_2$-$C_{20}$alkyl the carbon chain of which may be interrupted by cyclohexanediyl, phenylene, —CH(OH)—, —C(C$_2$H$_5$)(CH$_2$—CH$_2$—OH)—, —C(CH$_3$)(CH$_2$—CH$_2$OH)—, —C(CH$_2$—CH$_2$—OH)$_2$—, —N(CH$_3$)—, —N(C$_2$H$_5$)—, —N(CH$_2$—CH$_2$—OH)—, —CO—O—, —O—CO—, —O—CO—NH, NH—CO—O—, —P(CH$_2$—CH$_2$—OH)—, —P(O)(CH$_2$—CH$_2$—OH)—, —O—P(O—CH$_2$—CH$_2$—OH)—O—, —O—P(O)(O—CH$_2$—CH$_2$—OH)—O—, —O-cyclohexanediyl-C(CH$_3$)$_2$-cyclohexanediyl-O—, —O-phenylene-C(CH$_3$)$_2$-phenylene-O—, —O-phenylene-CH$_2$-phenylene-O—, —Si(CH$_3$)$_2$—, —O—Si(CH$_3$)$_2$—O—, —O—Si(CH$_3$)(O—CH$_3$)—O—, —Si(CH$_3$)(R$_{17}$)—O—Si(CH$_3$)(R$_{18}$)—, 5-(2-hydroxyethyl)-1,3,5triazinane-2,4,6-trione-1,3-diyl and/or by from one to nine oxygen atoms, or $R_6$ is an n-valent radical of linear or branched —CO—NH—(C$_2$-C$_{16}$alkylene)-(NH—CO)$_{n-1}$— or linear or branched —CO—NH—(C$_0$-C$_9$alkylene)-(NH—CO)$_{n-1}$— which may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl, 3-(6-isocyanatohexyl)-biuret-1,5-diyl or 5-(6-isocyanatohexyl)-[1,3,5]triazinane-2,4,6-trione-1,3-diyl radical(s), or $R_6$ is an n-valent radical of linear or branched —CO—($C_0$-$C_{12}$alkylene)-(CO)$_{n-1}$— and the alkylene may be interrupted by oxygen, phenylene, cyclohexanediyl or by norbornanediyl; or $R_6$ is an n-valent radical of linear or branched —$C_2$-$C_{50}$alkylene the carbon chain of which is interrupted by one to 15 oxygen, and may be subsituted by OH or $NH_2$;

$R_7$ is hydrogen, —Si($C_1$-$C_6$alkyl)$_3$, $C_1$-$C_{12}$alkyl, $R_{21}$, $C_2$-$C_{18}$acyl, —CO—NH—$C_1$-$C_{12}$alkyl, $C_2$-$C_{20}$hydroxyalkyl, $C_2$-$C_{20}$methoxyalkyl, 3-($C_1$-$C_{18}$alkoxy)-2-hydroxy-propyl, 3-[1,3,3,3-tetramethyl-1-[(trimethylsilyl)oxy]disiloxanyl]-propyl, 2,3-dihydroxy-propyl or linear or branched $C_2$-$C_{21}$hydroxyalkyl or ($C_1$-$C_4$alkoxy)-$C_2$-$C_{22}$alkyl the carbon chain of which is interrupted by from one to nine oxygen atoms;

$R_8$ and $R_9$ are each independently of the other hydrogen, $C_1$-$C_{12}$alkyl; $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl, or when $R_9$=H or methyl, $R_8$ is also $C_2$-$C_{50}$alkyl substituted by one or more of the groups methyl, ethyl, OH, $NH_2$, and is interrupted by one or more oxygen, —NH—, cyclohexanediyl, norbornanediyl or phenylene, or $R_8$ and $R_9$ together are unbranched or branched $C_3$-$C_9$alkylene which may be interrupted by —O— or by —N($R_{15}$)—;

$R_{10}$ is hydrogen, —Si($C_1$-$C_6$alkyl)$_3$, $C_1$-$C_8$alkyl, $C_3$-$C_6$alkenyl or benzyl, $R_{11}$ and $R_{12}$, are each independently of the other $C_1$-$C_{12}$alkyl; $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl, or $R_{11}$ and $R_{12}$ together are unbranched or branched $C_3$-$C_9$alkylene which may be interrupted by —O— or by —N($R_{15}$)—;

$R_{13}$ and $R_{14}$ are each independently of the other hydrogen, $C_1$-$C_{12}$alkyl; $C_2$-$C_4$alkyl substituted by one or more of the groups OH, $C_1$-$C_4$alkoxy, —CN, —COO($C_1$-$C_4$alkyl); $C_3$-$C_5$alkenyl, cyclohexyl or $C_7$-$C_9$phenylalkyl, or $R_{13}$ and $R_{14}$ together are unbranched or branched $C_3$-$C_9$alkylene which may be interrupted by —O— or by —N($R_{15}$)—;

$R_{15}$ is hydrogen, $C_1$-$C_4$alkyl, allyl, benzyl, $C_1$-$C_4$hydroxyalkyl, —$CH_2CH_2$—COO($C_1$-$C_4$alkyl) or —$CH_2CH_2$CN;

$R_{16}$ is $C_1$-$C_{18}$alkyl, hydroxyethyl, 2,3-dihydroxypropyl, cyclohexyl, benzyl, phenyl, $C_1$-$C_{12}$alkylphenyl, —$CH_2$—COO($C_1$-$C_{18}$alkyl), —$CH_2CH_2$—COO($C_1$-$C_{18}$alkyl) or —CH($CH_3$)—COO($C_1$-$C_{18}$alkyl);

$R_{17}$ and $R_{18}$ are each independently of the other a monovalent radical methyl, —O—Si($CH_3$)$_3$, —O—Si($CH_3$)$_2$—O—Si($CH_3$)$_3$, —O—Si($CH_3$)[—($CH_2$)$_p$—OH]—O—Si($CH_3$) or a bivalent radical —O—Si($CH_3$)$_2$—, —O—Si($CH_3$)[—($CH_2$)$_p$—OH]—, —O—Si($CH_3$)($R_{19}$)—, —O—Si($CH_3$)($R_{20}$)— and form chains;

$R_{19}$ and $R_{20}$ are each independently of the other a monovalent radical methyl, —O—Si($CH_3$)$_3$, —O—Si($CH_3$)$_2$—O—Si($CH_3$)$_3$, —O—Si($CH_3$)[—($CH_9$)$_p$—OH]—O—Si($CH_3$) or a bivalent radical —O—Si($CH_3$)$_2$—, —O—Si($CH_3$)[—($CH_2$)$_p$—OH]—, and extend chains and, when $R_{19}$ and $R_{20}$ are linked into a ring, —($R_{19}$)—($R_{20}$)— is the bridge —O—;

$R_{21}$ is independently of formula I, a radical of the formula

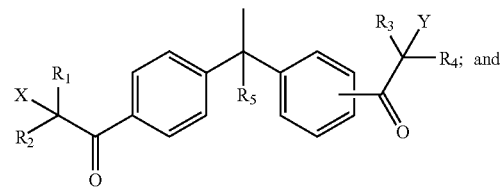

p is an integer from 2 to 12, it being possible for the carbon chain of the alkylene to be interrupted by from one to three oxygen atoms.

15. A process for the preparation of compound I or II, comprising the following steps:
a) reaction of diphenylmethane with an acid halide of formula $R_1R_2$CH—COHal and, optionally, further reaction with an acid halide of formula $R_3R_4$CH—COHal in the presence of a Friedel-Crafts catalyst, whereupon an isomeric mixture of formula A is obtained,

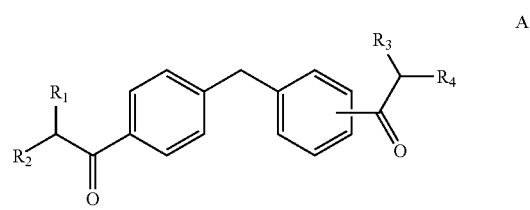

b) halogenation of the isomeric mixture of formula A, followed by bromination, aminolysis of the benzylic bromide, and hydrolysis of the tertiary halides, whereupon an isomeric mixture of formula C is obtained,

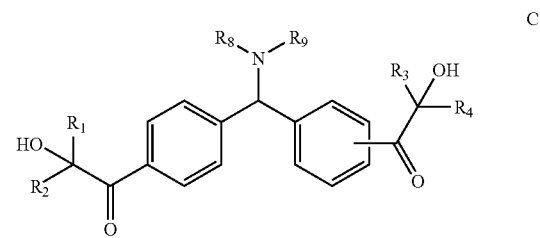

c) optionally, when $R_8$ or $R_9$ in the isomeric mixture of formula C possess a primary hydroxy group, selective substitution of the primary hydroxy group by reaction with a carboxylic acid for the preparation of an ester, with an isocyanate for the preparation of a urethane, with a dicarboxylic acid or diisocyanate for the preparation of a bridged compound or with a siloxane for the preparation of a silicone derivative and d) optionally, separation of the isomers, where the compounds of formula I and II are

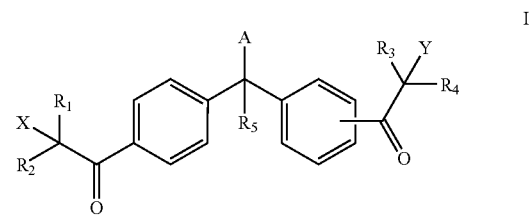

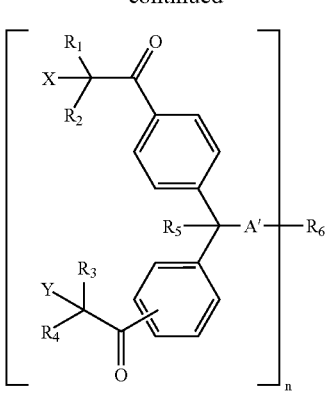

wherein

R$_1$, R$_2$, R$_3$ and R$_4$ are each independently of the others C$_1$-C$_8$alkyl; C$_1$-C$_4$alkyl substituted by OH, C$_1$-C$_4$alkoxy, —CN, —COO(C$_1$-C$_8$alkyl), (C$_1$-C$_4$alkyl)-COO—, benzyl, phenyl or by —N(R$_{13}$)(R$_{14}$);

C$_3$-C$_6$alkenyl, benzyl, —CH$_2$—C$_6$H$_4$—(C$_1$-C$_4$alkyl) or phenyl; or

R$_1$ and R$_2$ together and/or R$_3$ and R$_4$ together are unbranched or branched C$_2$-C$_9$alkylene or C$_3$-C$_6$-oxa- or -aza-alkylene;

R$_5$ is hydrogen, C$_1$-C$_8$alkyl, C$_3$-C$_6$alkenyl, benzyl, —CH$_2$—C$_6$H$_4$-(C$_1$-C$_4$alkyl) or phenyl;

A is Cl, Br, —O—R$_7$—NR$_8$R$_9$ or —S—R$_{16}$;

A' is —O—, —NH— or —NR$_8$—;

X and Y are each independently of the other —O—R$_{10}$ or —N(R$_{11}$)(R$_{12}$);

n is an integer from 1 to 10;

R$_6$ is an n-valent radical of linear or branched C$_2$C$_{20}$alkyl the carbon chain of which may be interrupted by cyclohexanediyl, phenylene, —CH(OH)—, —C(C$_2$H$_5$)(CH$_2$—CH$_2$—OH)—, —C(CH$_3$)(CH$_2$—CH$_2$—OH)—, —C(CH$_2$—CH$_2$—OH)$_2$—, —N(CH$_3$)—, —N(C$_2$H$_5$)—, —N(CH$_2$—CH$_2$—OH)—, —CO—O—, —O—CO—, —O—CO—NH, NH—CO—O—, —P(CH$_2$—CH—OH)—, —P(O)(CH$_2$—CH$_2$—OH)—, —O—P(O—CH$_2$—CH$_2$—OH)—O—, —O—P(O)(O—CH$_2$—CH$_2$—OH)—O—, —O-cyclohexanediyl-C(CH$_3$)$_2$-cyclohexanediyl-O—, —O-phenylene-C(CH$_3$)$_2$-phenylene-O—, —O-phenylene-CH$_2$-phenylene-O—, —Si(CH$_3$)$_2$—, —O—Si(CH$_3$)$_2$—O—, —O—Si(CH$_3$)(O—CH$_3$)—O—, —Si(CH$_3$)(R$_{17}$)—O—Si(CH$_3$)(R$_{18}$)—, 5-(2-hydroxyethyl)-[1,3,5]triazinane-2,4,6-trione-1,3-diyl and/or by from one to nine oxygen atoms, or R$_6$ is an n-valent radical of linear or branched —CO—NH—(C$_2$-C$_{16}$alkylene)-(NH—CO)$_{n-1}$— or linear or branched —CO—NH—(C$_0$-C$_9$alkylene)-(NH—CO)$_{n-1}$— which may be interrupted by one or two phenylene, methylphenylene, phenylene-O-phenylene, cyclohexanediyl, methylcyclohexanediyl, trimethylcyclohexanediyl, norbornanediyl, [1-3]diazetidine-2,4-dione-1,3-diyl, 3-(6-isocyanatohexyl)-biuret-1,5-diyl or 5-(6-isocyanatohexyl)-[1,3,5]triazinane-2,4,6-trione-1,3-diyl radical(s), or R$_6$ is an n-valent radical of linear or branched —CO—(C$_0$-C$_{12}$alkylene)-(CO)$_{n-1}$— and the alkylene may be interrupted by oxygen, phenylene, cyclohexanediyl or by norbornanediyl; or R$_6$ is an n-valent radical of linear or branched —C$_2$-C$_{50}$alkylene the carbon chain of which is interrupted by one to 15 oxygen, and may be subsituted by OH or NH$_2$;

R$_7$ is hydrogen, —Si(C$_1$-C$_6$alkyl)$_3$, C$_1$-C$_{12}$alkyl, R$_{21}$, C$_2$-C$_{18}$acyl, —CO—NH—C$_1$-C$_{12}$alkyl, C$_2$-C$_{20}$hydroxyalkyl, C$_2$-C$_{20}$methoxyalkyl, 3-(C$_1$-C$_{18}$alkoxy)-2-hydroxy-propyl, 3-[1,3,3,3-tetramethyl-1-[(trimethylsilyl)oxy]disiloxanyl]-propyl, 2,3-dihydroxy-propyl or linear or branched C$_2$-C$_{21}$, hydroxyalkyl or (C$_1$-C$_4$alkoxy)-C$_2$-C$_{21}$alkyl the carbon chain of which is interrupted by from one to nine oxygen atoms, R$_8$ and R$_9$ are each independently of the other hydrogen, C$_1$-C$_{12}$alkyl; C$_2$-C$_4$alkyl substituted by one or more of the groups OH, C$_1$-C$_4$alkoxy, —CN, —COO(C$_1$-C$_4$alkyl); C$_3$-C$_5$alkenyl, cyclohexyl or C$_7$-C$_9$phenylalkyl, or when R$_9$=H or methyl, R$_8$ is also C$_2$-C$_{50}$alkyl substituted by one or more of the groups methyl, ethyl, OH, NH$_2$, and is interrupted by one or more oxygen, —NH—, cyclohexanediyl, norbornanediyl or phenylene, or R$_8$ and R$_9$ together are unbranched or branched C$_3$-C$_9$alkylene which may be interrupted by —O— or by —N(R$_{15}$)—;

R$_{10}$ is hydrogen, —Si(C$_1$-C$_6$alkyl)$_3$, C$_1$-C$_8$alkyl, C$_3$-C$_6$alkenyl or-benzyl, R$_{11}$ and R$_{12}$, are each independently of the other C$_1$-C$_{12}$alkyl; C$_2$-C$_4$alkyl substituted by one or more of the groups OH, C$_1$-C$_4$alkoxy, —CN, —COO(C$_1$-C$_4$alkyl); C$_3$-C$_5$alkenyl, cyclohexyl or C$_7$-C$_9$phenylalkyl, or R$_{11}$ and R$_{12}$ together are unbranched or branched C$_3$-C$_9$alkylene which may be interrupted by —O— or by —N(R$_{15}$)—;

R$_{13}$ and R$_{14}$ are each independently of the other hydrogen, C$_1$-C$_{12}$alkyl; C$_2$-C$_4$alkyl substituted by one or more of the groups OH, C$_1$-C$_4$alkoxy, —CN, —COO(C$_1$-C$_4$alkyl); C$_3$-C$_5$alkenyl, cyclohexyl or C$_7$-C$_9$phenylalkyl, or R$_{13}$ and R$_{14}$ together are unbranched or branched C$_3$-C$_9$alkylene which may be interrupted by —O— or by —N(R$_{15}$)—;

R$_{15}$ is hydrogen, C$_1$-C$_4$alkyl, allyl, benzyl, C$_1$-C$_4$hydroxyalkyl, —CH$_2$CH$_2$—COO(C$_1$-C$_4$alkyl) or —CH$_2$CH$_2$CN;

R$_{16}$ is C$_1$-C$_{18}$alkyl, hydroxyethyl, 2,3-dihydroxypropyl, cyclohexyl, benzyl, phenyl, C$_1$-C$_{12}$alkylphenyl, —CH$_2$—COO(C$_1$-C$_{18}$alkyl), —CH$_2$CH$_2$—COO(C$_1$-C$_{10}$alkyl) or —CH(CH$_3$)—COO(C$_1$-C$_{18}$alkyl);

R$_{17}$ and R$_{18}$ are each independently of the other a monovalent radical methyl, —O—Si(CH$_3$)$_3$, —O—Si(CH$_3$)$_2$—O—Si(CH$_3$)$_3$, —O—Si(CH$_3$)[—(CH$_2$)$_p$—OH]—O—Si(CH$_3$) or a bivalent radical —O—Si(CH$_3$)$_2$—, —O—Si(CH$_3$)[—(CH$_2$)$_p$—OH]—, —O—Si(CH$_3$)(R$_{19}$)—, —O—Si(CH$_3$)(R$_{20}$)— and form chains;

R$_{19}$ and R$_{20}$ are each independently of the other a monovalent radical methyl, —O—Si(CH$_3$)$_3$, —O—Si(CH$_3$)$_2$—O—Si(CH$_3$)$_3$, —O—Si(CH$_3$)[—(CH$_2$)$_p$—OH]—O—Si(CH$_3$) or a bivalent radical —O—Si(CH$_3$)$_2$—, —O—Si(CH$_3$)[—(CH$_2$)$_p$—OH]—, and extend chains and, when R$_{19}$ and R$_{20}$ are linked into a ring, —(R$_{19}$)—(R$_{20}$)— is the bridge —O—;

R$_{21}$ is, independently of formula I, a radical of the formula

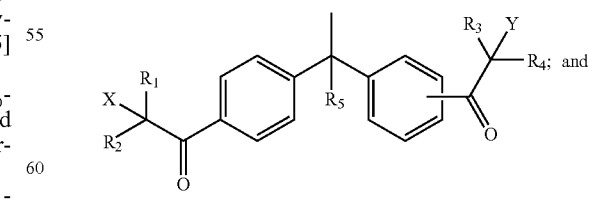

p is an integer from 2 to 12, it being possible for the carbon chain of the alkylene to be interrupted by from one to three oxygen atoms.

* * * * *